(12) United States Patent
Kamatani et al.

(10) Patent No.: US 8,158,835 B2
(45) Date of Patent: Apr. 17, 2012

(54) FLUORENE COMPOUND AND ORGANIC ELECTROLUMINESCENCE DEVICE

(75) Inventors: Jun Kamatani, Tokyo (JP); Shinjiro Okada, Kamakura (JP); Takao Takiguchi, Chofu (JP); Satoshi Igawa, Fujisawa (JP); Masashi Hashimoto, Tokyo (JP); Minako Nakasu, Tokyo (JP); Ryota Ooishi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 968 days.

(21) Appl. No.: 11/914,406

(22) PCT Filed: Dec. 14, 2006

(86) PCT No.: PCT/JP2006/325451
§ 371 (c)(1),
(2), (4) Date: Nov. 14, 2007

(87) PCT Pub. No.: WO2007/072889
PCT Pub. Date: Jun. 28, 2007

(65) Prior Publication Data
US 2009/0200919 A1     Aug. 13, 2009

(30) Foreign Application Priority Data

Dec. 20, 2005   (JP) ................. 2005-366205
Apr. 14, 2006   (JP) ................. 2006-111726
Dec. 5, 2006    (JP) ................. 2006-327780

(51) Int. Cl.
C07C 19/08    (2006.01)
C07C 22/00    (2006.01)
C07C 25/13    (2006.01)
H01L 29/08    (2006.01)
H01L 35/24    (2006.01)
H01L 51/00    (2006.01)

(52) U.S. Cl. .......................... 570/129; 257/40
(58) Field of Classification Search ............ None
See application file for complete search history.

(56) References Cited

U.S. PATENT DOCUMENTS

| | | | |
|---|---|---|---|
| 2004/0253389 A1 | 12/2004 | Suzuki et al. | 428/1.1 |
| 2005/0256290 A1 | 11/2005 | Cella et al. | 528/219 |
| 2006/0003171 A1 | 1/2006 | Igawa et al. | |
| 2006/0121312 A1 | 6/2006 | Yamada et al. | 428/690 |
| 2006/0159956 A1 | 7/2006 | Ito et al. | 428/690 |
| 2007/0122652 A1 | 5/2007 | Hashimoto et al. | |
| 2007/0184302 A1 | 8/2007 | Iwawaki et al. | |
| 2007/0232841 A1 | 10/2007 | Igawa et al. | |
| 2007/0249878 A1 | 10/2007 | Iwawaki et al. | |
| 2007/0257604 A1 | 11/2007 | Kamatani et al. | |
| 2008/0007161 A1 | 1/2008 | Kamatani et al. | |
| 2009/0066227 A1* | 3/2009 | Okinaka et al. | 313/504 |

FOREIGN PATENT DOCUMENTS

| | | |
|---|---|---|
| JP | 11-224779 | 8/1999 |
| JP | 2001-039933 | 2/2001 |
| JP | 2003-105332 | 4/2003 |
| JP | 2003229273 | 8/2003 |
| JP | 2004043349 | 2/2004 |
| JP | 2006-124373 | 5/2006 |
| JP | 2006-151845 | 6/2006 |
| WO | 9954385 | 10/1999 |
| WO | WO 2005/123634 A1 | 12/2005 |
| WO | WO 2006/001333 A1 | 1/2006 |

OTHER PUBLICATIONS

JP-2003105332, machine translation, 2003, 1-48.*
Kauffman, et al. "Electronic Absorption and Emission Spectral Data and Fluorescence Quantum Yields of Bridged p-Oligophenylenes, Bi- to Deciphenyls, and Related Furans and Carbazoles", Journal of Fluorescence, vol. 5, No. 3, pp. 295-443 (1995).

* cited by examiner

*Primary Examiner* — Daniel Sullivan
*Assistant Examiner* — Clinton Brooks
(74) *Attorney, Agent, or Firm* — Fitzpatrick, Cella, Harper & Scinto

(57) ABSTRACT
Provided is a novel fluorene compound, which is represented by the following general formula (1):
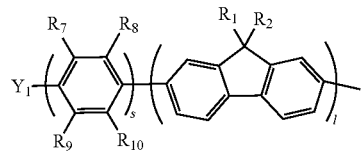
(1)
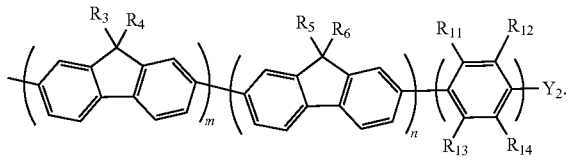
-continued
2 Claims, 1 Drawing Sheet

FLUORENE COMPOUND AND ORGANIC ELECTROLUMINESCENCE DEVICE

TECHNICAL FIELD

The present invention relates to a fluorene compound, and an organic electroluminescence device (organic EL device) using the fluorene compound.

BACKGROUND ART

The recent progress of an organic light emitting device is significant, and the device suggests its potential to find use in a wide variety of applications because of the following reasons. The device shows a high luminance at a low applied voltage. In addition, the device has a variety of emission wavelengths. Furthermore, the device can be a thin, lightweight light emitting device with high-speed responsiveness.

However, at present, an optical output with additionally high luminance, or additionally high conversion efficiency has been needed. In addition, the organic light emitting device still has many problems in terms of durability. For example, the device changes over time owing to long-term use, and deteriorates owing to an atmospheric gas containing oxygen, humidity, or the like. Further, in the case where it is assumed that the device is applied to, for example, a full-color display, the device must emit blue light, green light, and red light each having good color purity. However, problems concerning the color purity of each of the blue light, the green light, and the red light have not been sufficiently solved yet.

In addition, research has been conducted on a large number of aromatic compounds and condensed polycyclic aromatic compounds as fluorescent organic compounds each of which is used in, for example, an electron transport layer or a light emitting layer. However, it is hard to say that a compound capable of sufficiently satisfying emission luminance or durability has been obtained.

Japanese Patent Application Laid-Open No. 2004-43349, International Publication No. 99/54385, and Japanese Patent Application Laid-Open No. 2003-229273 each disclose the application of a fluorene compound to an organic EL. In addition, Journal of Fluorescence, Vol. 5, No. 3, 295 (1995) reports a fluorene compound to be applied to a laser dye.

DISCLOSURE OF THE INVENTION

The application of an organic EL device to a display apparatus such as a display requests the organic EL device to have an optical output with high efficiency and high luminance, and, at the same time, to secure high durability sufficiently. However, it cannot be said that problems concerning the optical output and the durability have already been sufficiently solved.

An object of the present invention is to provide a novel fluorene compound.

Another object of the present invention is to provide an organic EL device using the fluorene compound and having an optical output with high efficiency and high luminance. Another object of the present invention is to provide an organic EL device having high durability. Another object of the present invention is to provide an organic EL device that can be easily produced at a relatively low cost.

That is, according to the present invention, there are provided fluorene compounds as follows.

A fluorene compound represented by the following general formula (1):

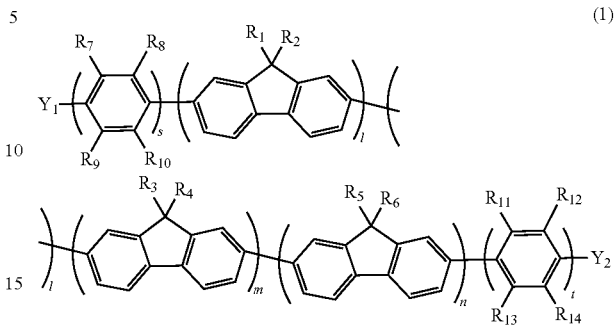

wherein:

$R_1$ to $R_{14}$ are each independently selected from the group consisting of a hydrogen atom, a halogen atom, a linear or branched alkyl group having 1 to 20 carbon atoms, in which one methylene group or two or more non-adjacent methylene groups each may be substituted by —O—, —S—, —CO—, —CO—O—, —O—CO—, —CH=CH—, or —C≡C—, one or two or more methylene groups each may be substituted by an arylene group which may have a substituent or a divalent heterocyclic group which may have a substituent, and a hydrogen atom in the alkyl group may be substituted by a fluorine atom, an amino group which may have a substituent, a silyl group which may have a substituent, an aryl group which may have a substituent, and a heterocyclic group which may have a substituent;

$Y_1$ is composed of a condensed ring structure which is constituted only of $SP^2$ carbon and hydrogen and which may have a substituent;

$Y_2$ is composed of a hydrogen atom, or a condensed ring structure which is constituted only of $SP^2$ carbon and hydrogen and which may have a substituent provided that $Y_2$ is composed of a hydrogen atom when t=0;

l, m, and n each represent an integer of 0 to 10, and a total of l, m, and n represents an integer of 1 to 20, s represents an integer of 1 to 10, and t represents an integer of 0 to 10; and substituents each appearing in a phrase "may have a substituent" are each independently selected from the group consisting of a halogen atom, a linear or branched alkyl group having 1 to 20 carbon atoms, in which one methylene group or two or more non-adjacent methylene groups each may be substituted by —O—, —S—, —CO—, —CO—O—, —O—CO—, —CH=CH—, or —C≡C—, one or two or more methylene groups each may be substituted by an arylene group or a divalent heterocyclic group, and a hydrogen atom in the alkyl group may be substituted by a fluorine atom, an amino group, a silyl group, an aryl group, and a heterocyclic group.

A fluorene compound represented by the following general formula (2):

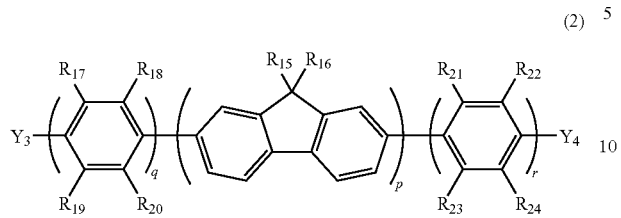

(2)

wherein:

$R_{15}$ to $R_{24}$ are each independently selected from the group consisting of a hydrogen atom, a halogen atom, a linear or branched alkyl group having 1 to 20 carbon atoms, in which one methylene group or two or more non-adjacent methylene groups each may be substituted by —O—, —S—, —CO—, —CO—O—, —O—CO—, —CH=CH—, or —C≡C—, one or two or more methylene groups each may be substituted by an arylene group which may have a substituent or a divalent heterocyclic group which may have a substituent, and a hydrogen atom in the alkyl group may be substituted by a fluorine atom, an amino group which may have a substituent, a silyl group which may have a substituent, an aryl group which may have a substituent, and a heterocyclic group which may have a substituent;

$Y_3$ is composed of a condensed ring structure which is constituted only of $SP^2$ carbon and hydrogen and which may have a substituent;

$Y_4$ is composed of a hydrogen atom, or a condensed ring structure which is constituted only of $SP^2$ carbon and hydrogen and which may have a substituent provided that $Y_4$ is composed of a hydrogen atom when r=0;

p represents an integer of 1 to 20;

q represents an integer of 1 to 10, and r represents an integer of 0 to 10; and substituents each appearing in a phrase "may have a substituent" are each independently selected from the group consisting of a halogen atom, a linear or branched alkyl group having 1 to 20 carbon atoms, in which one methylene group or two or more non-adjacent methylene groups each may be substituted by —O—, —S—, —CO—, —CO—O—, —O—CO—, —CH=CH—, or —C≡C—, one or two or more methylene groups each may be substituted by an arylene group or a divalent heterocyclic group, and a hydrogen atom in the alkyl group may be substituted by a fluorine atom, a diphenylamino group, a triphenylsilyl group, an aryl group, and a heterocyclic group.

A fluorene compound represented by the following general formula (3):

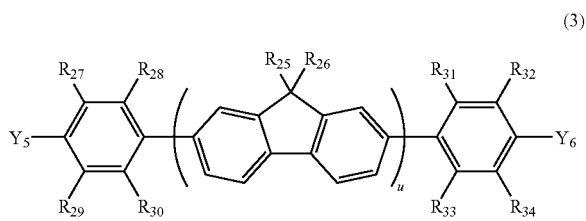

(3)

wherein:

$R_{25}$ to $R_{34}$ are each independently selected from the group consisting of a hydrogen atom, a halogen atom, a linear or branched alkyl group having 1 to 20 carbon atoms, in which one methylene group or two or more non-adjacent methylene groups each may be substituted by —O—, —S—, —CO—, —CO—O—, —O—CO—, —CH=CH—, or —C≡C—, one or two or more methylene groups each may be substituted by an arylene group which may have a substituent or a divalent heterocyclic group which may have a substituent, and a hydrogen atom in the alkyl group may be substituted by a fluorine atom, an amino group which may have a substituent, a silyl group which may have a substituent, an aryl group which may have a substituent, and a heterocyclic group which may have a substituent;

$Y_5$ and $Y_6$ are composed of a condensed ring structure which is constituted only of $SP^2$ carbon and hydrogen and which may have a substituent;

u represents an integer of 1 to 20; and substituents each appearing in a phrase "may have a substituent" are each independently selected from the group consisting of a halogen atom, a linear or branched alkyl group having 1 to 20 carbon atoms, in which one methylene group or two or more non-adjacent methylene groups each may be substituted by —O—, —S—, —CO—, —CO—O—, —O—CO—, —CH=CH—, or —C≡C—, one or two or more methylene groups each may be substituted by an arylene group or a divalent heterocyclic group, and a hydrogen atom in the alkyl group may be substituted by a fluorine atom, a diphehylamino group, a triphenylsilyl group, an aryl group, and a heterocyclic group.

A fluorene compound represented by the following general formula (4):

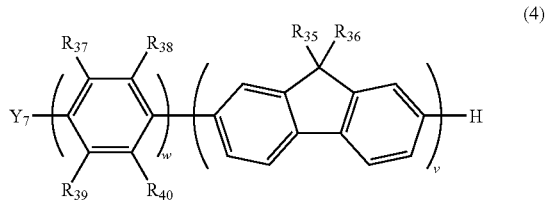

(4)

wherein:

$R_{35}$ to $R_{40}$ are each independently selected from the group consisting of a hydrogen atom, a halogen atom, a linear or branched alkyl group having 1 to 20 carbon atoms, in which one methylene group or two or more non-adjacent methylene groups each may be substituted by —O—, —S—, —CO—, —CO—O—, —O—CO—, —CH=CH—, or —C≡C—, one or two or more methylene groups each may be substituted by an arylene group which may have a substituent or a divalent heterocyclic group which may have a substituent, and a hydrogen atom in the alkyl group may be substituted by a fluorine atom, an amino group which may have a substituent, a silyl group which may have a substituent, an aryl group which may have a substituent, and a heterocyclic group which may have a substituent;

$Y_7$ is composed of a condensed ring structure which is constituted only of $SP^2$ carbon and hydrogen and which may have a substituent;

v represents an integer of 1 to 20;

w represents an integer of 1 to 10; and substituents each appearing in a phrase "may have a substituent" are each independently selected from the group consisting of a halogen atom, a linear or branched alkyl group having 1 to 20 carbon atoms, in which one methylene group or two or more non-adjacent methylene groups each may be substituted by —O—, —S—, —CO—, —CO—O—, —O—CO—, —CH=CH—, or —C≡C—, one or two or more methylene groups each may be substituted by an arylene group or a divalent heterocyclic group, and a hydrogen atom in the alkyl group may be substituted by a fluorine atom, a diphenylamino group, a triphenylsilyl group, an aryl group, and a heterocyclic group.

A fluorene compound represented by the following general formula (5):

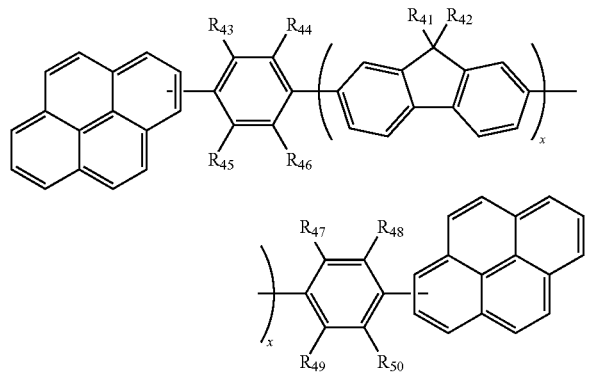

(5)

wherein:

$R_{41}$ to $R_{50}$ are each independently selected from the group consisting of a hydrogen atom, a halogen atom, and a linear or branched alkyl group having 1 to 20 carbon atoms provided that at least one of $R_{43}$ to $R_{50}$ represents a linear or branched alkyl group having 1 to 20 carbon atoms when a pyrenyl group has no substituent;

x represents an integer of 1 to 20; and the pyrenyl group may have substituents, and the substituents are each independently selected from the group consisting of a halogen atom, a linear or branched alkyl group having 1 to 20 carbon atoms, in which one methylene group or two or more non-adjacent methylene groups each may be substituted by —O—, —S—, —CO—, —CO—O—, —O—CO—, —CH=CH—, or —C≡C—, one or two or more methylene groups each may be substituted by an arylene group or a divalent heterocyclic group, and a hydrogen atom in the alkyl group may be substituted by a fluorine atom, a diphenylamino group, a triphenylsilyl group, an aryl group, and a heterocyclic group.

A fluorene compound represented by the following general formula (6):

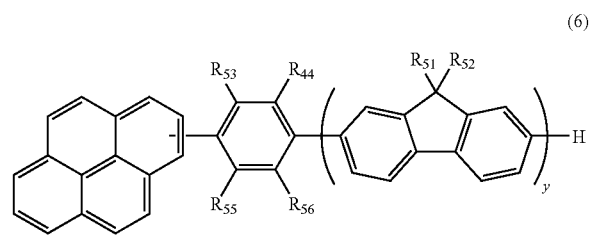

(6)

wherein:

$R_{51}$ to $R_{56}$ are each independently selected from the group consisting of a hydrogen atom, a halogen atom, and a linear or branched alkyl group having 1 to 20 carbon atoms;

y represents an integer of 1 to 20; and a pyrenyl group may have substituents, and the substituents are each independently selected from the group consisting of a halogen atom, a linear or branched alkyl group having 1 to 20 carbon atoms, in which one methylene group or two or more non-adjacent methylene groups each may be substituted by —O—, —S—, —CO—, —CO—O—, —O—CO—, —CH=CH—, or —C≡C—, one or two or more methylene groups each may be substituted by an arylene group or a divalent heterocyclic group, and a hydrogen atom in the alkyl group may be substituted by a fluorine atom, a diphenylamino group, a triphenylsilyl group, an aryl group, and a heterocyclic group.

A fluorene compound represented by the following general formula (7):

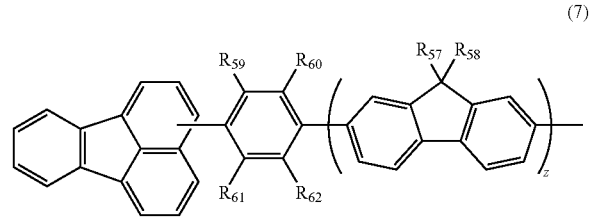

(7)

-continued

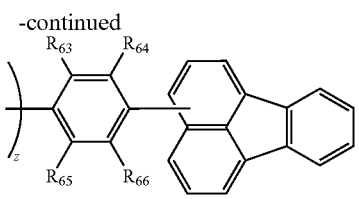

wherein:

$R_{57}$ to $R_{66}$ are each independently selected from the group consisting of a hydrogen atom, a halogen atom, and a linear or branched alkyl group having 1 to 20 carbon atoms;

z represents an integer of 1 to 20; and the fluoranthenyl group may have substituents, and the substituents are each independently selected from the group consisting of a halogen atom, a linear or branched alkyl group having 1 to 20 carbon atoms, in which one methylene group or two or more non-adjacent methylene groups each may be substituted by —O—, —S—, —CO—, —CO—O—, —O—CO—, —CH=CH—, or —C≡C—, one or two or more methylene groups each may be substituted by an arylene group or a divalent heterocyclic group, and a hydrogen atom in the alkyl group may be substituted by a fluorine atom, a diphenylamino group, a triphenylsilyl group, an aryl group, and a heterocyclic group.

A fluorene compound represented by the following general formula (8):

(8)

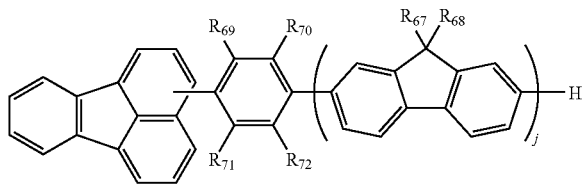

wherein:

$R_{67}$ to $R_{72}$ are each independently selected from the group consisting of a hydrogen atom, a halogen atom, and a linear or branched alkyl group having 1 to 20 carbon atoms;

j represents an integer of 1 to 20; and the fluoranthenyl group may have substituents, and the substituents are each independently selected from the group consisting of a halogen atom, a linear or branched alkyl group having 1 to 20 carbon atoms, in which one methylene group or two or more non-adjacent methylene groups each may be substituted by —O—, —S—, —CO—, —CO—O—, —O—CO—, —CH=CH—, or —C≡C—, one or two or more methylene groups each may be substituted by an arylene group or a divalent heterocyclic group, and a hydrogen atom in the alkyl group may be substituted by a fluorine atom, a diphenylamino group, a triphenylsilyl group, an aryl group, and a heterocyclic group.

A fluorene compound represented by the following general formula (9):

(9)

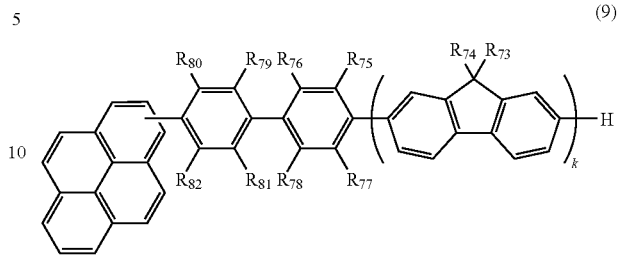

wherein:

$R_{73}$ to $R_{82}$ are each independently selected from the group consisting of a hydrogen atom, a halogen atom, and a linear or branched alkyl group having 1 to 20 carbon atoms;

k represents an integer of 1 to 20; and the pyrenyl group may have substituents, and the substituents are each independently selected from the group consisting of a halogen atom, a linear or branched alkyl group having 1 to 20 carbon atoms, in which one methylene group or two or more non-adjacent methylene groups each may be substituted by —O—, —S—, —CO—, —CO—O—, —O—CO—, —CH=CH—, or —C≡C—, one or two or more methylene groups each may be substituted by an arylene group or a divalent heterocyclic group, and a hydrogen atom in the alkyl group may be substituted by a fluorine atom, a diphenylamino group, a triphenylsilyl group, an aryl group, and a heterocyclic group.

A light emitting device of the present invention using the fluorene compound of the present invention, in particular, a light emitting device of the present invention using the compound as a host for a light emitting layer is an excellent device because the device can not only emit light with high efficiency but also maintain high luminance for a longer time period than that of a compound conventionally used. In addition, the device shows a larger current value than that of a conventional device at the same voltage value, and hence can be expected to be driven at a low voltage.

BEST MODE FOR CARRYING OUT THE INVENTION

Figure 1A:
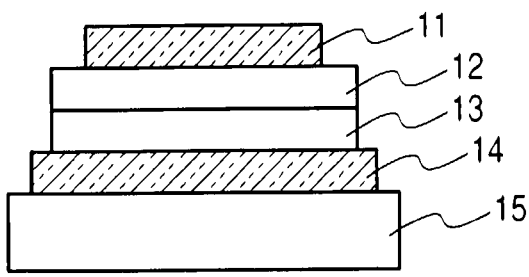
FIGS. 1A, 1B, and 1C are views each showing an example of a light emitting device of the present invention.

First, a fluorene compound of the present invention will be described.

When a light emitting layer is composed of a host material and a guest each having carrier transport property, light emission mainly involves the following several processes:

1. the transport of an electron or a hole in the light emitting layer;
2. the generation of an exciton of the host;
3. the transfer of excitation energy between host molecules; and
4. the transfer of excitation energy from the host to the guest.

Desired energy transfer or light emission in each process occurs in competition with various deactivation processes.

It goes without saying that an improvement in luminous efficiency of an EL device requests a material itself that is mainly responsible for light emission to have a large light emission quantum efficiency. However, how efficiently energy can be transferred between host molecules or between a host and a guest is also of great concern. In addition, no cause for the degradation of light emission due to energization has been revealed at present. However, the degradation is assumed to be related to at least the material itself that is mainly responsible for light emission or a change in environment surrounding the luminescent material due to a molecule around the material.

In view of the foregoing, the inventors of the present invention have made various studies, and have found the following by using a fluorene compound represented by any one of the general formulae (1) to (8) in a charge transport layer or light emitting layer of an organic EL device, or preferably by using the compound as a host or guest for the light emitting layer. That is, the inventors have found that, when the compound is used, the device emits light with high efficiency, maintains high luminance for a long time period, and shows small degradation of light emission due to energization.

The mobility of the host for the light emitting layer is an example of the causes for the degradation of light emission due to energization. When the shape of a molecule of the light emitting layer is such that the degree to which the conjugate surfaces of molecules overlap each other is small, the mobility reduces, and the voltage at which the device is driven increases. In addition, the foregoing may cause a reduction in injection property. From this viewpoint, it is probably necessary to design molecules in such a manner that there is a skeleton where the molecules overlap each other. However, the site where the molecules overlap each other lengthens a conjugation length. In view of the foregoing, the conjugation length of a site serving as a core must not be significantly shortened.

In view of the overlapping of molecules and a conjugation length, the fluorene compound of the present invention preferably uses a para-phenyl group to connect a site serving as a central skeleton (one or more connected fluorenyl groups) and a site having overlapping (condensed ring structure composed only of hydrocarbon). When a phenyl group does not use to combine a condensed ring skeleton with a fluorenyl group, conjugation spreads and therefore, control of mobility comes to be difficult. In contrast, in the present invention, since a phenyl group is used, control of electron transportability comes to be easy. Accordingly, an optimum charge amount can be controlled in the organic EL device, whereby high ruminance can be maintained for a long time period and small degradation of light emission due to energization can be realized. In this case, however, when the compound has phenyl groups on both of its sides, the number of phenyl groups is two, and the number of condensed ring structures is two, so the molecular weight of the compound is apt to increase. This point adversely affects sublimation property. Accordingly, a phenyl group or a condensed ring structure is preferably present only on one side, though phenyl groups or condensed ring structures may be present on both sides. When phenyl groups are present on both sides, a condensed ring structure on one side is preferably as simple as naphthalene. In the case of, for example, a pyrenyl group, in order that an intermolecular force may be suppressed to improve sublimation property, the pyrenyl group preferably has a substituent, or, when the pyrenyl group has no substituent, an adjacent phenyl group preferably has a substituent such as a methyl group. In addition, when an alkyl group at 9-position of a fluorenyl group of the central skeleton becomes long, the glass transition temperature and melting point of the compound tend to reduce. Accordingly, the alkyl group at 9-position of the fluorenyl group is preferably a methyl group, but a long-chain alkyl group such as an ethyl group, a propyl group, and a butyl group is also permitted. In addition, the chain lengths of 9-positions of the respective fluorenyl groups are preferably identical to each other from the viewpoint of synthesis, but may be different from each other. In addition, the substituent of the phenyl group is preferably a hydrogen atom from the viewpoint of conductivity, but an alkyl group such as a methyl group and an ethyl group is also permitted from the viewpoints of a conjugation length and crystallinity.

In addition, a guest molecule must have a skeleton having a high quantum efficiency, and a skeleton having a high quantum efficiency must be introduced into a condensed ring portion. On the basis of those points, when the compound of the present invention is used in the light emitting layer of a fluorescent light emitting device, the compound can be used as each of a host material and a guest material each having a color ranging from a blue color to a red color, or mainly from a blue color to a green color because the compound has a condensed ring structure. A light emitting device having high efficiency can be realized by using, in a condensed ring portion, a skeleton a condensed ring of which is formed of $SP^2$ carbon credited with a high quantum efficiency and high charge transport property such as pyrene, anthracene, fluoranthene, benzofluoranthane, perylene, tetracene, chrysene, or picene. In addition, the device can be similarly realized by using a skeleton such as a fluorenyl group.

In addition, the charge transport property of a molecule can be controlled by: separately using a compound having condensed ring structures of this type on both sides and a compound having a condensed ring structure of this type on one side; adjusting the number of phenyl groups; or introducing a substituent to be possessed by a phenyl group. The adjustment of the number of condensed ring structures or the number of phenyl groups has an effect on the establishment of the carrier balance of a device, so improvements in lifetime and efficiency can be expected from the adjustment.

Further, when the material is used as a host material, the use of a guest material having a condensed ring plus amine skeleton as a luminescent material can provide a combination of the host material having high electron transport property and the guest material having hole transport property. In this case, a charge balance in the light emitting layer can be established, so light emission with high efficiency and a long lifetime can be expected. Of course, even when each of a host and a guest has a skeleton composed only of hydrocarbon, the use of the compound of the present invention can realize high efficiency and a long lifetime.

As described above, the use of the compound of the present invention in a light emitting layer is effective; the use of the compound in an electron transport layer, a hole transport layer, an electron blocking layer, a hole blocking layer, an electron injection layer, or a hole injection layer is also effective.

Hereinafter, specific structural formulae of organic compounds to be used in the present invention are shown below. However, the formulae merely exemplify representative examples, and the present invention is not limited to them.

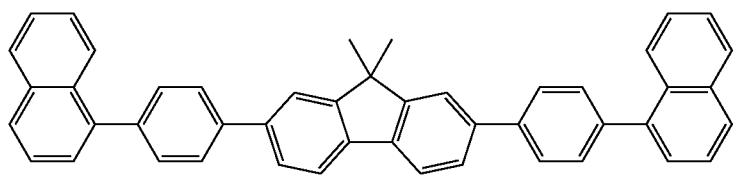
H-1
H-2
H-3
H-4
H-5
H-6
H-7

-continued
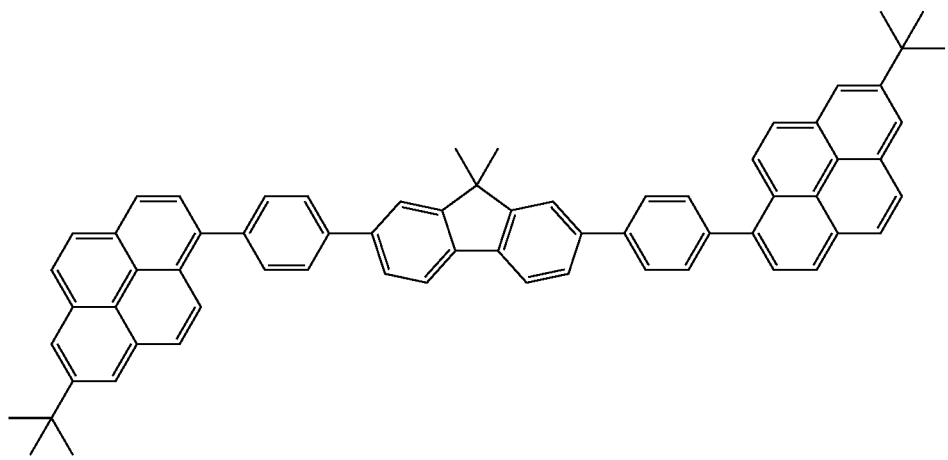
H-8
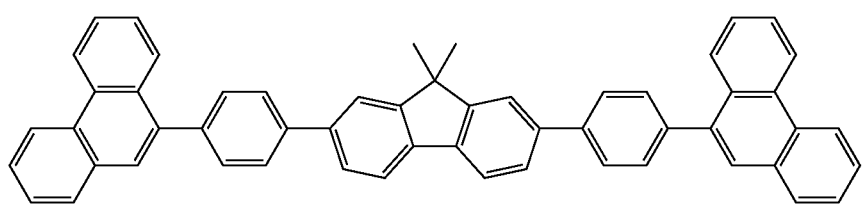
H-9
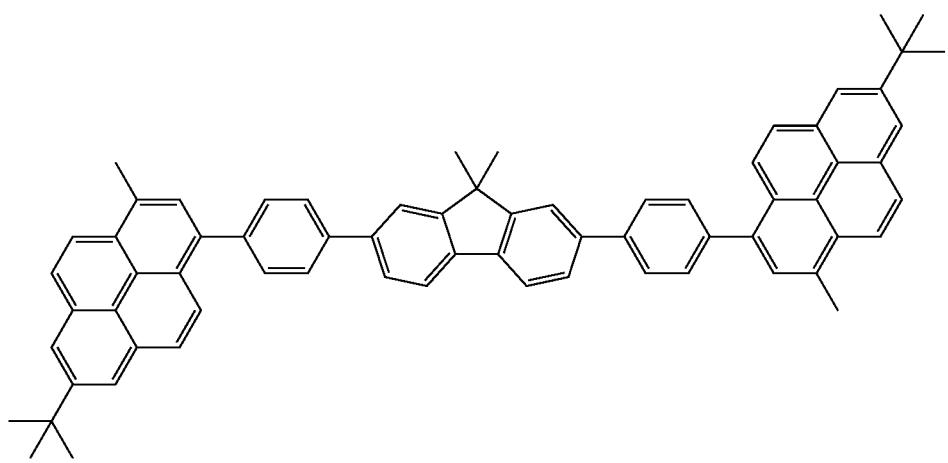
H-10
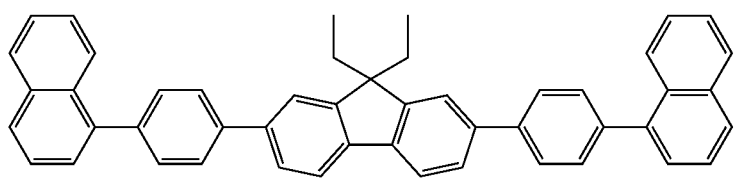
H-11
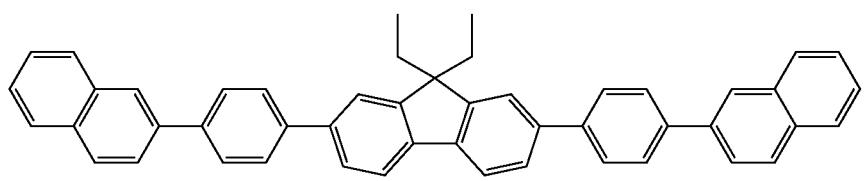
H-12

-continued
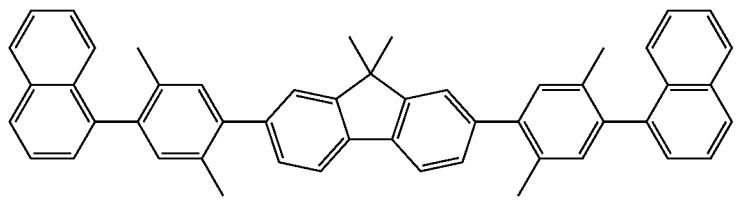
H-13
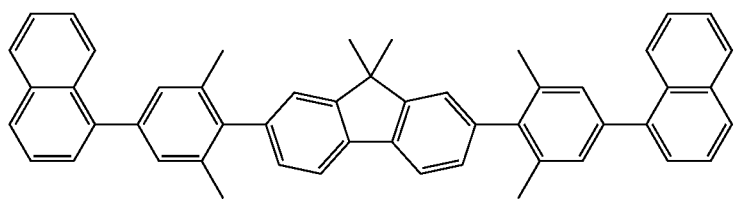
H-14
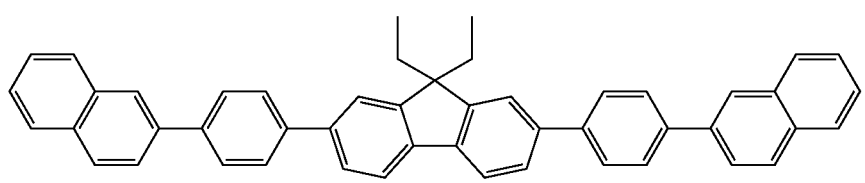
H-15
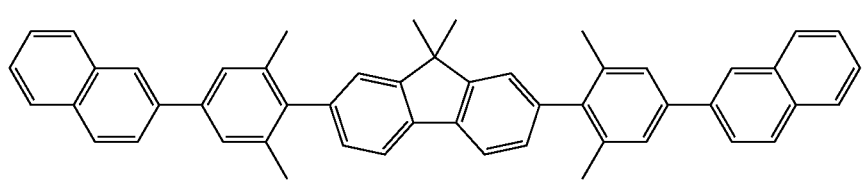
H-16
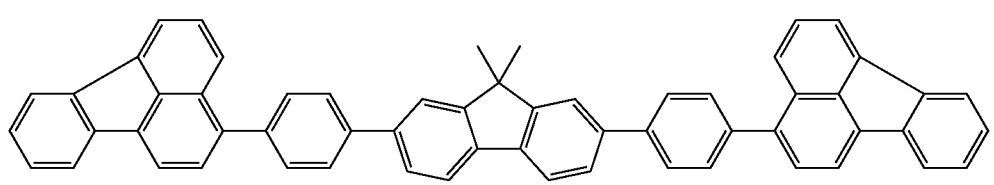
H-17
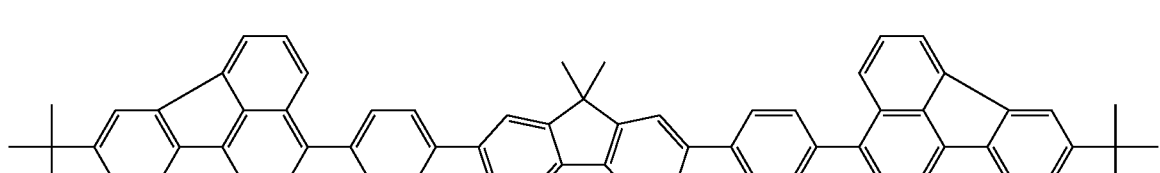
H-18
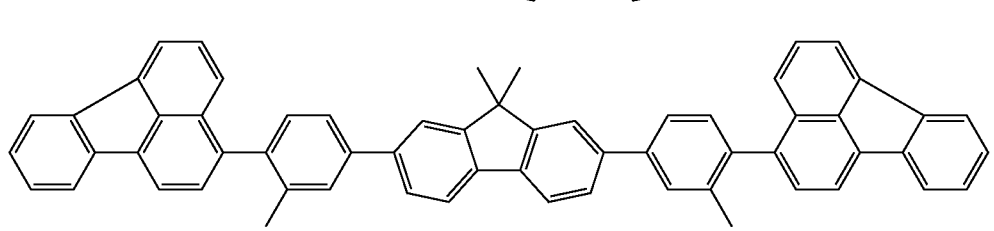
H-19
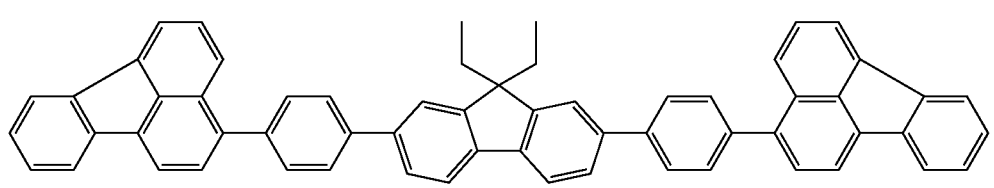
H-20

-continued
H-21
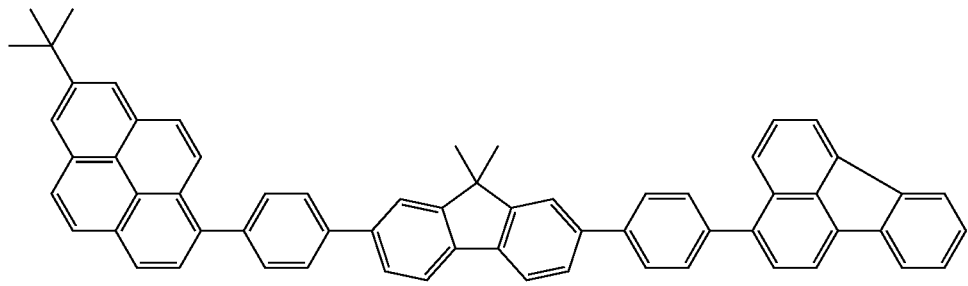
H-22
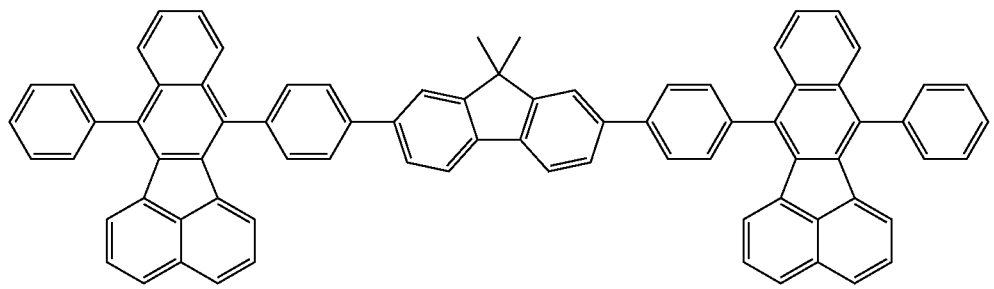
H-23
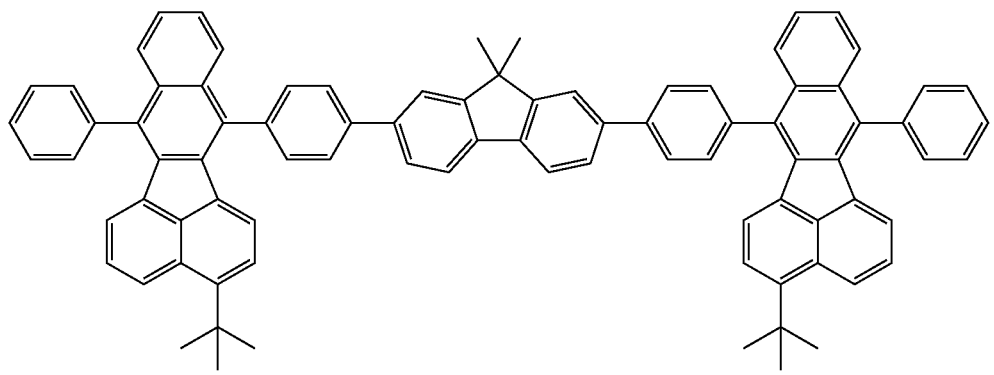
H-24
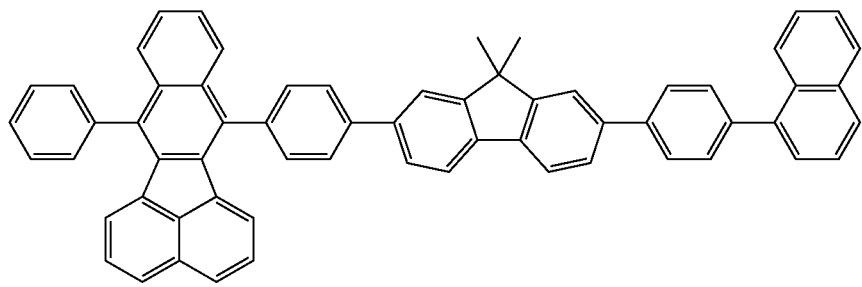
H-25
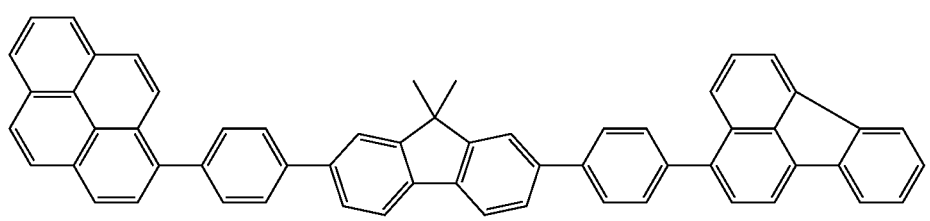

H-26
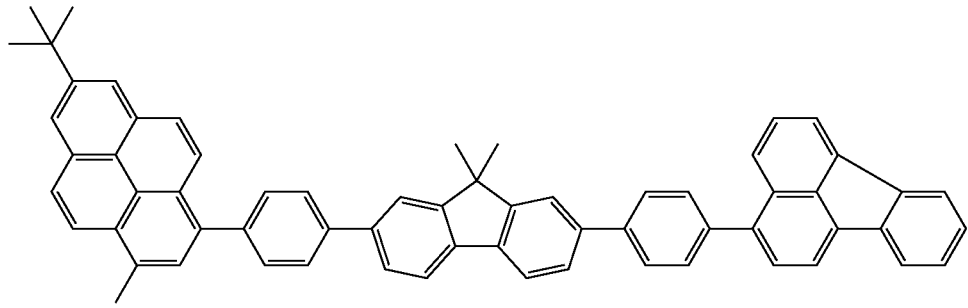
H-27
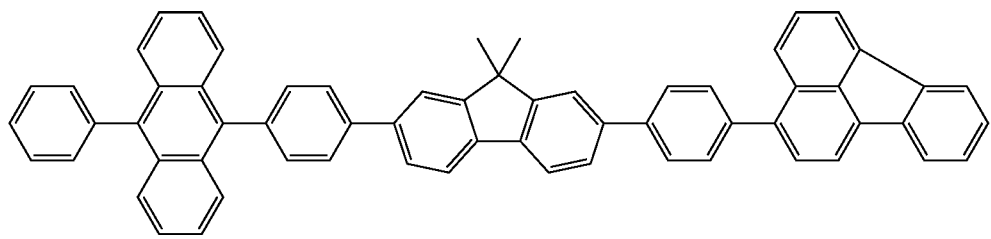
H-28
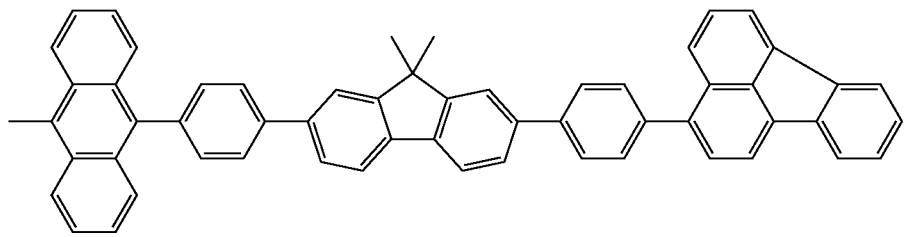
H-29
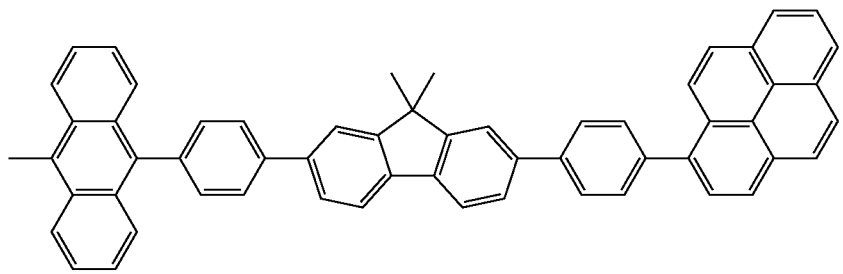
H-30
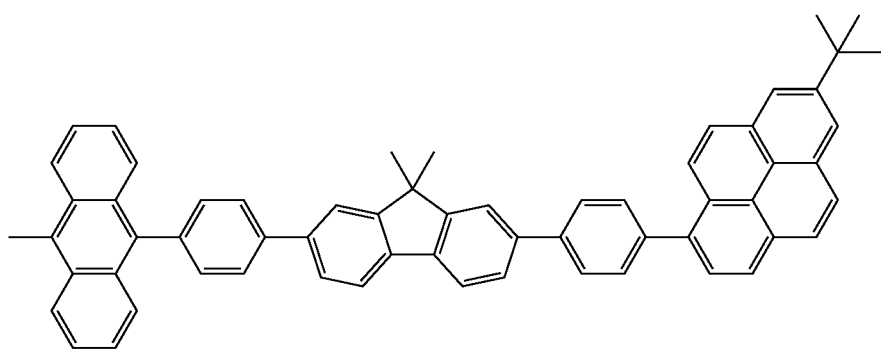
H-31
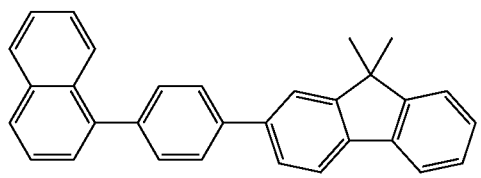
H-32
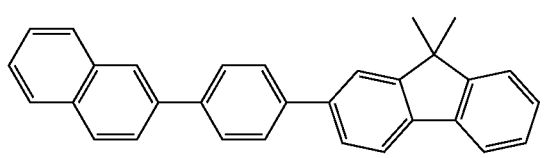

-continued
H-33
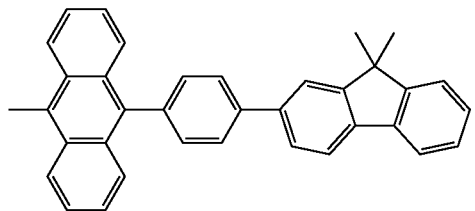
H-34
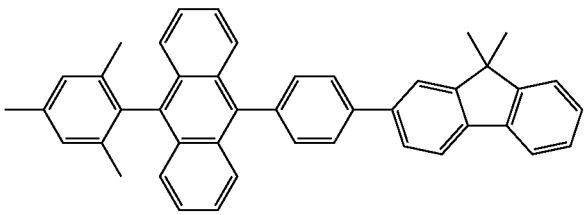
H-35
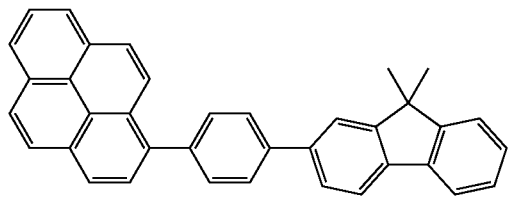
H-36
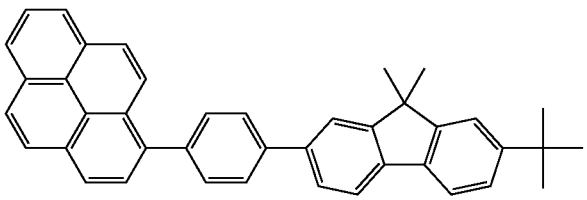
H-37
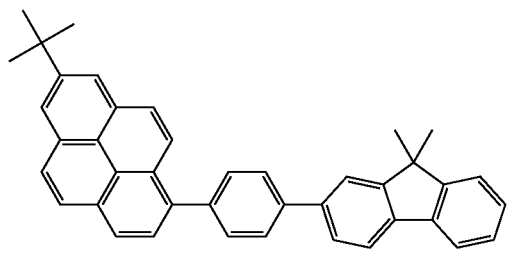
H-38
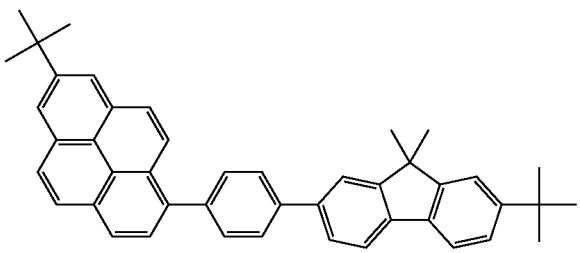
H-39
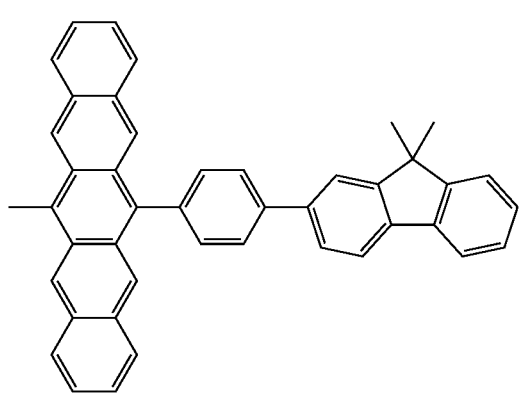
H-40
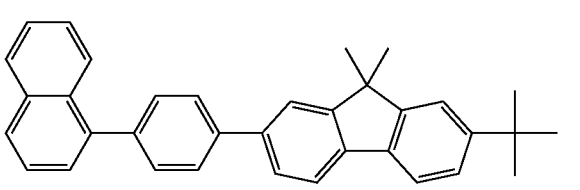
H-41
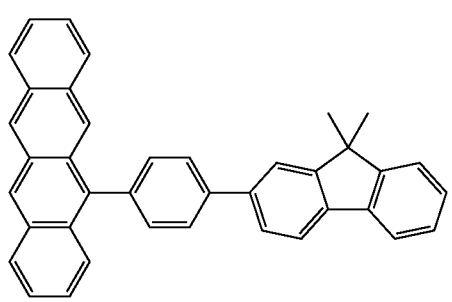
H-42
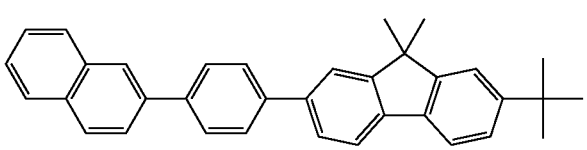
H-43
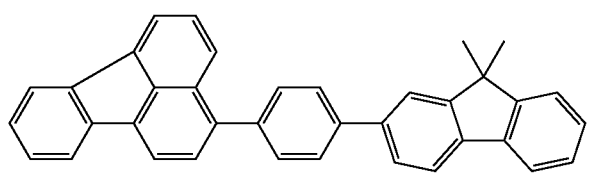
H-44
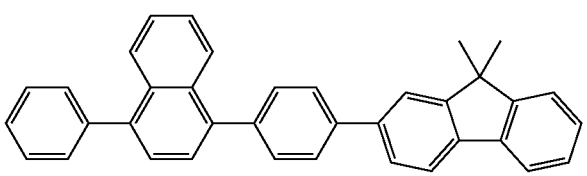

-continued
H-45
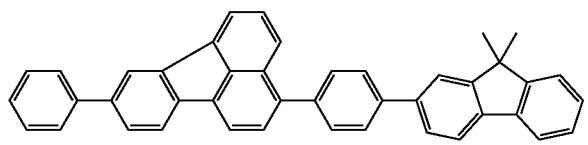
H-46
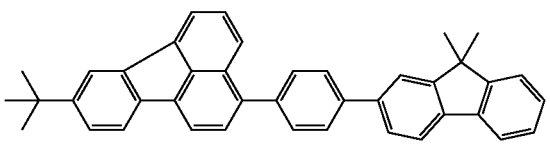
H-47
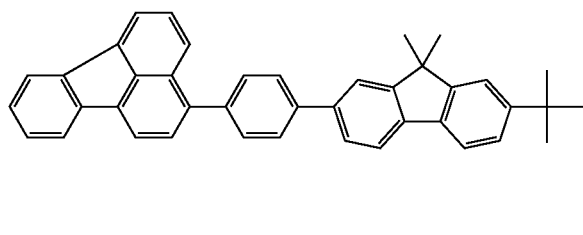
H-48
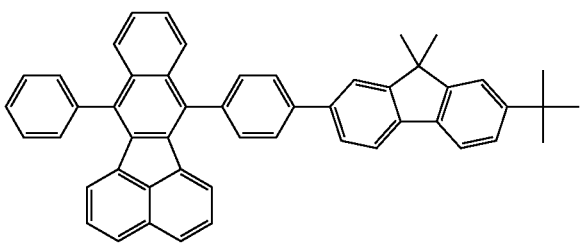
H-49
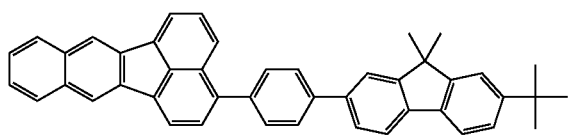
H-50
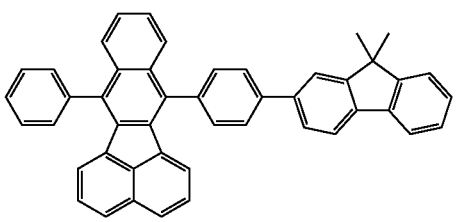
H-51
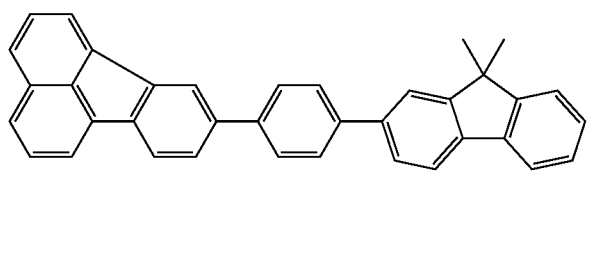
H-52
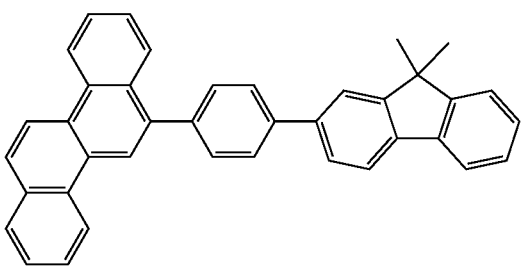
H-53
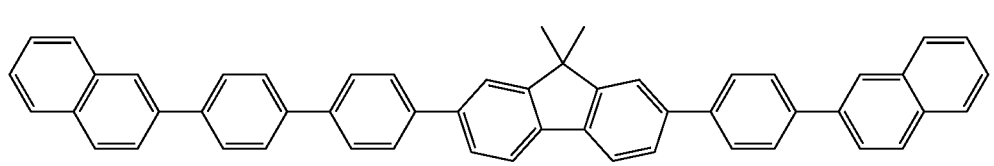
H-54
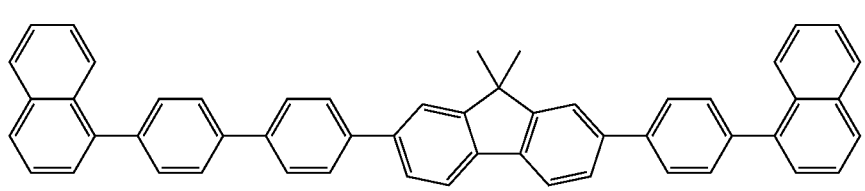
H-55
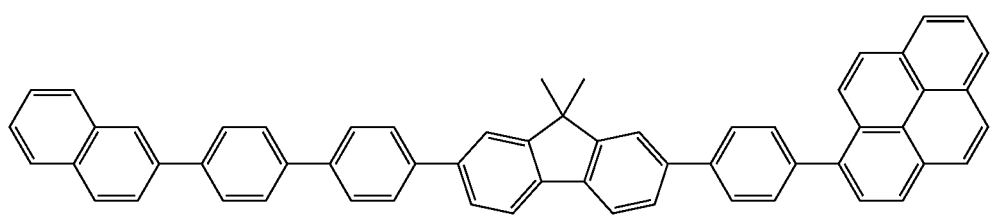

-continued
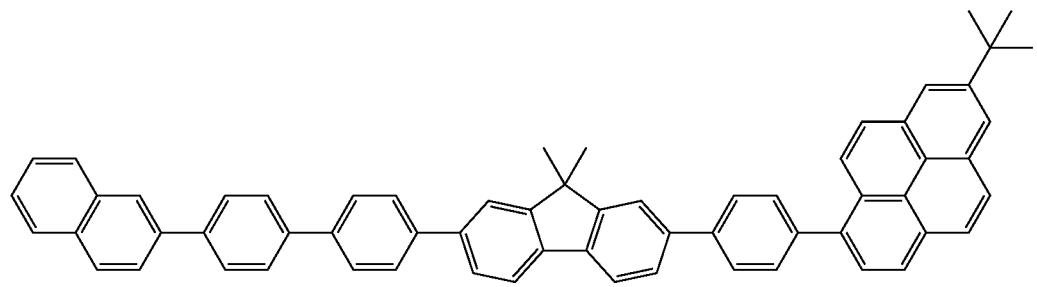
H-56
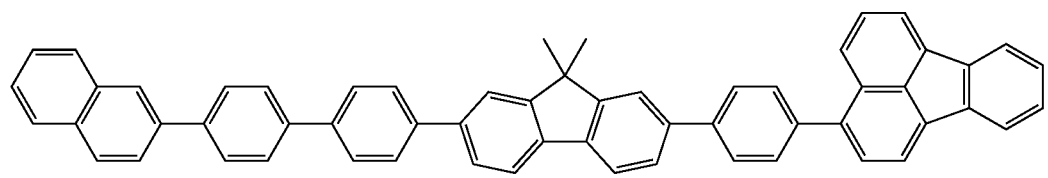
H-57
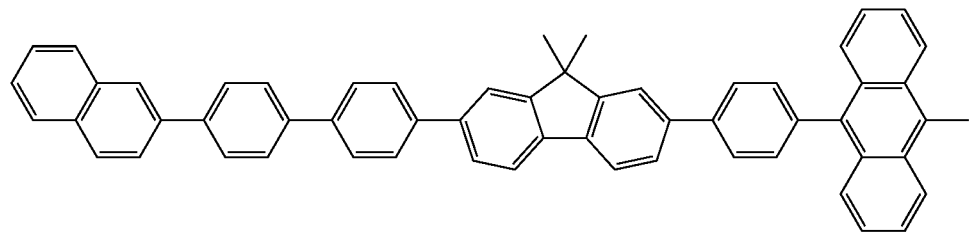
H-58
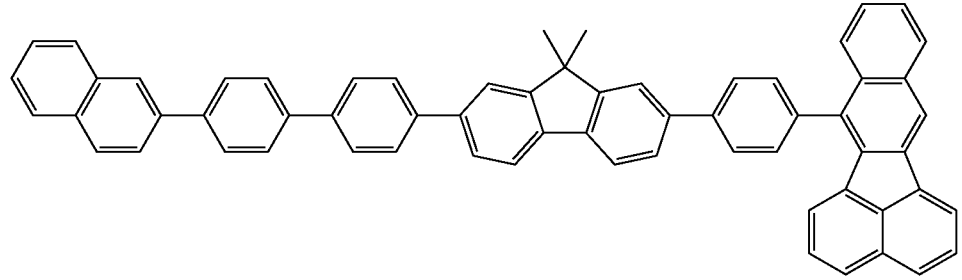
H-59
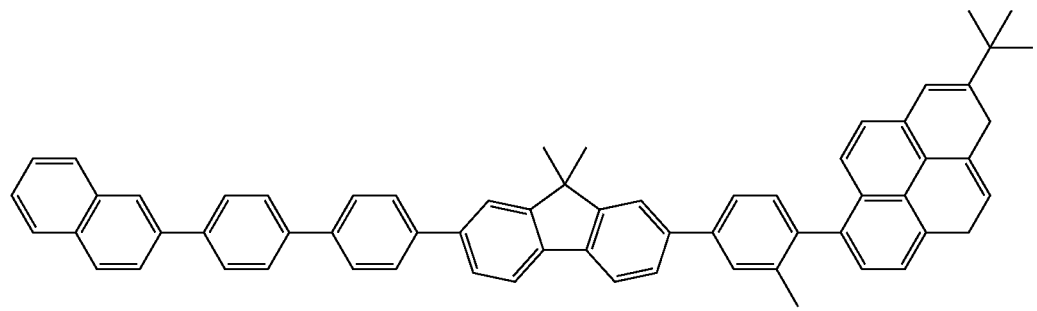
H-60
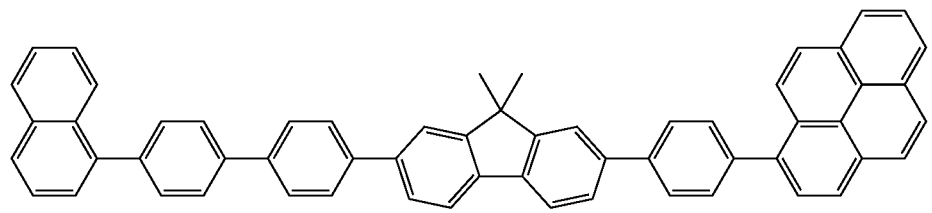
H-61

-continued
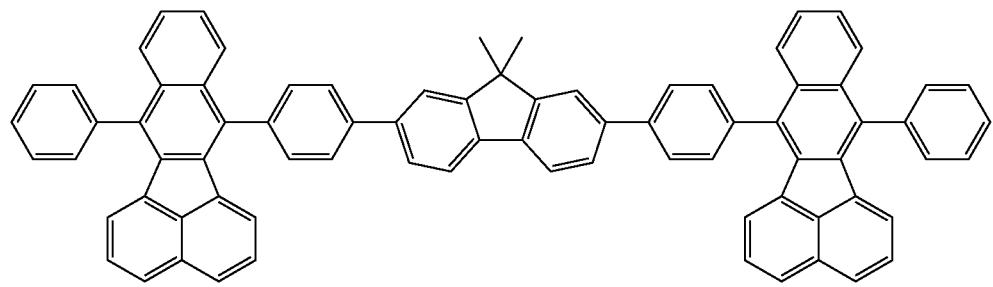
H-62
H-63
H-64
H-65
H-66
H-67
H-68

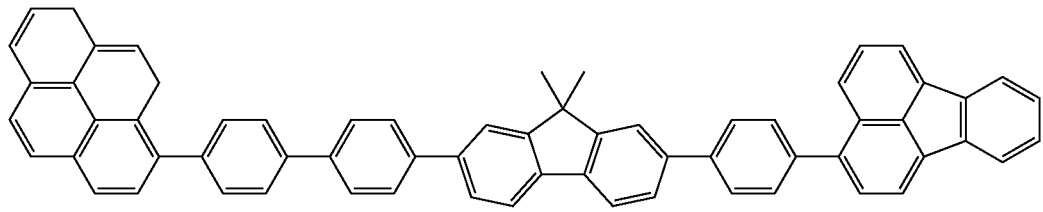
H-69
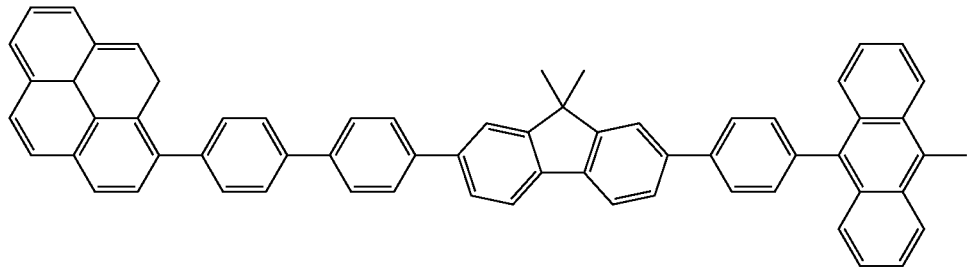
H-70
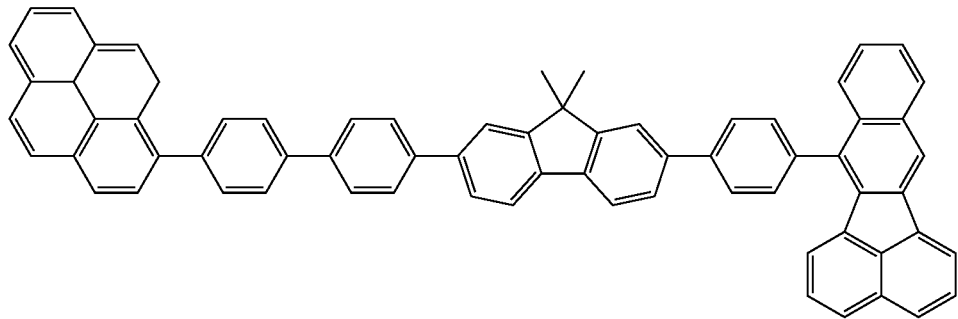
H-71
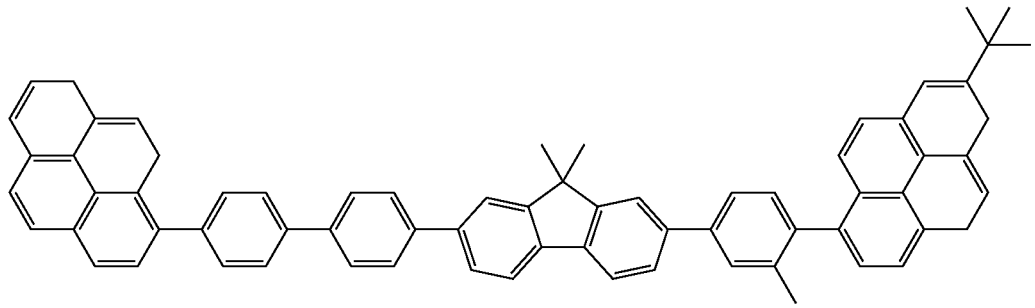
H-72
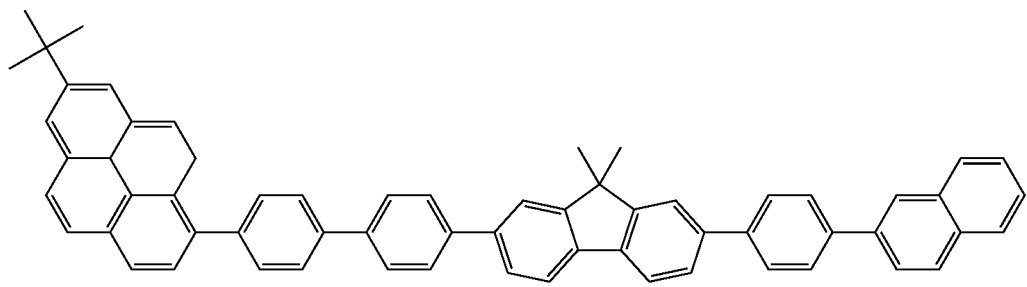
H-73

-continued
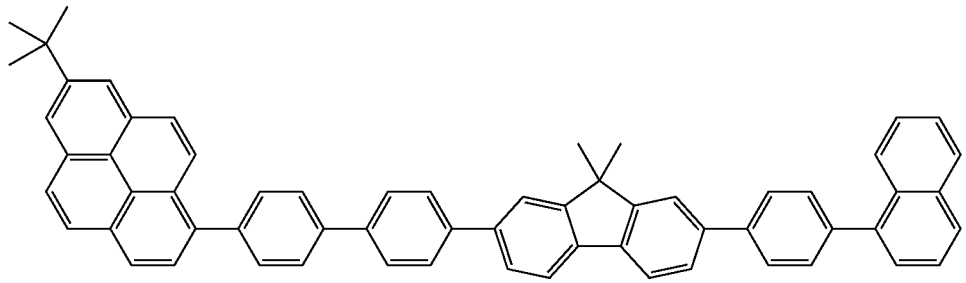
H-74
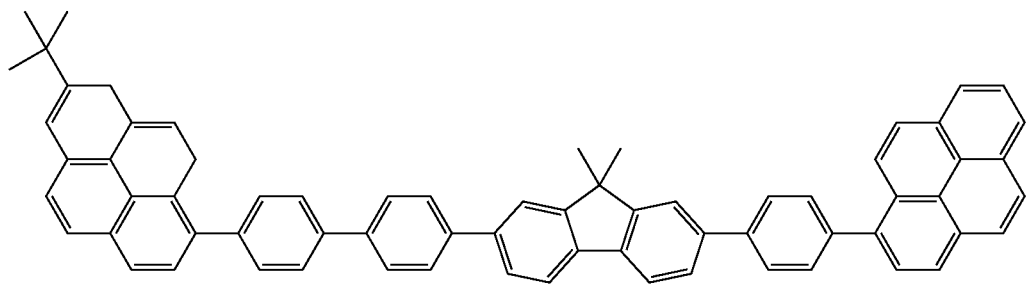
H-75
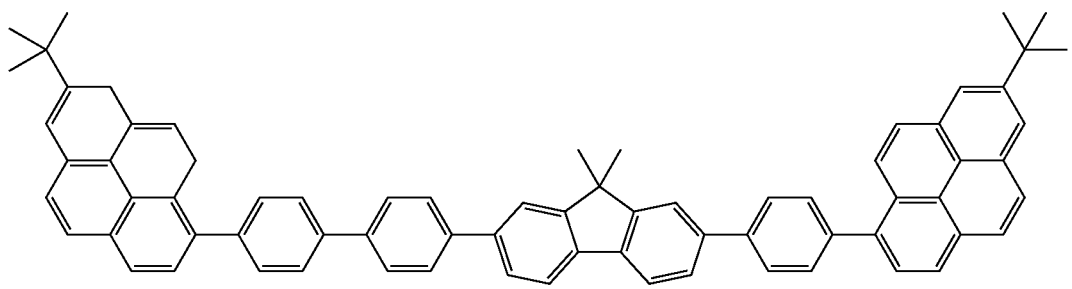
H-76
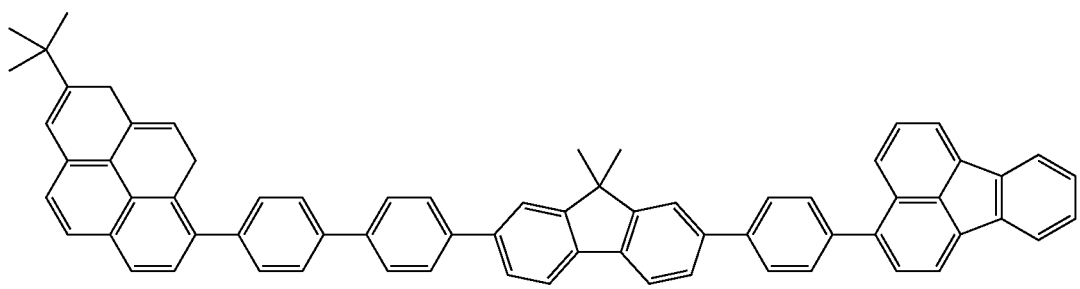
H-77
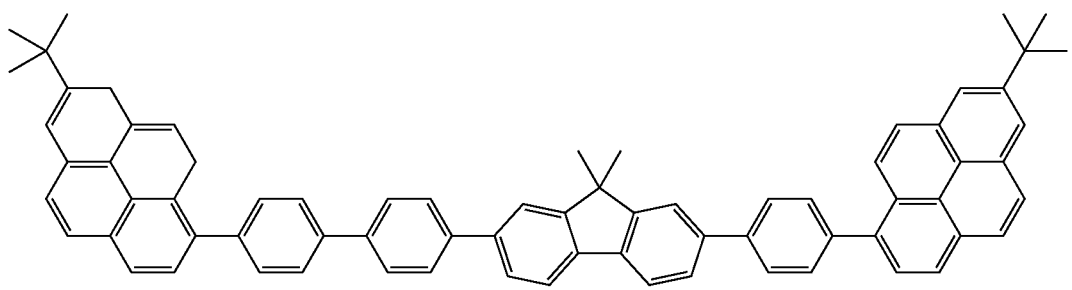
H-78
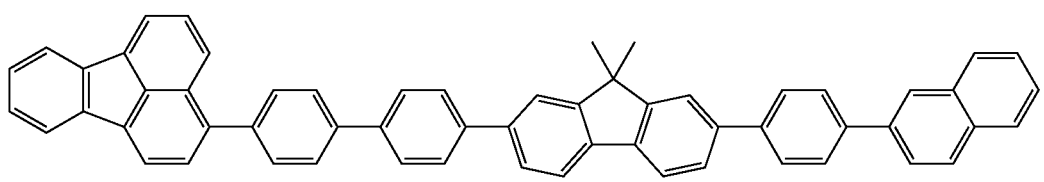
H-79

-continued
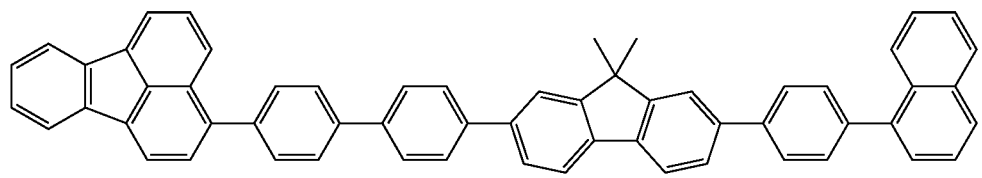
H-80
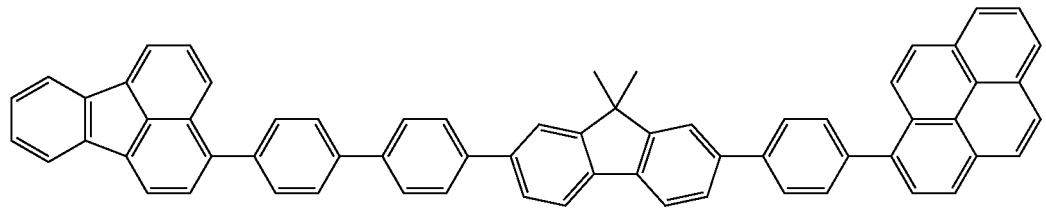
H-81
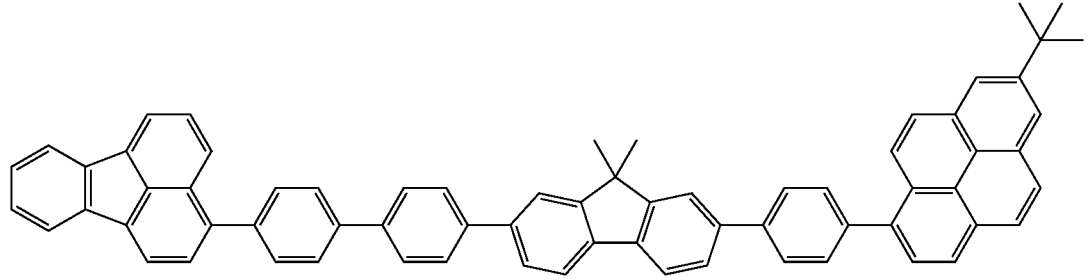
H-82
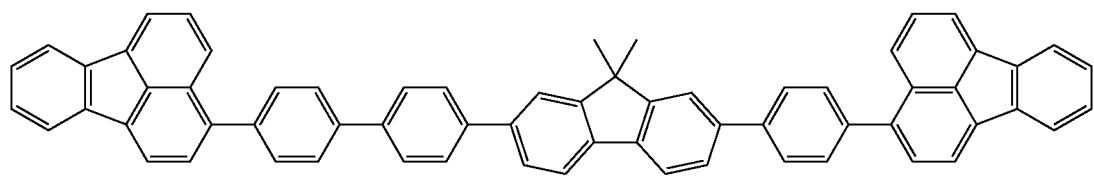
H-83
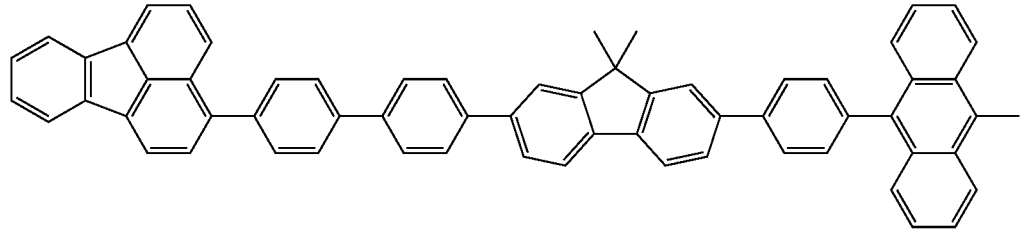
H-84
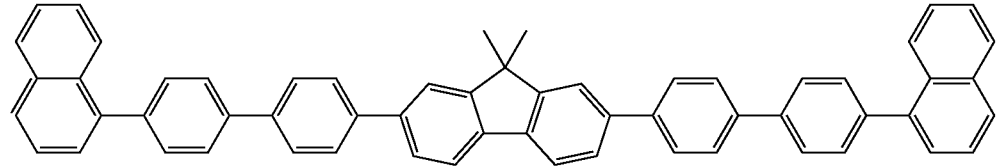
H-85
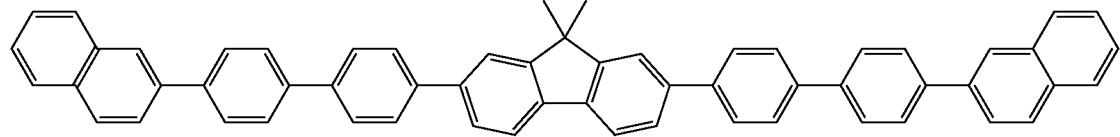
H-86
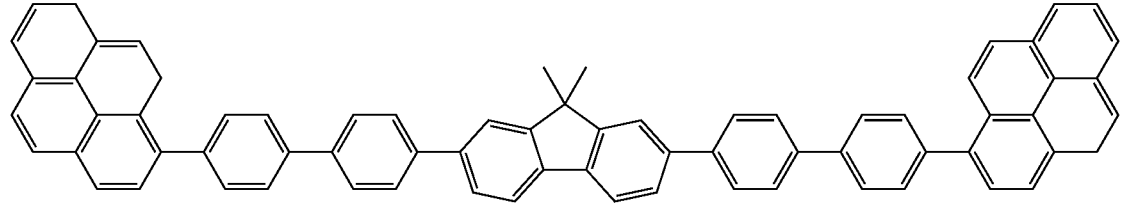
H-87

-continued
H-88
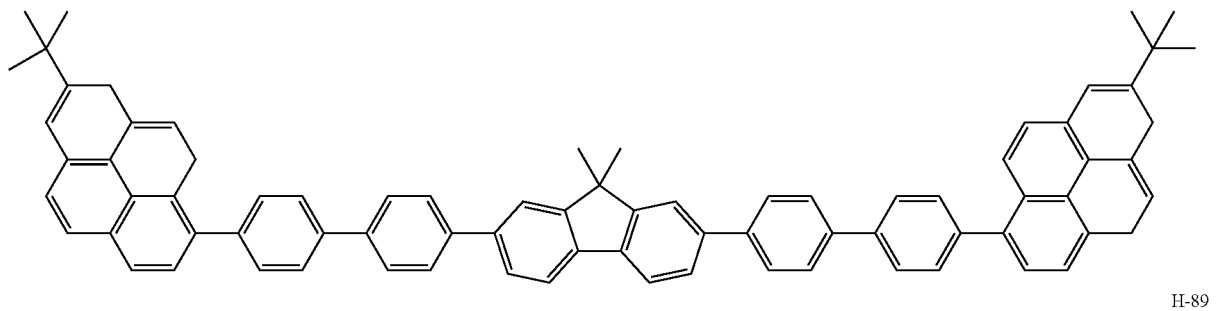
H-89
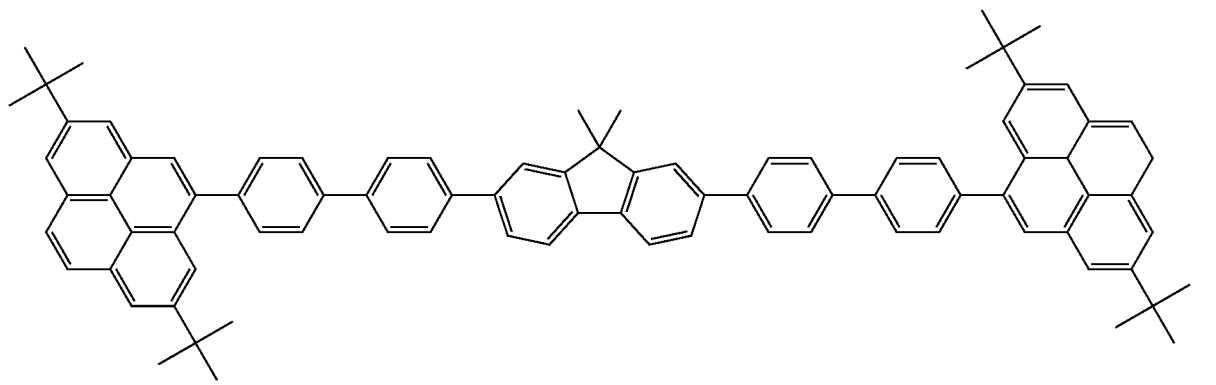
H-90
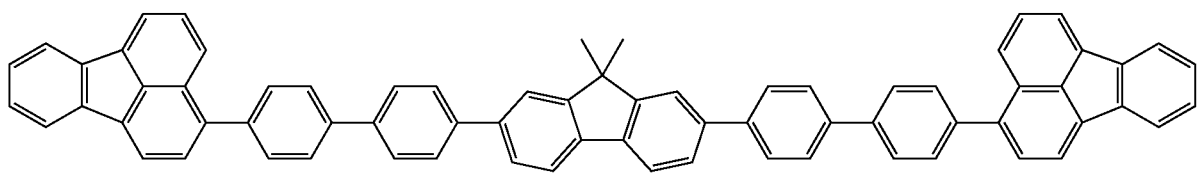
H-91
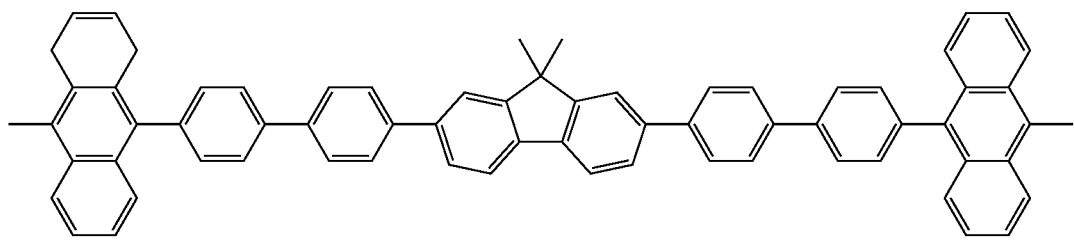
H-92
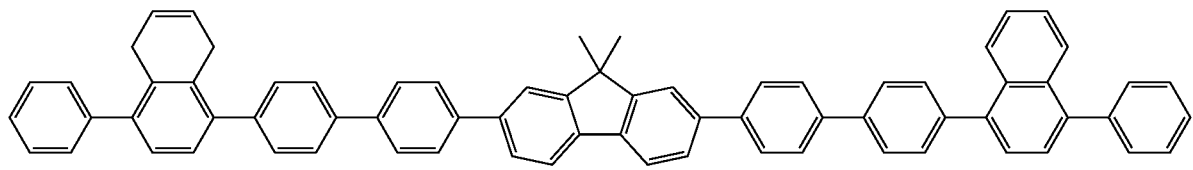
H-93
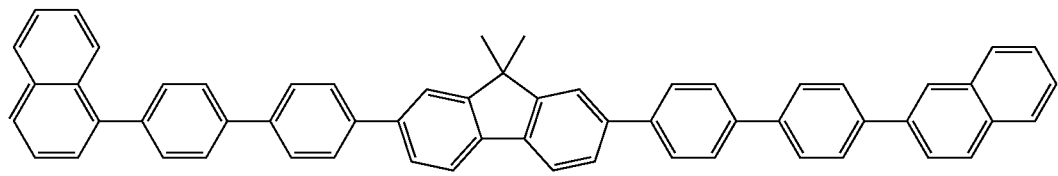

-continued
H-94
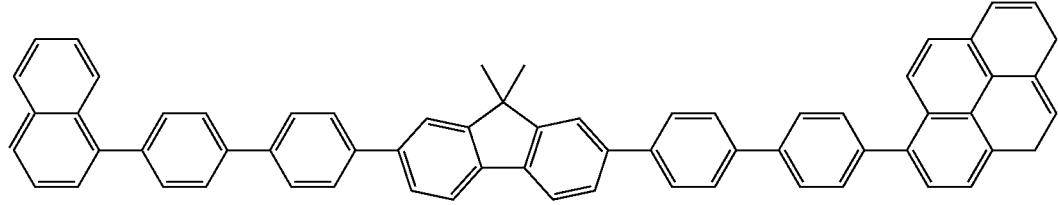
H-95
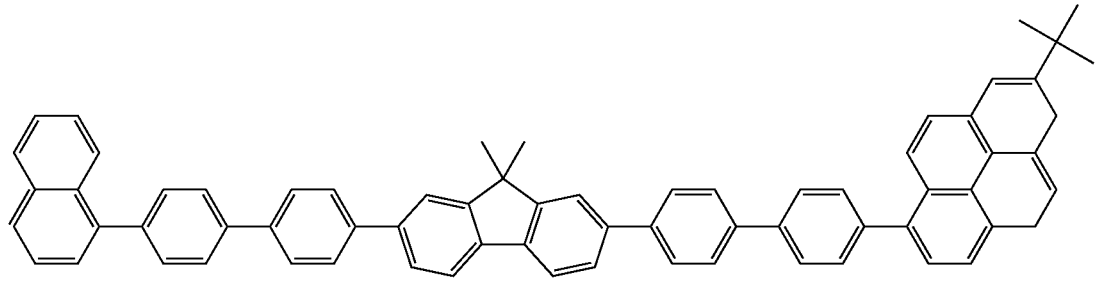
H-96
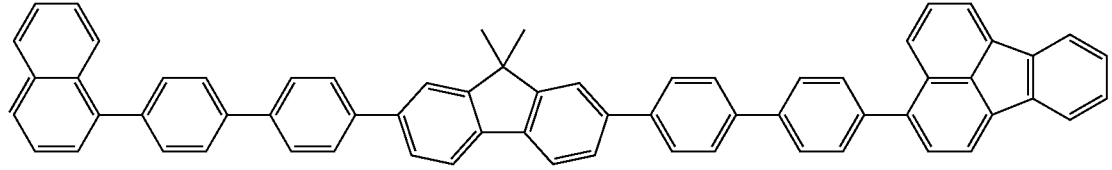
H-97
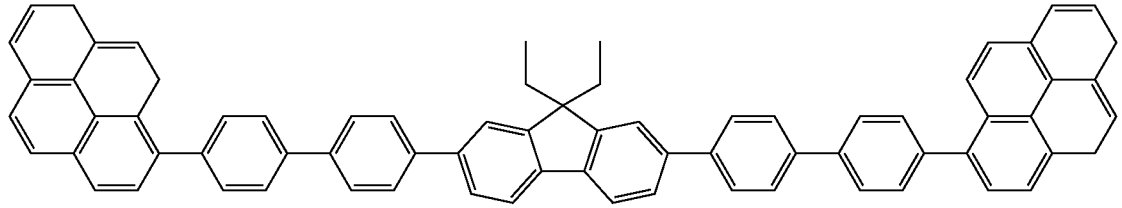
H-98
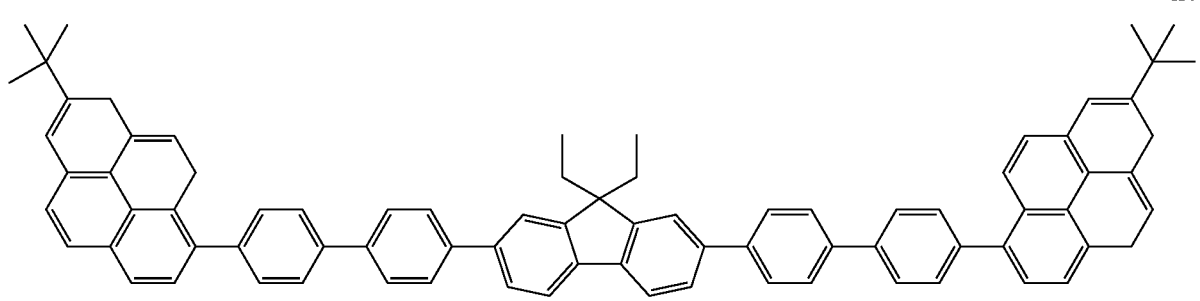
H-99
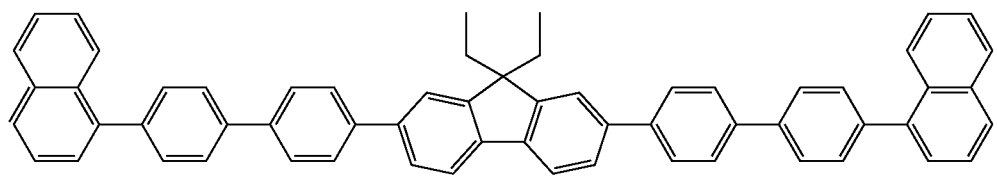
H-100
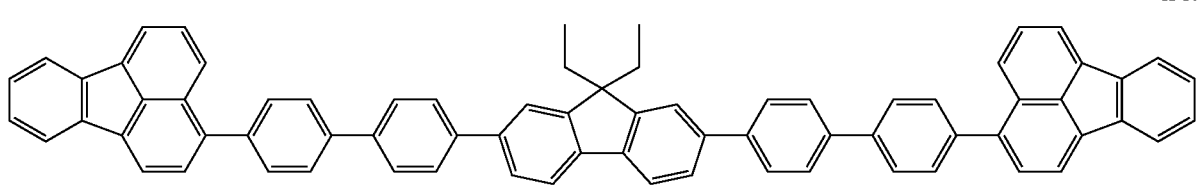

-continued
H-101
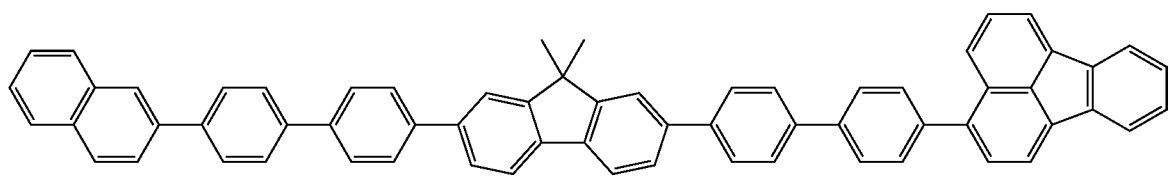
H-102
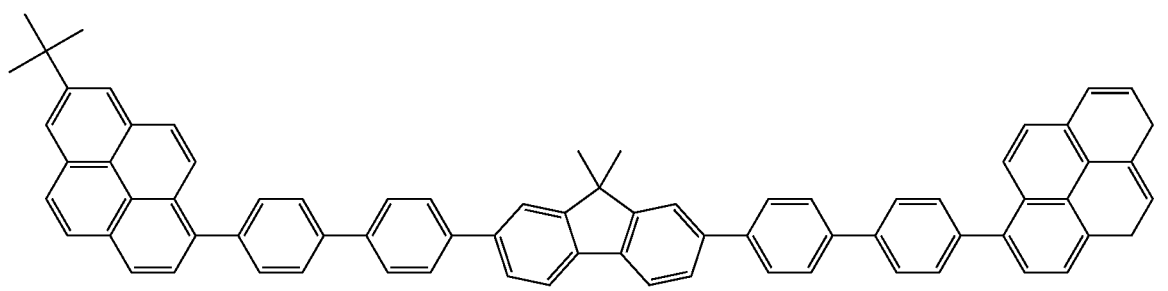
H-103
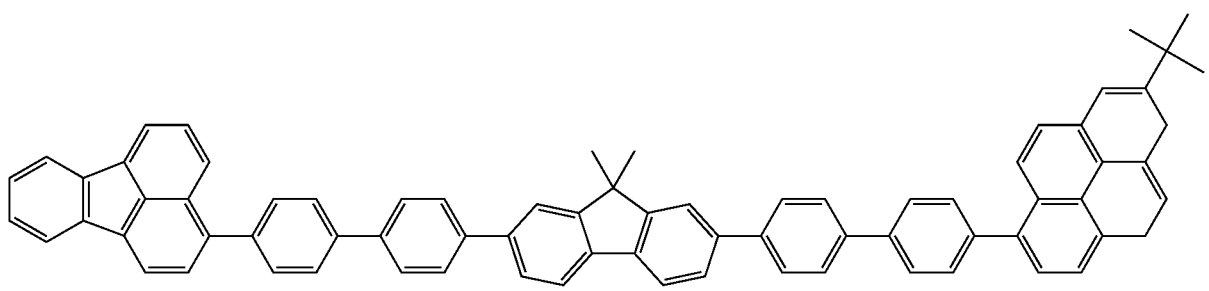
H-104
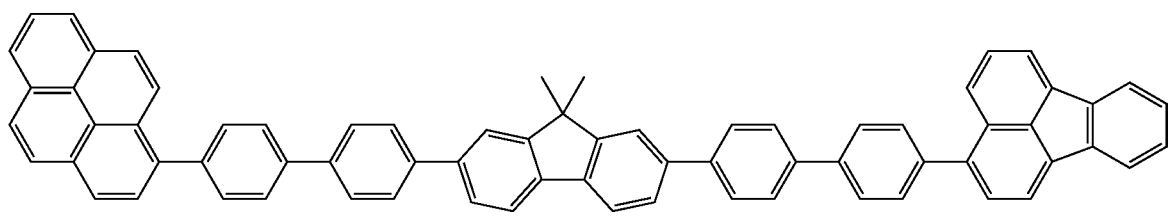
H-105
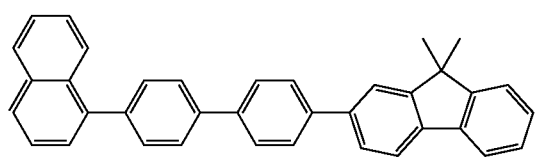
H-106
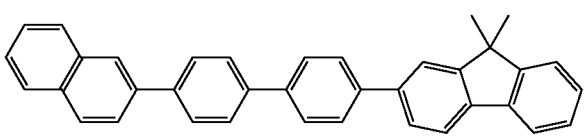
H-107
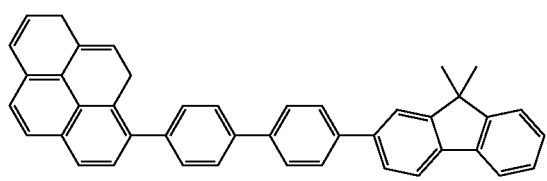
H-108
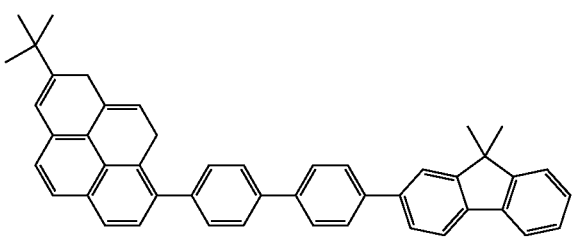

-continued
H-109
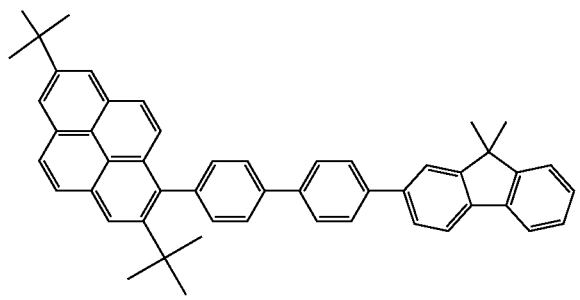
H-110
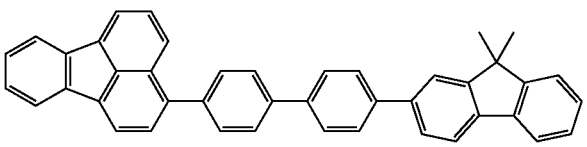
H-111
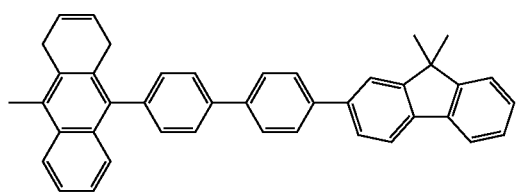
H-112
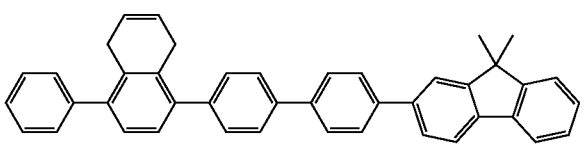
H-113
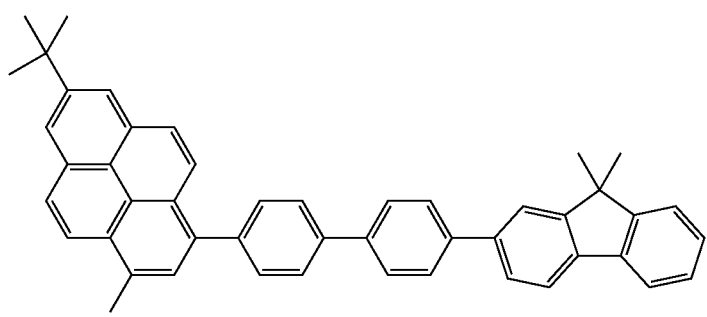
H-114
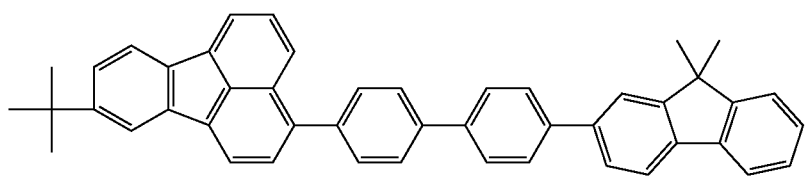
H-115
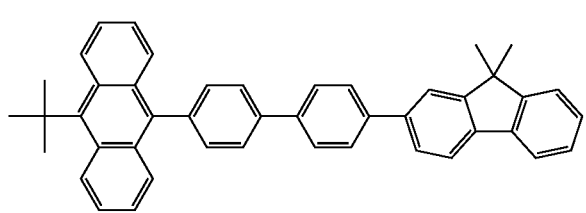
H-116
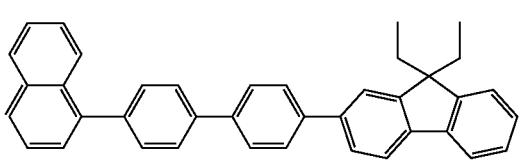
H-117
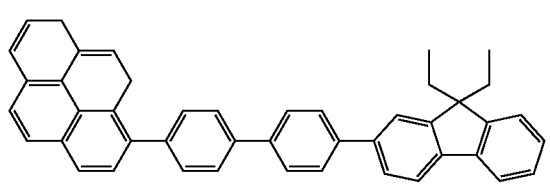
H-118
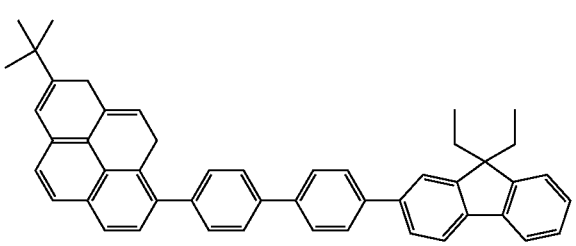

-continued
H-119
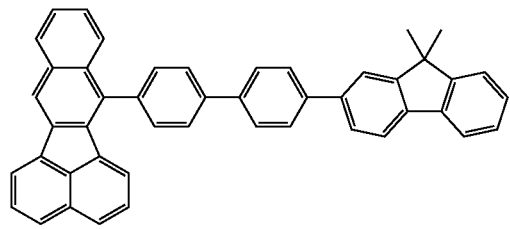
H-120
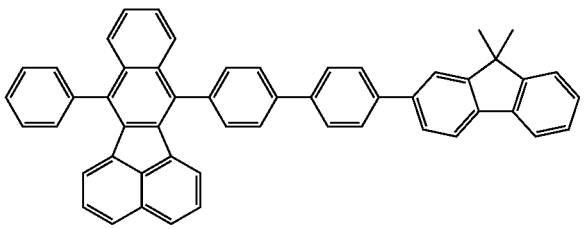
H-121
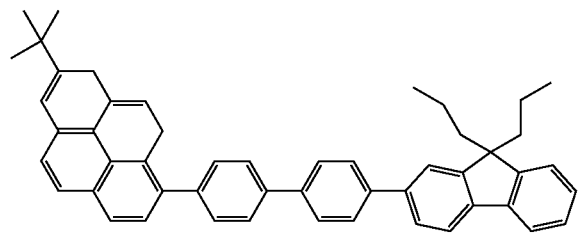
H-122
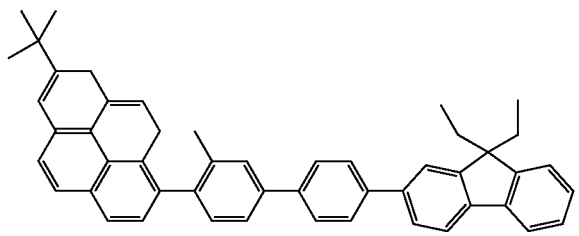
H-123
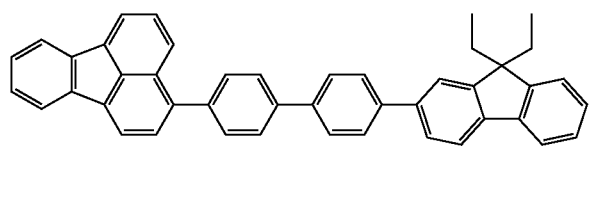
H-124
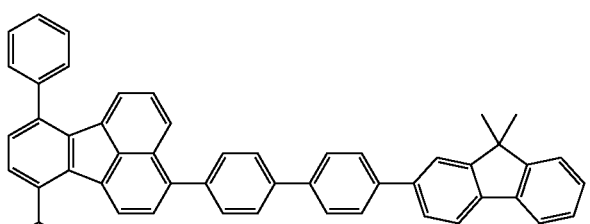
H-125
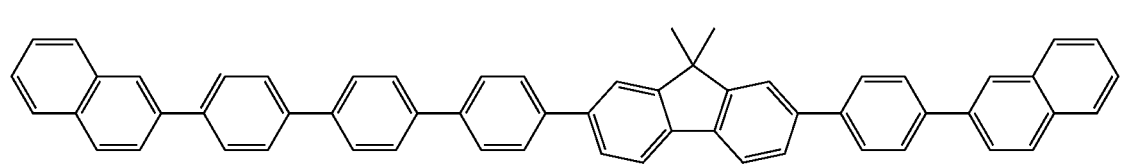
H-126
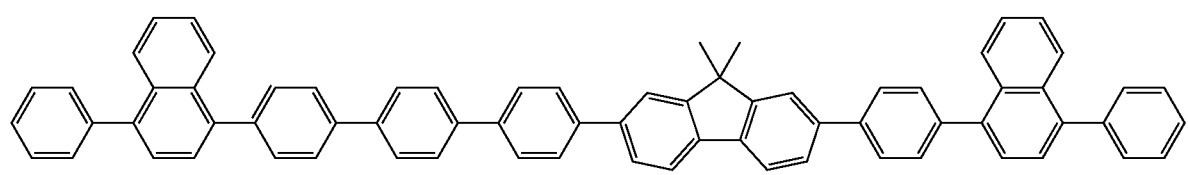
H-127
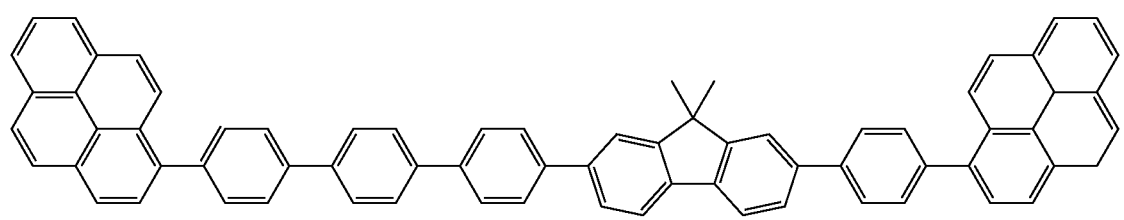
H-128

-continued
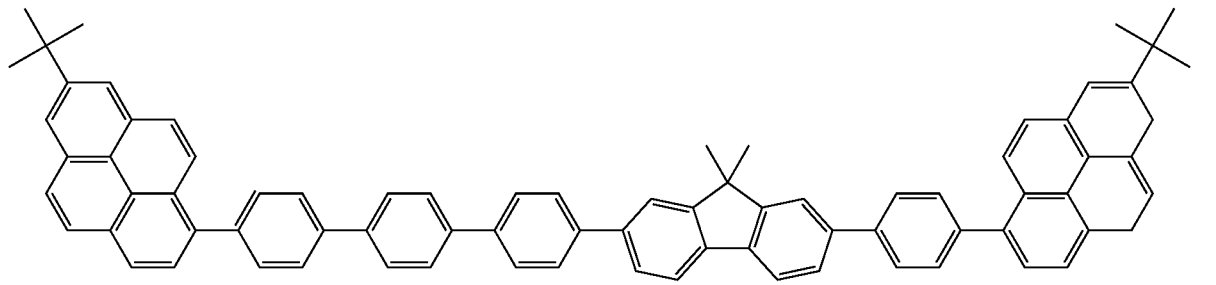
H-129
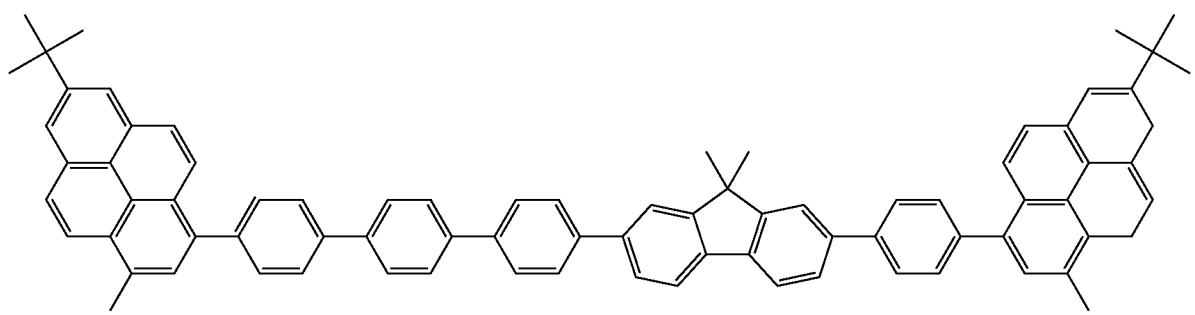
H-130
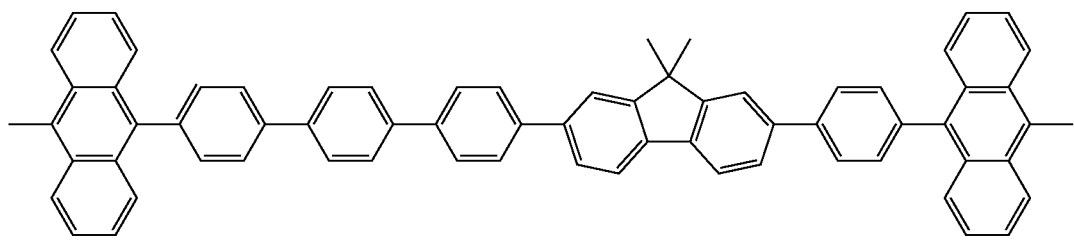
H-131
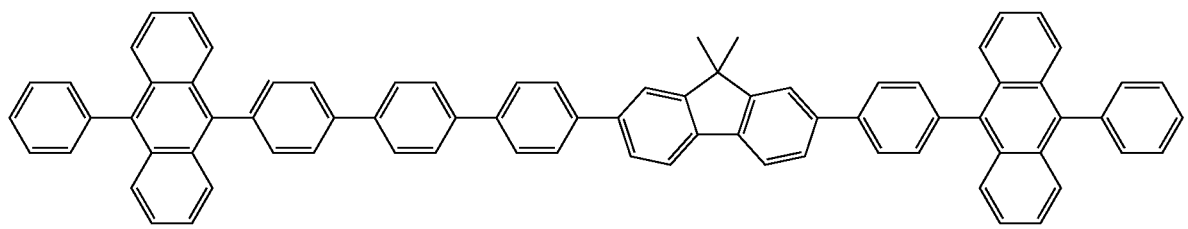
H-132
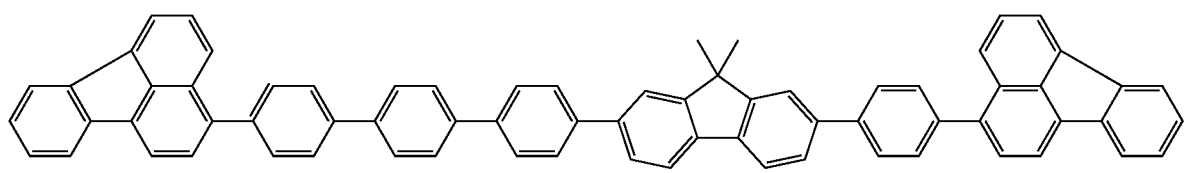
H-133
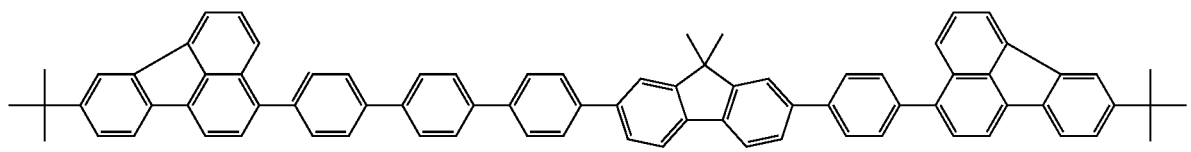
H-134

H-135
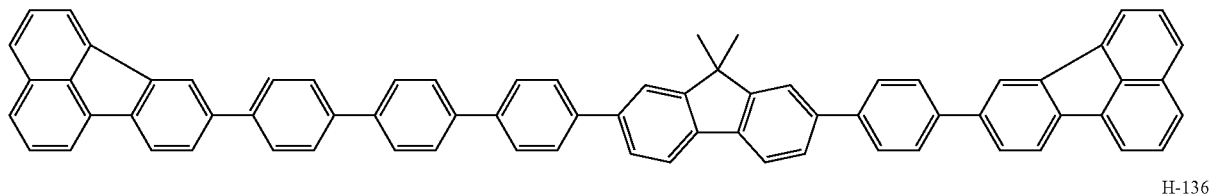
H-136
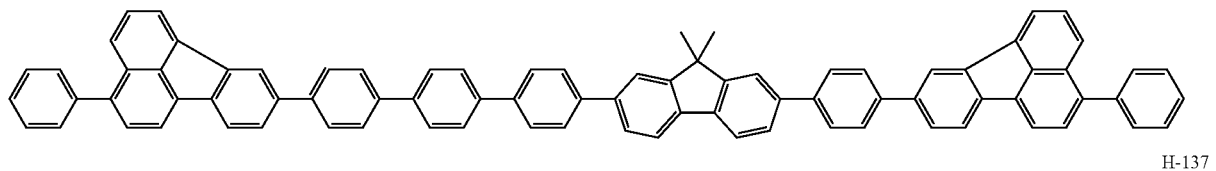
H-137
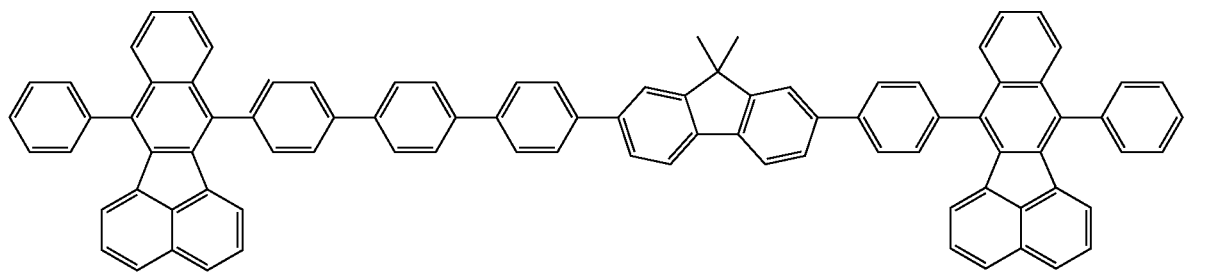
H-138
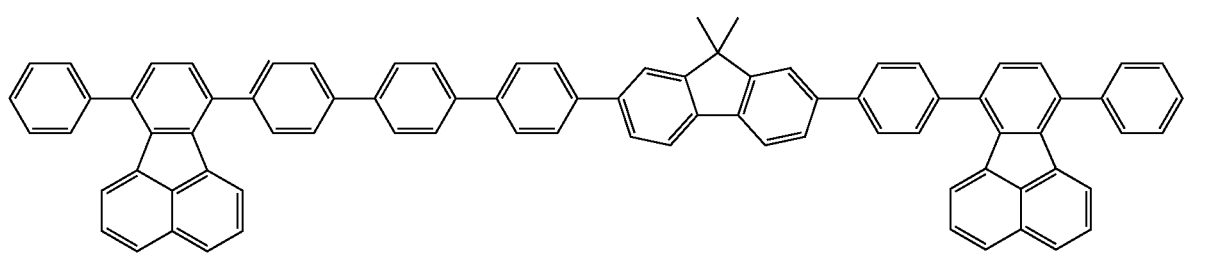
H-139
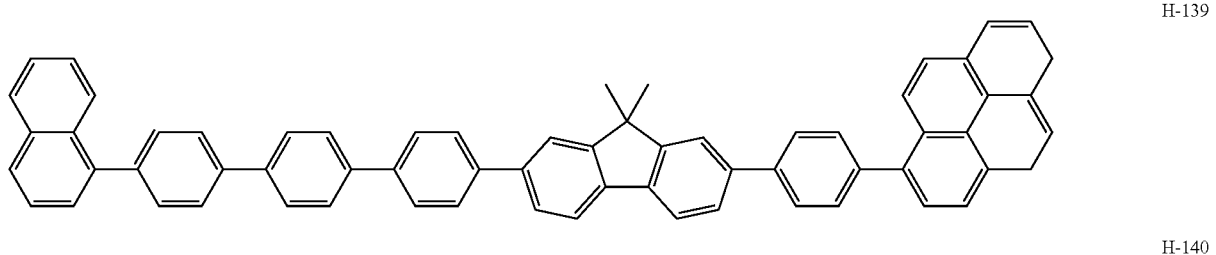
H-140
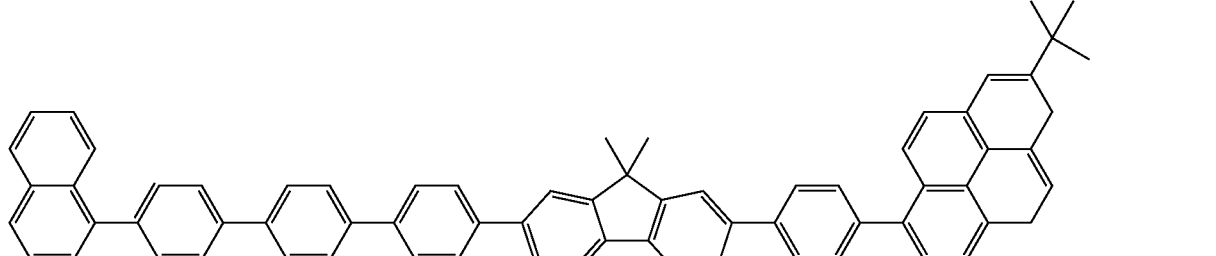
H-141

-continued
H-142
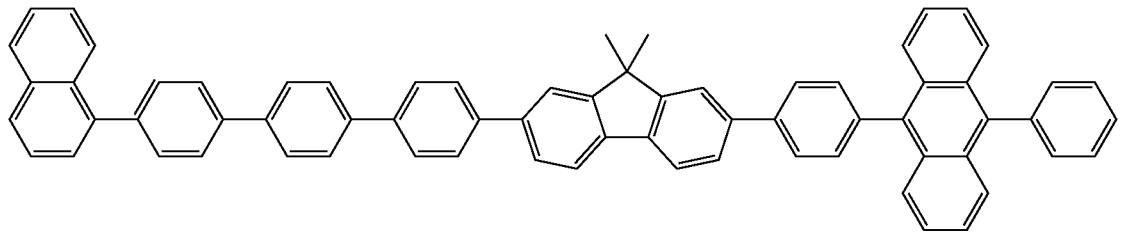
H-143
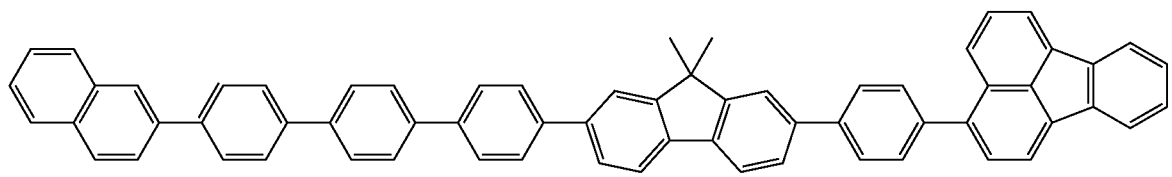
H-144
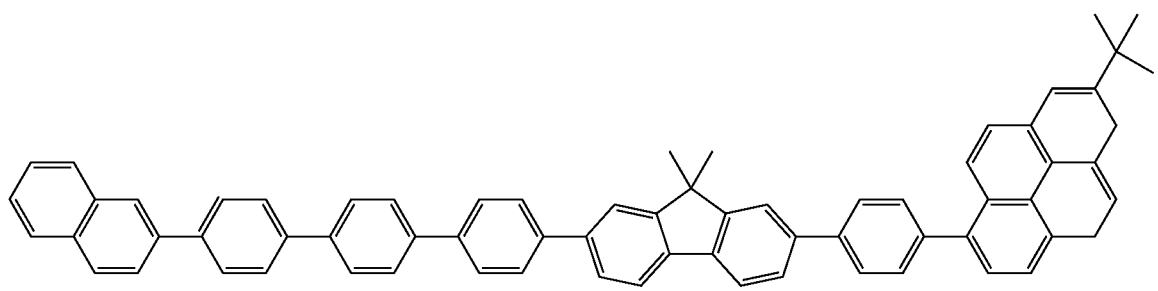
H-145
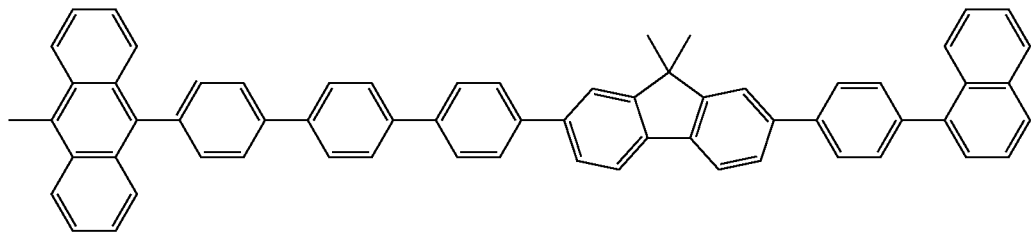
H-146
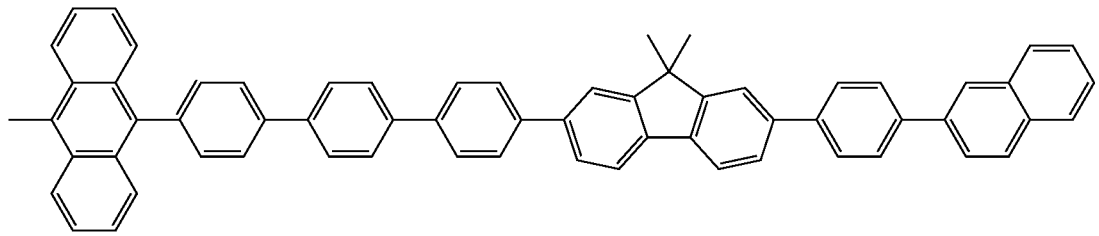
H-147
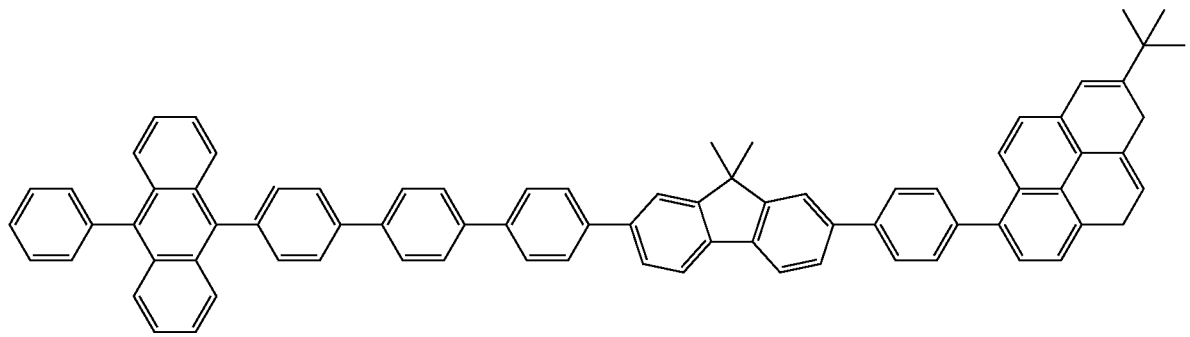

-continued
H-148
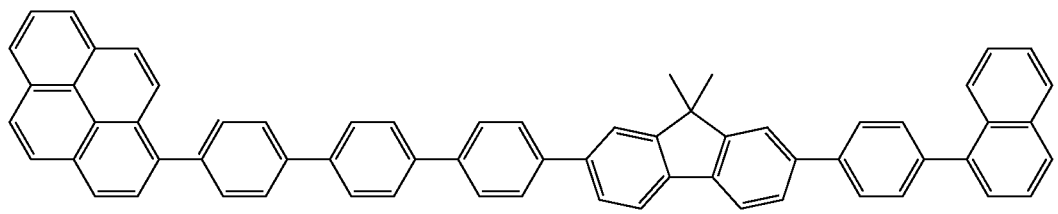
H-149
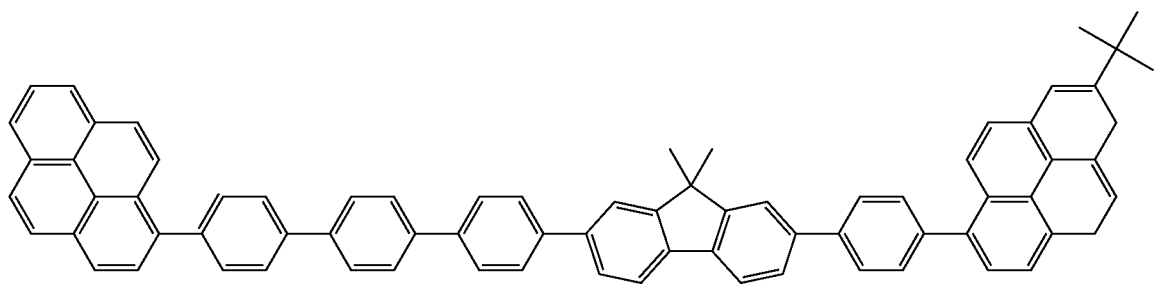
H-150
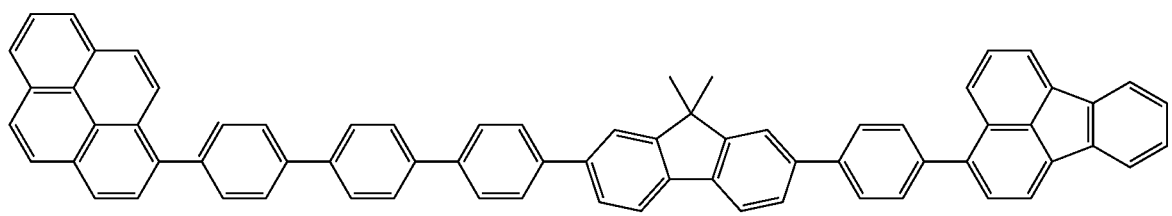
H-151
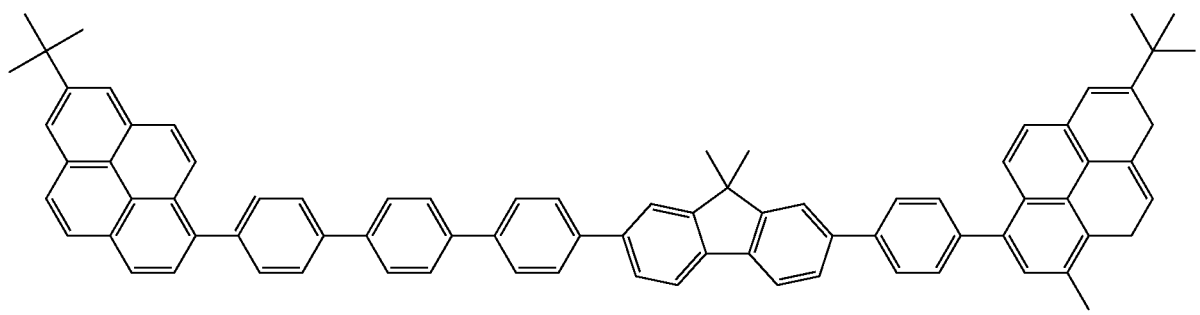
H-152
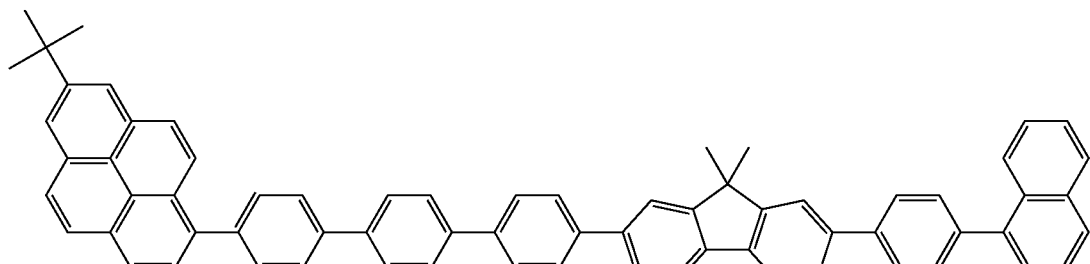
H-153
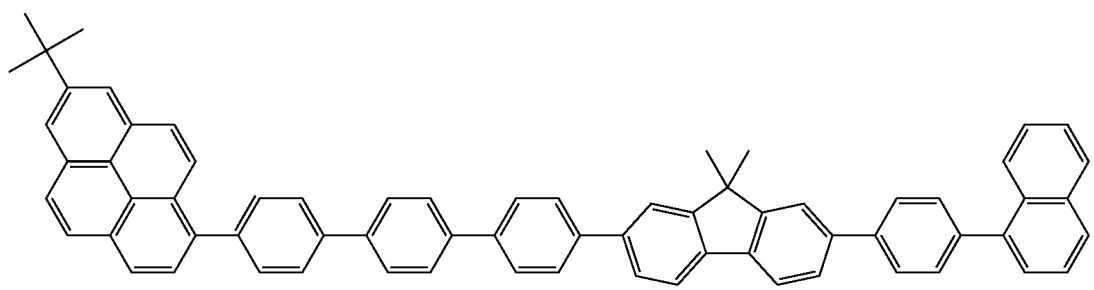

-continued
H-154
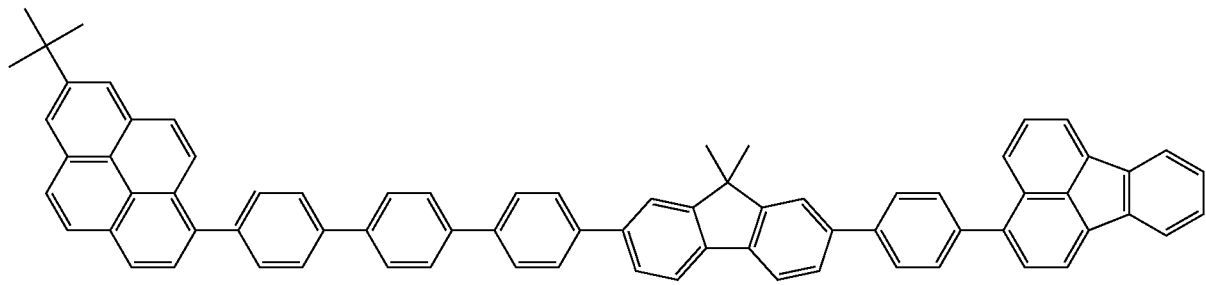
H-155
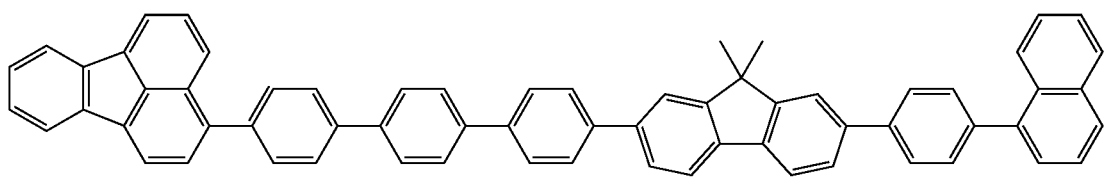
H-156
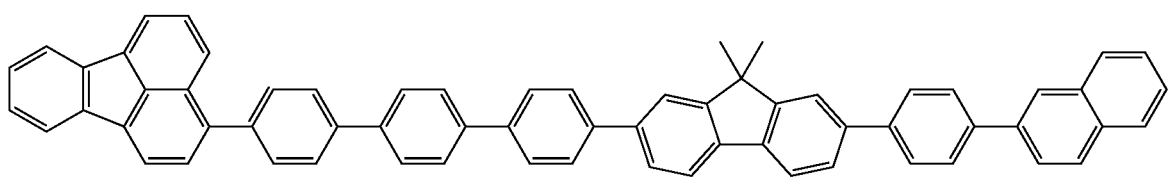
H-157
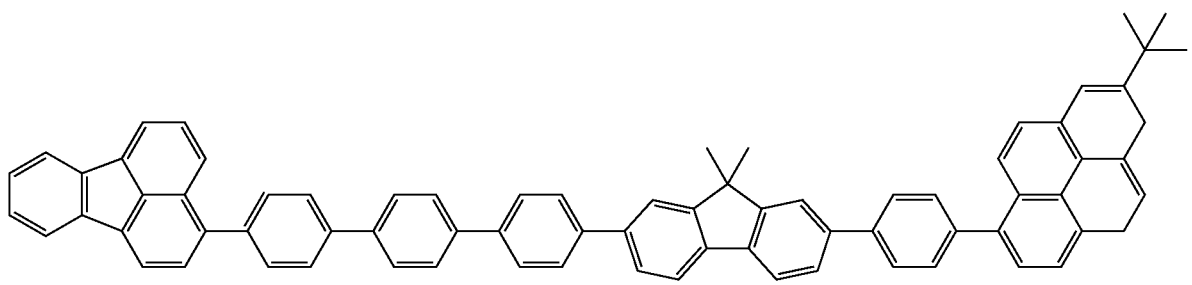
H-158
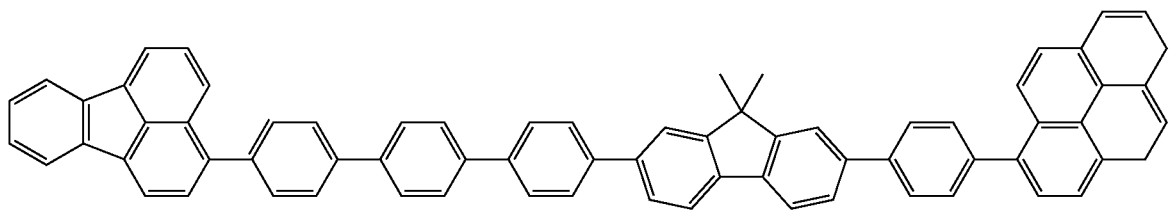
H-159
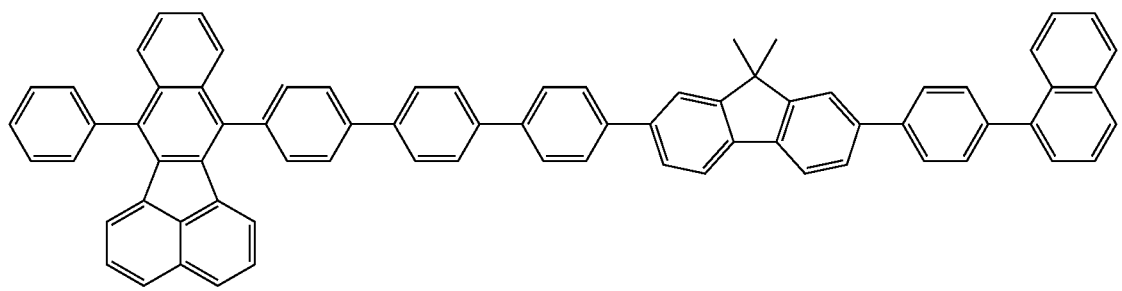

-continued
H-160
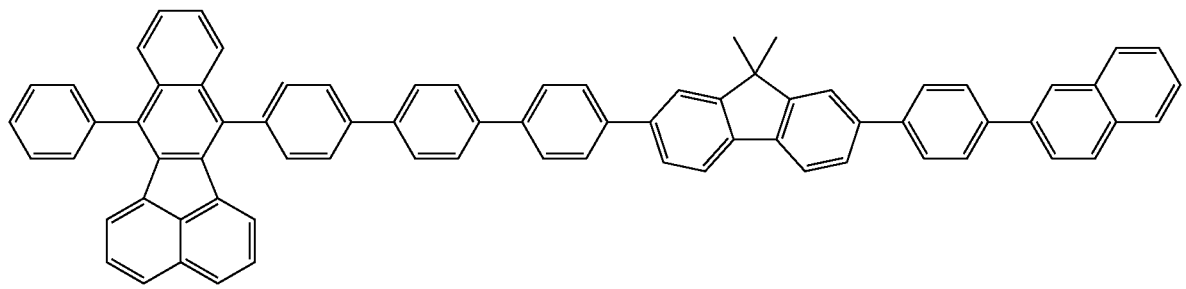
H-161
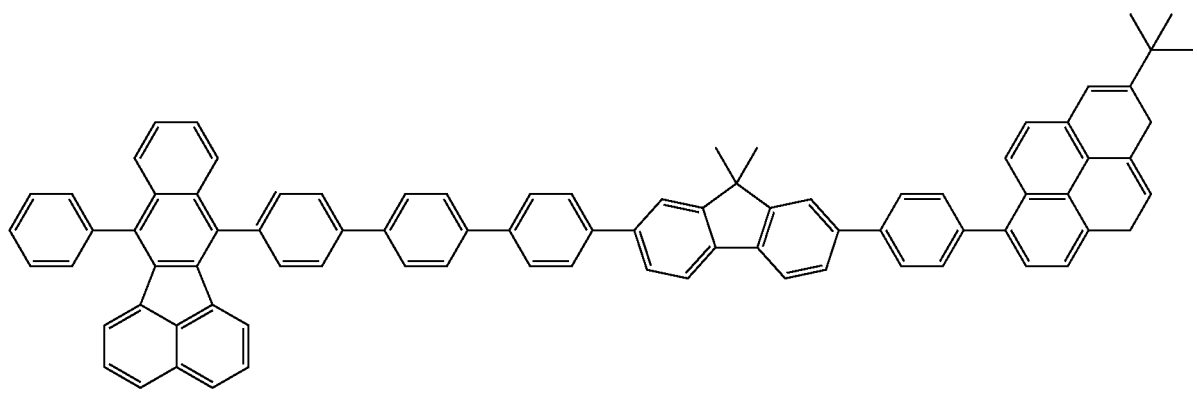
H-162
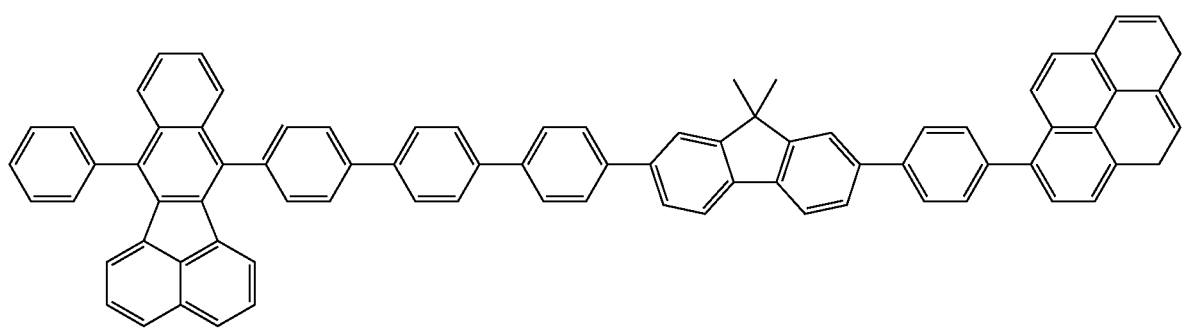
H-163
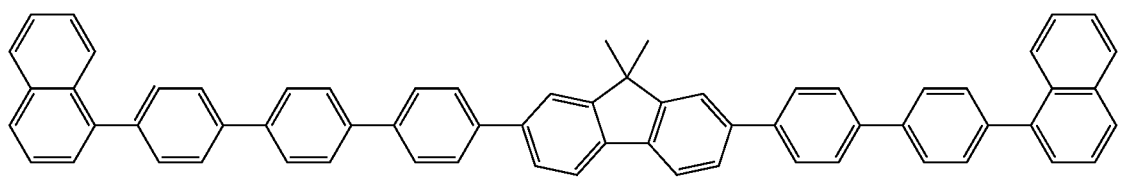
H-164
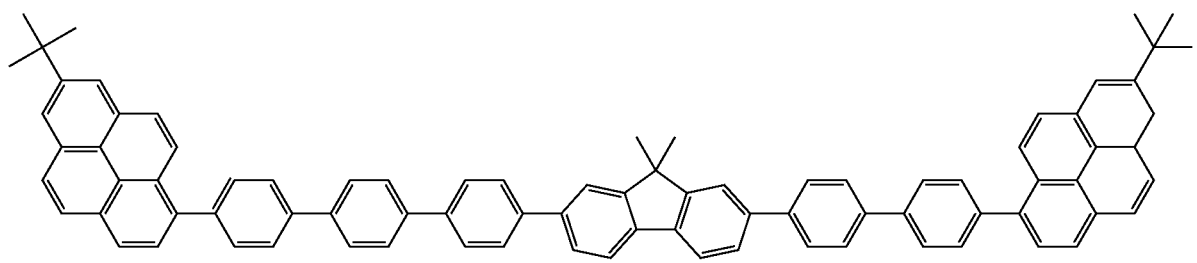

H-165
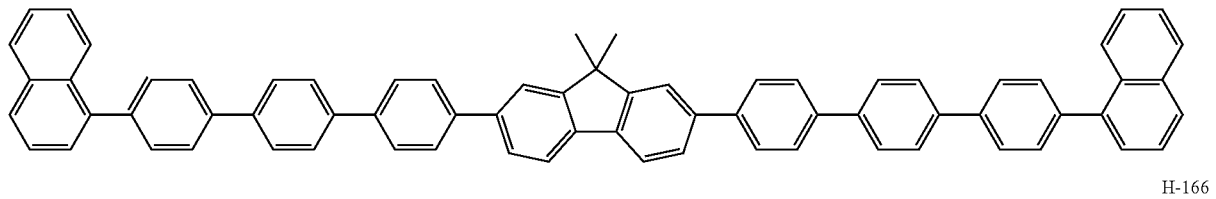
H-166
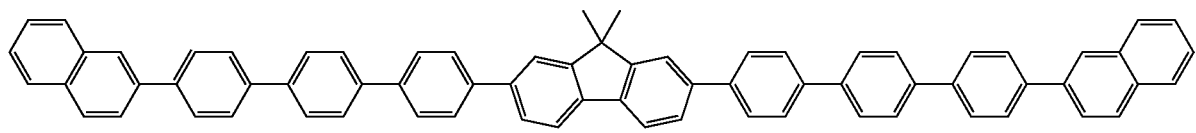
H-167
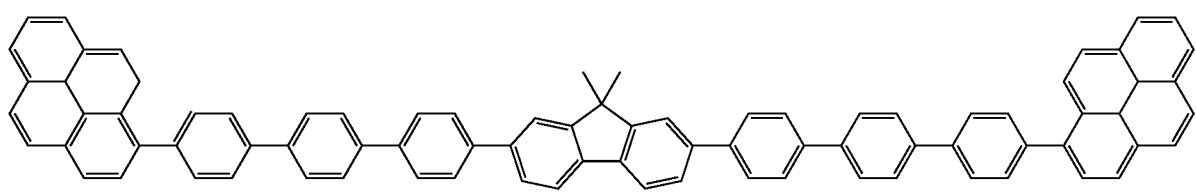
H-168
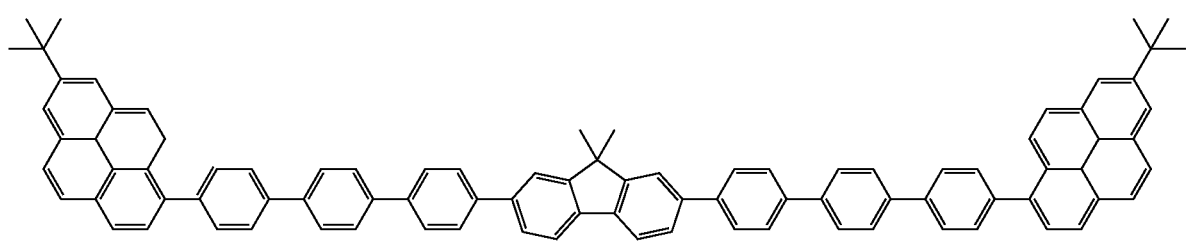
H-169
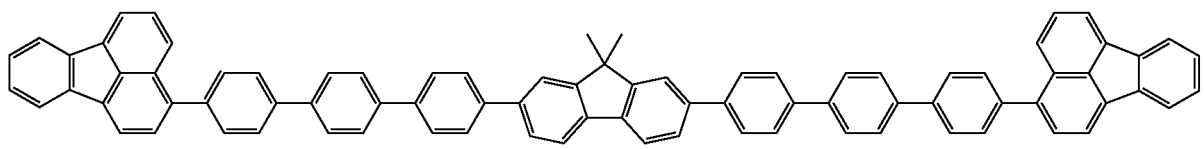
H-170
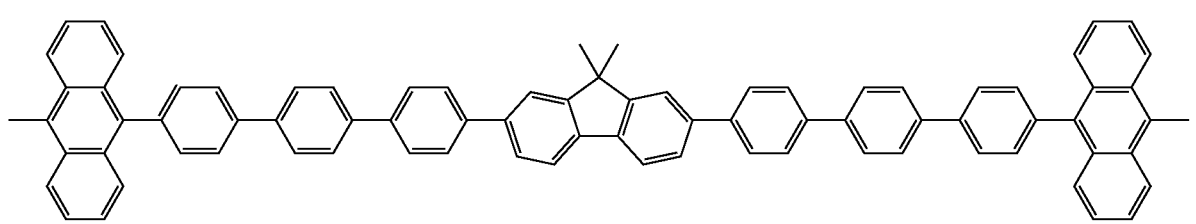
H-171
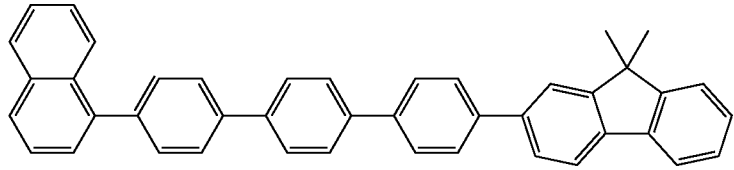
H-172
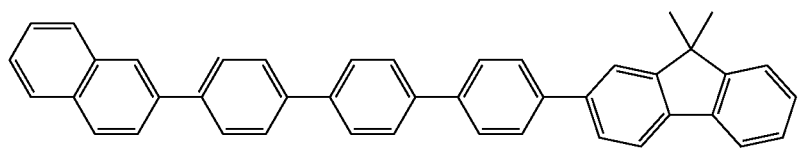

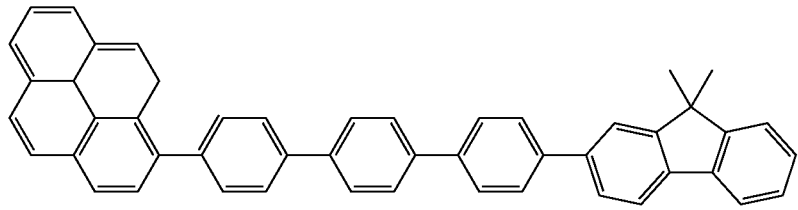
H-173
H-174
H-175
H-176
H-176
H-177

-continued
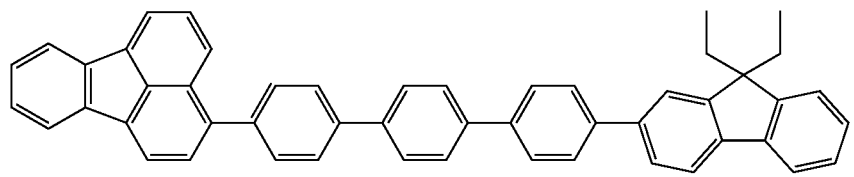
H-178
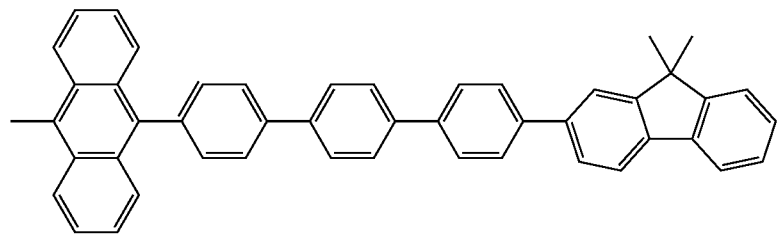
H-179
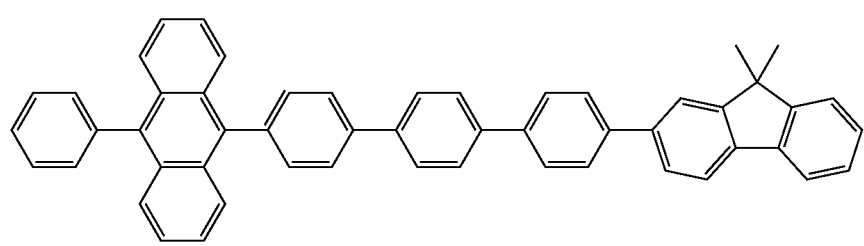
H-180
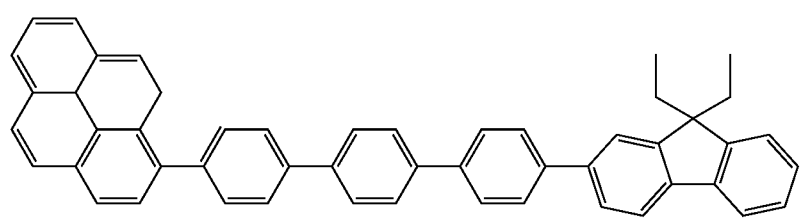
H-181
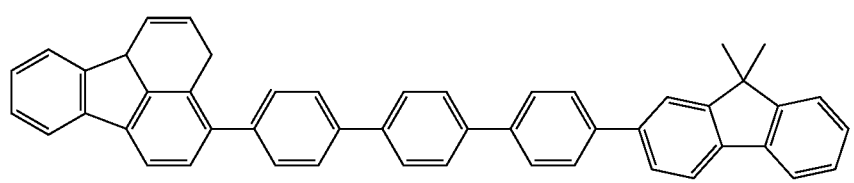
H-182
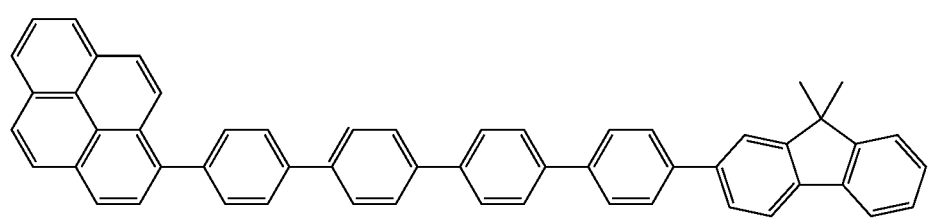
H-183
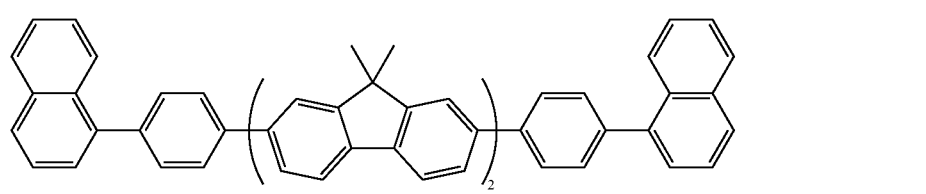
H-184
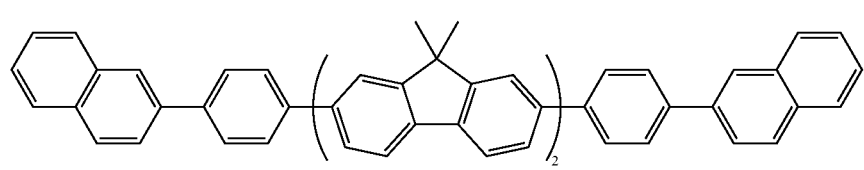
H-185

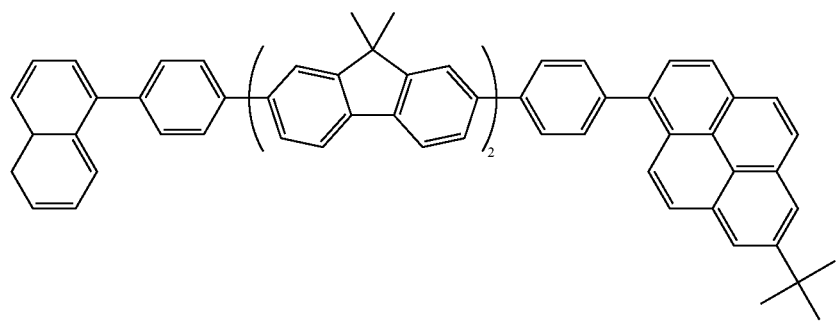
H-186
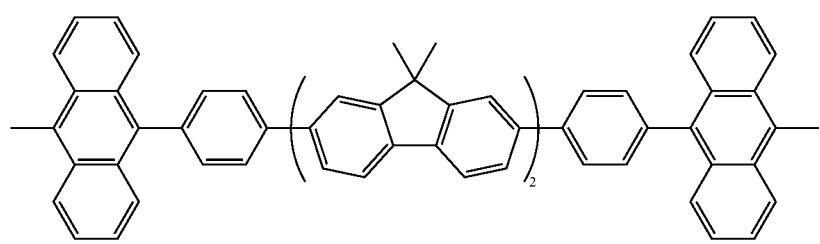
H-187
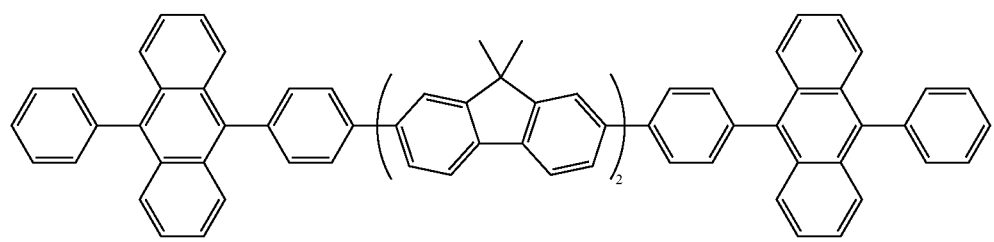
H-188
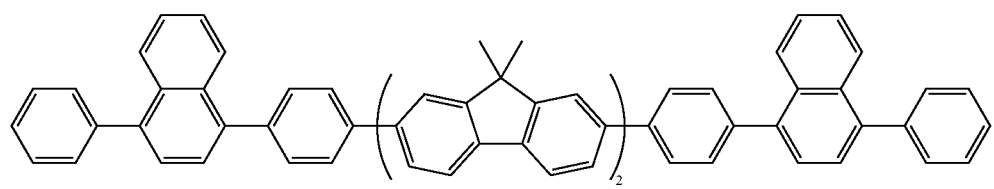
H-189
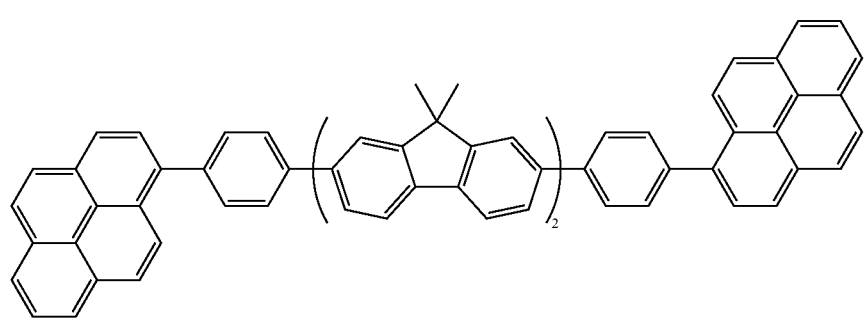
H-190

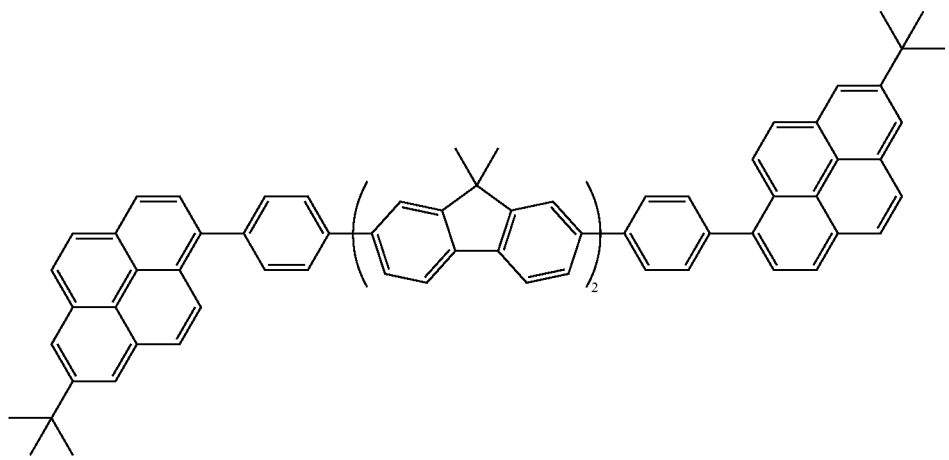
H-191
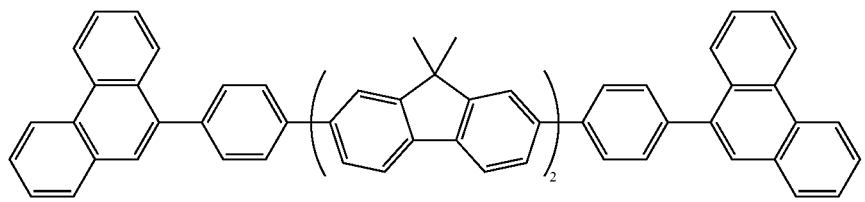
H-192
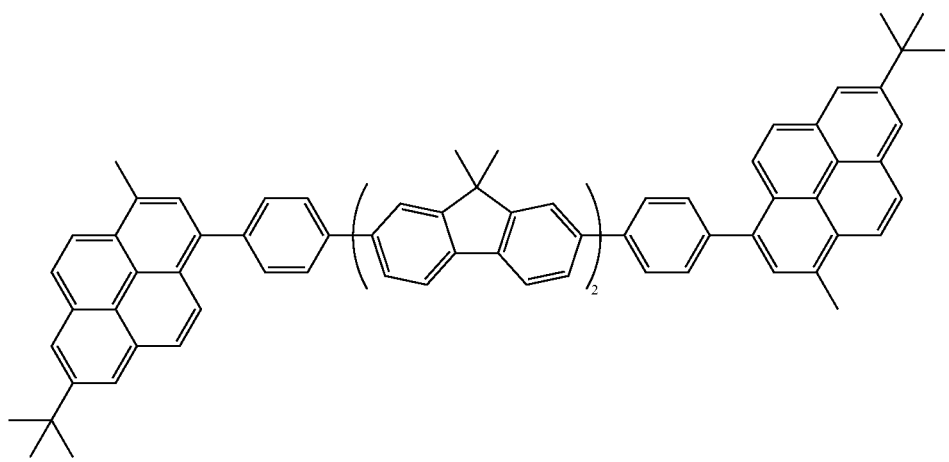
H-193
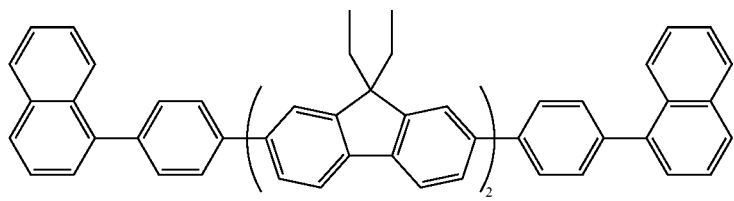
H-194
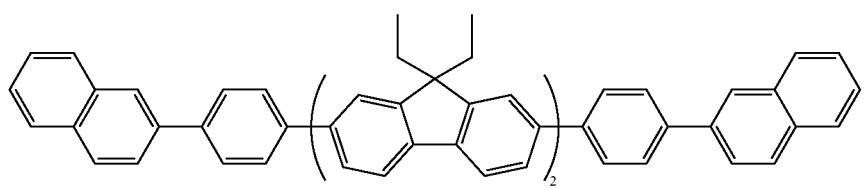
H-195

-continued
H-196
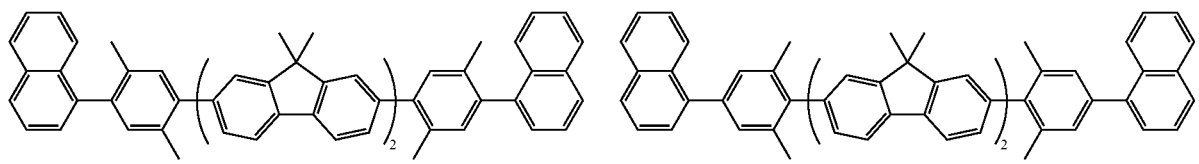
H-197
H-198
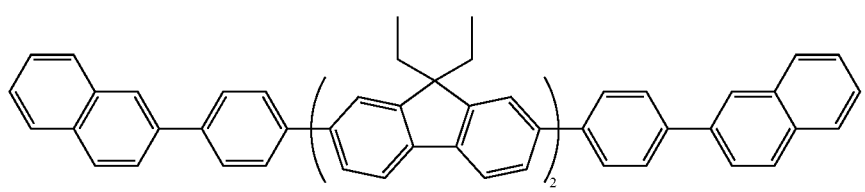
H-199
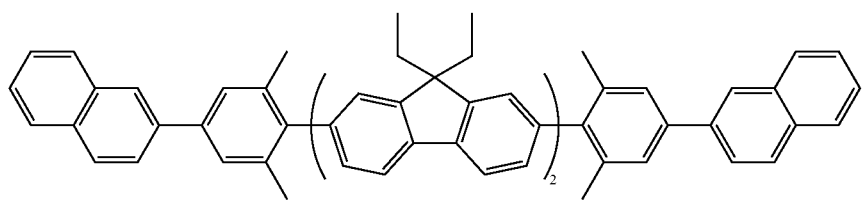
H-200
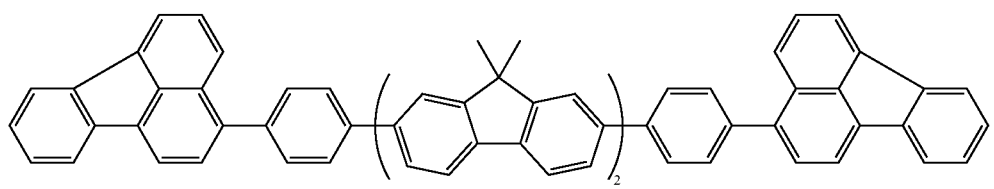
H-201
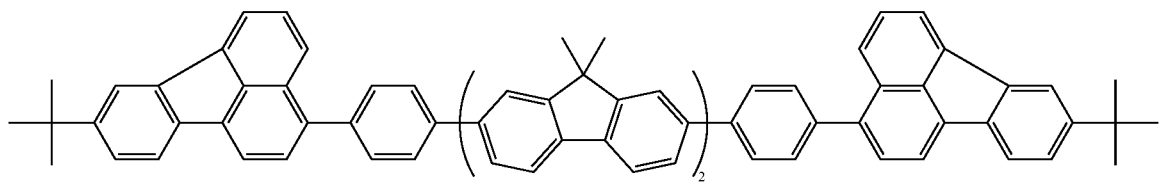
H-201
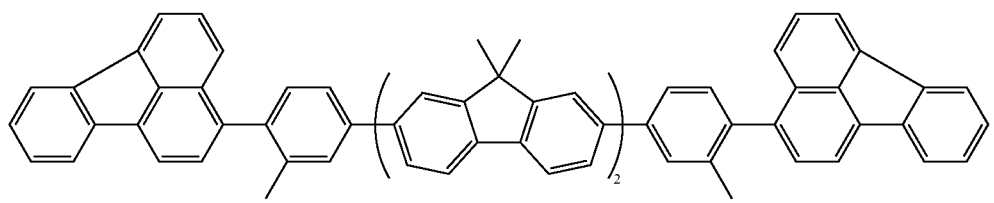
H-202
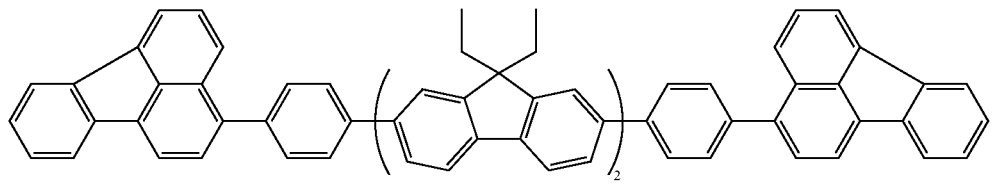

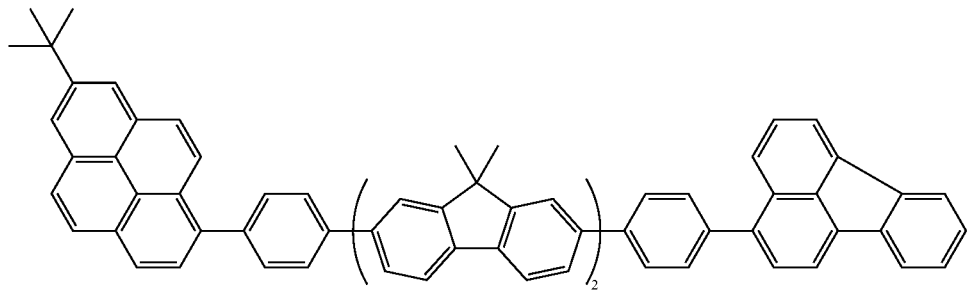
H-203
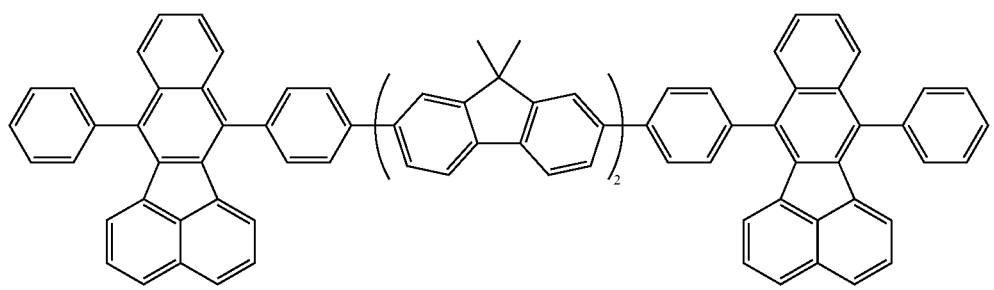
H-204
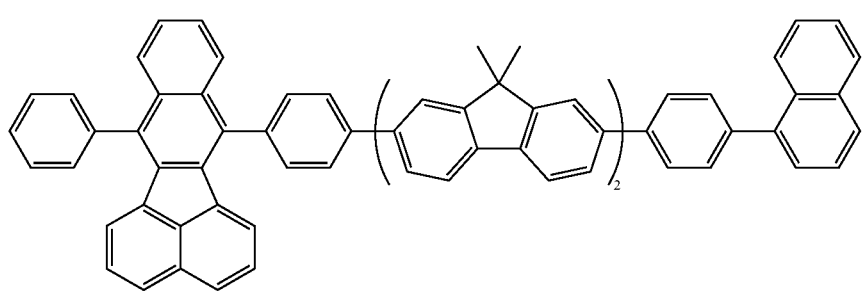
H-205
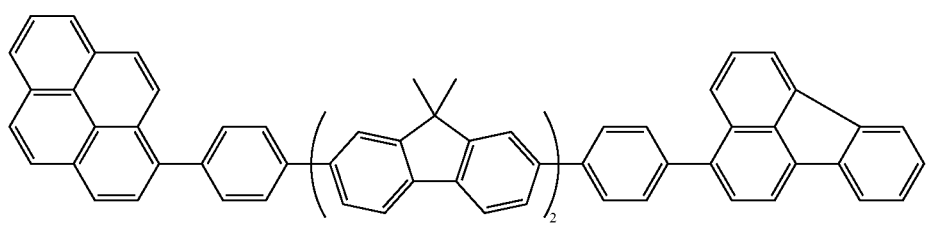
H-206
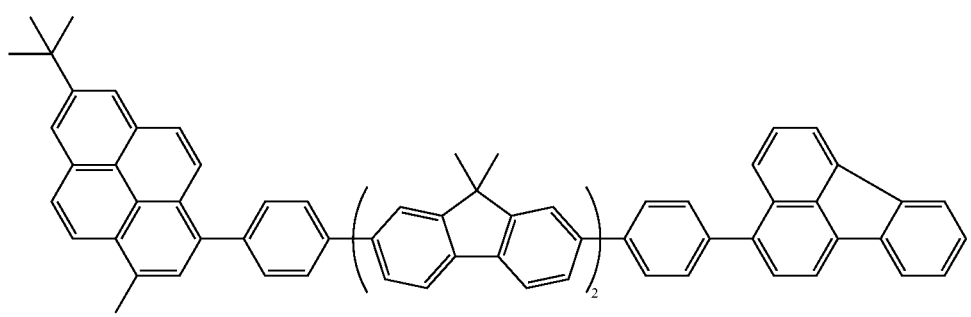
H-207
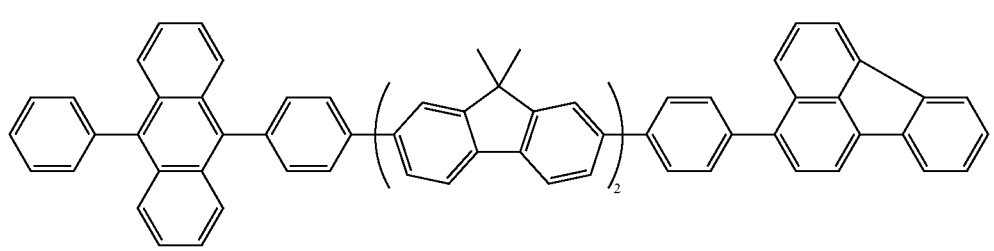
H-208

H-209
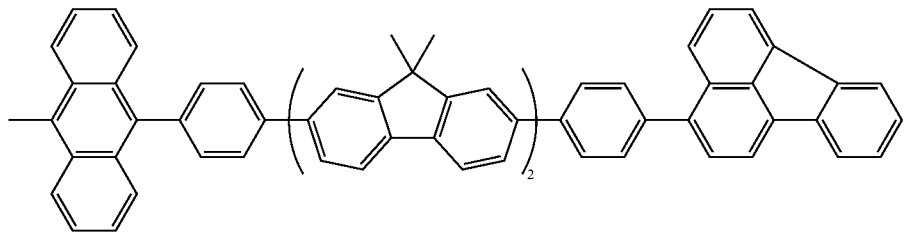
H-210
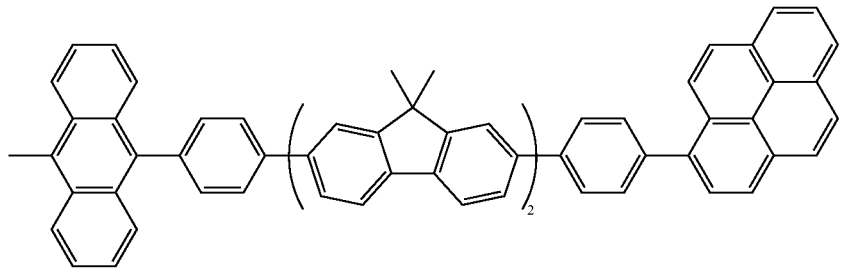
H-211
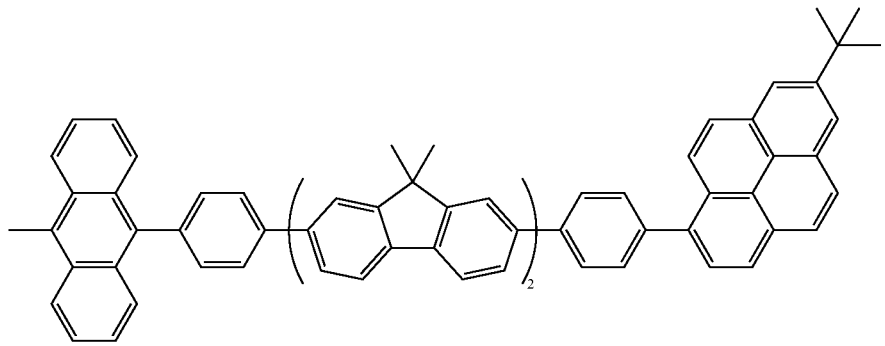
H-212
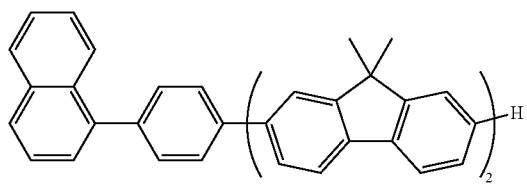
H-213
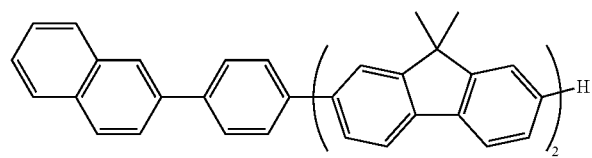
H-214
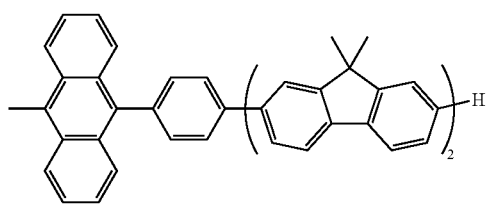
H-215
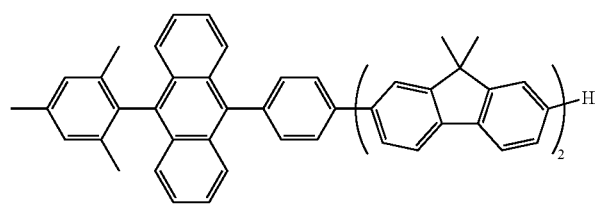
H-216
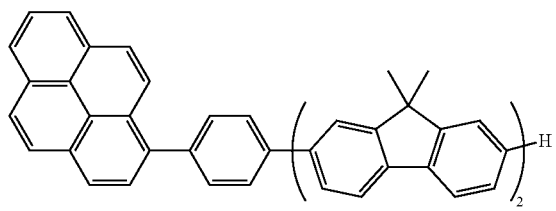
H-217
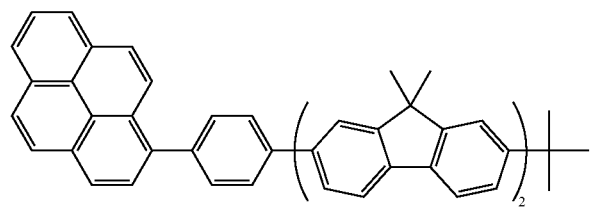

H-218
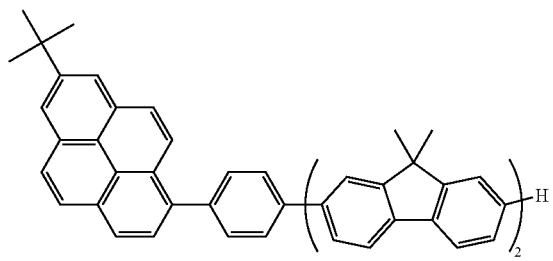
H-219
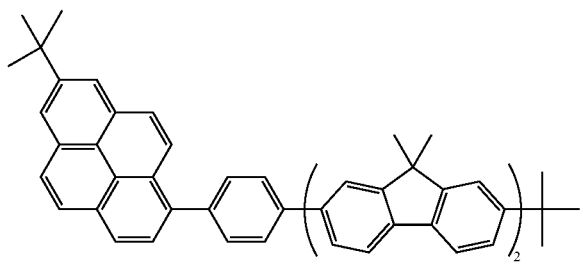
H-220
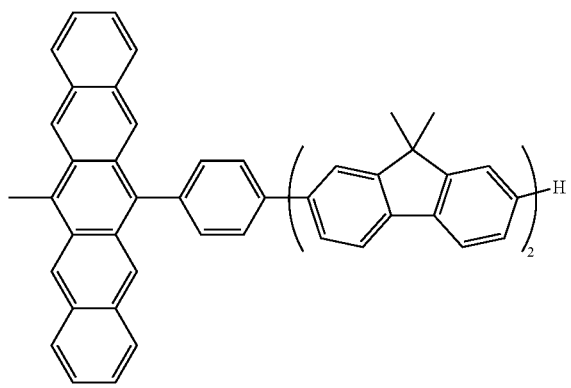
H-221
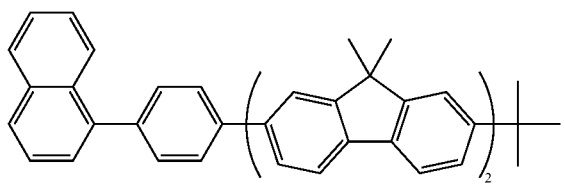
H-222
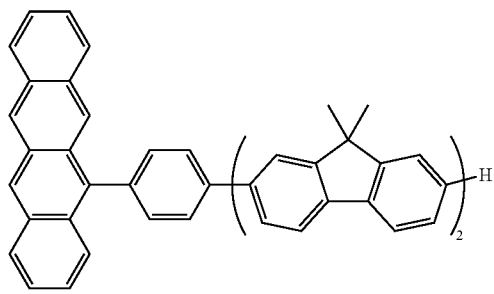
H-223
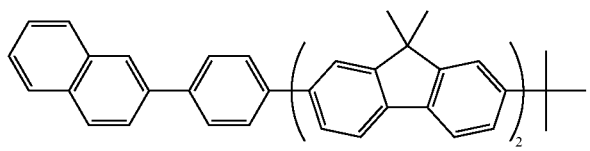
H-224
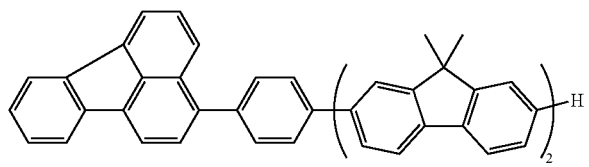
H-225
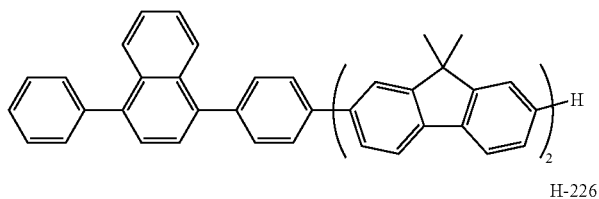
H-226
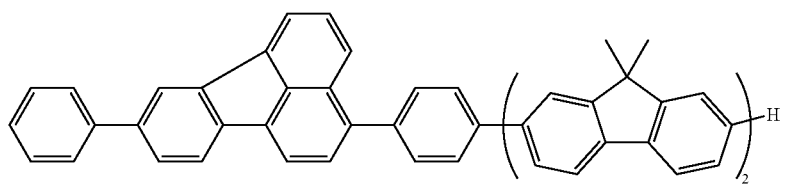
H-227
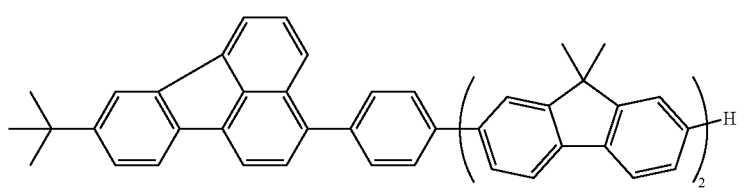

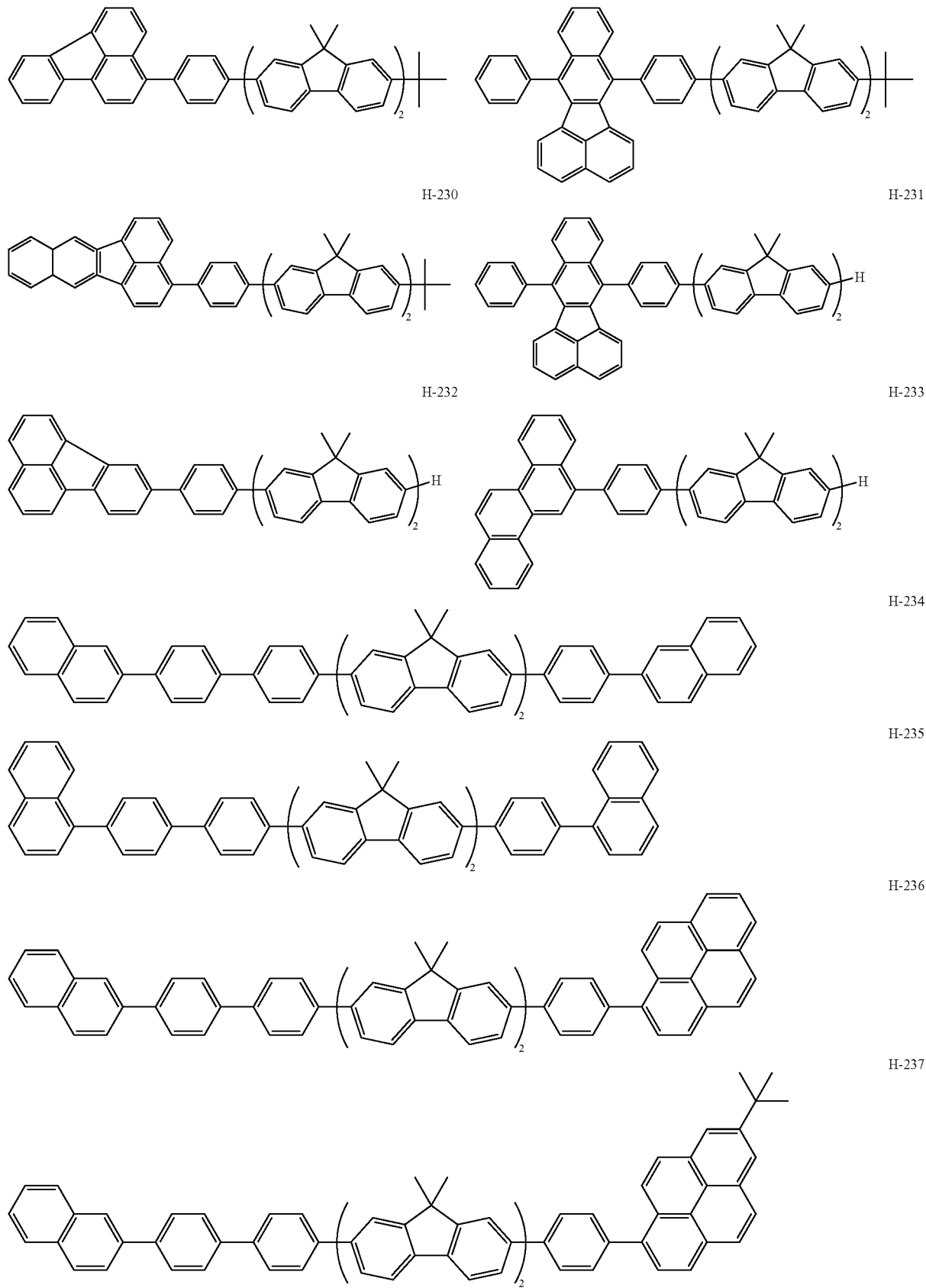

-continued
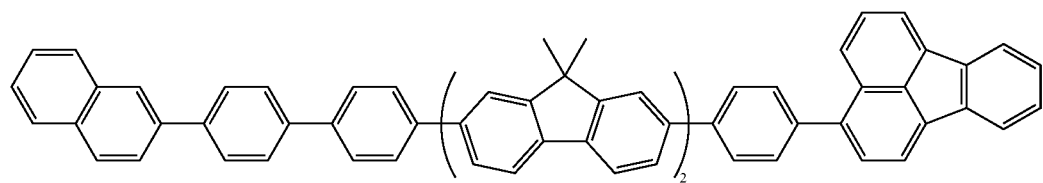
H-238
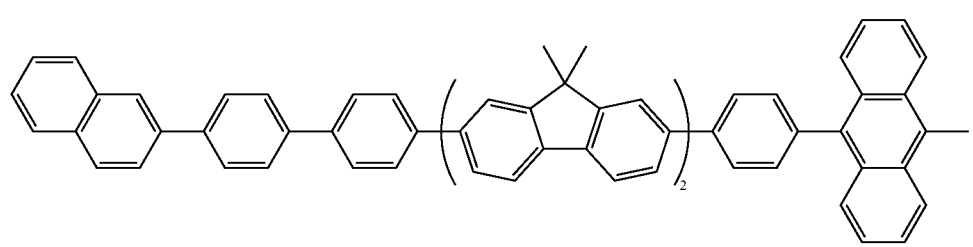
H-239
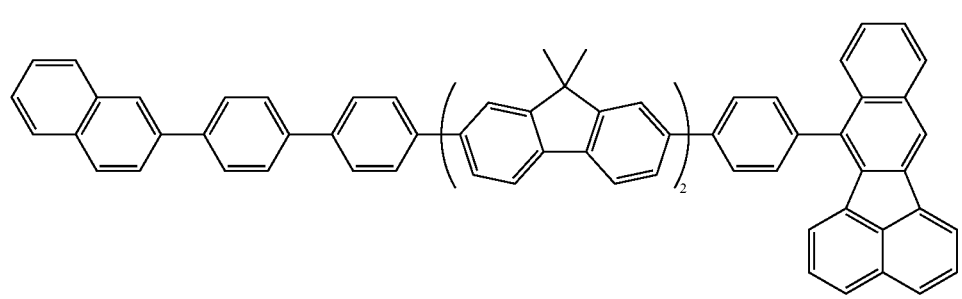
H-240
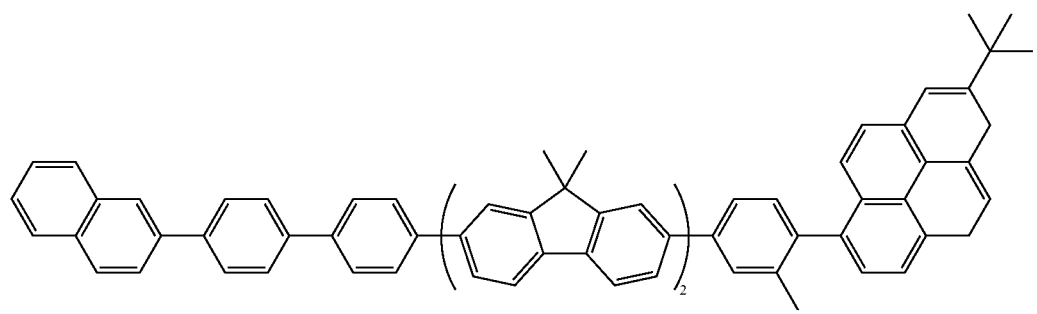
H-241
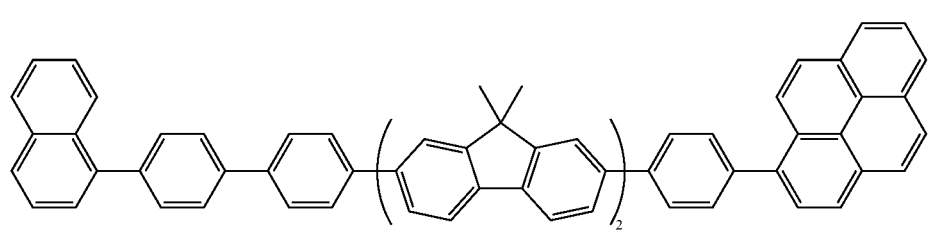
H-242
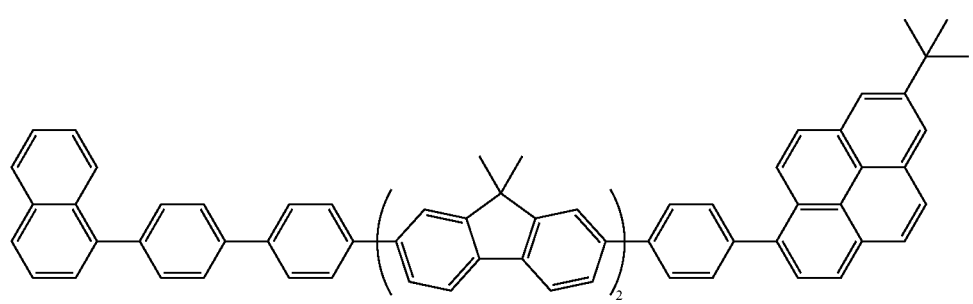
H-243

-continued
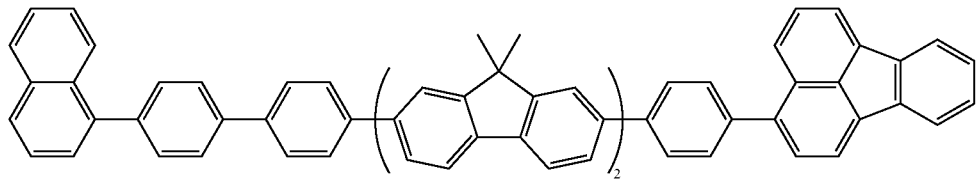
H-244
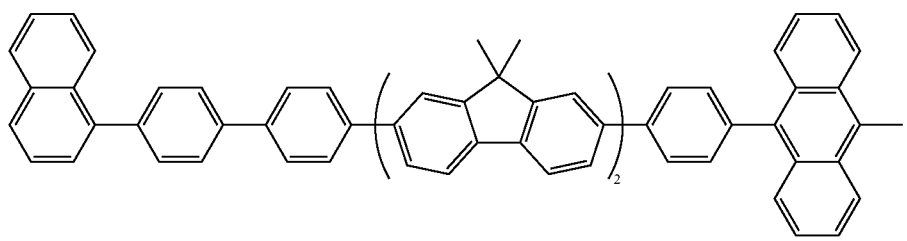
H-245
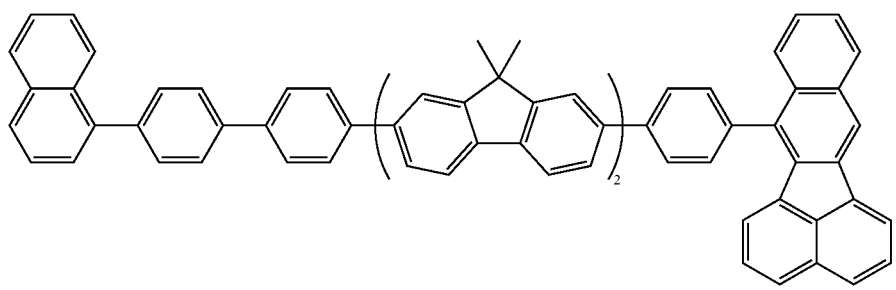
H-246
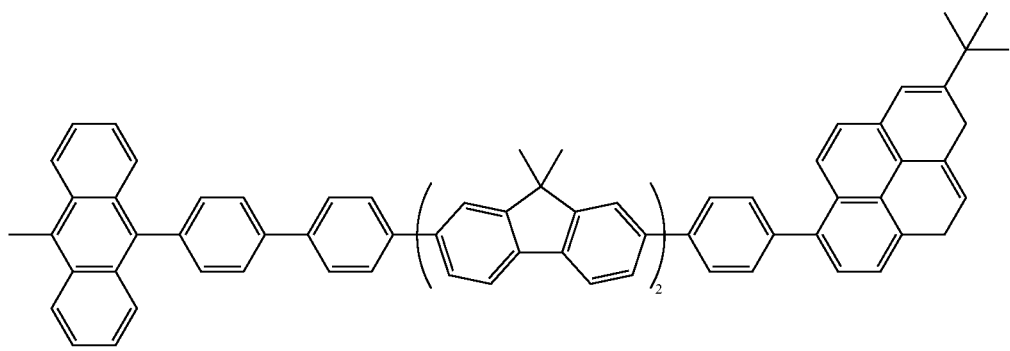
H-247
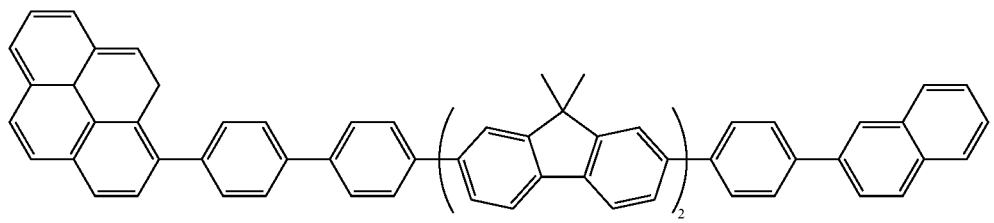
H-248
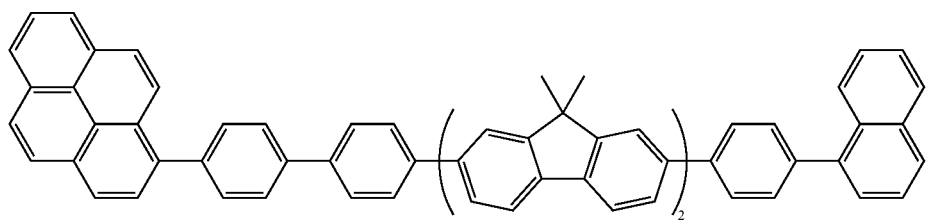
H-249

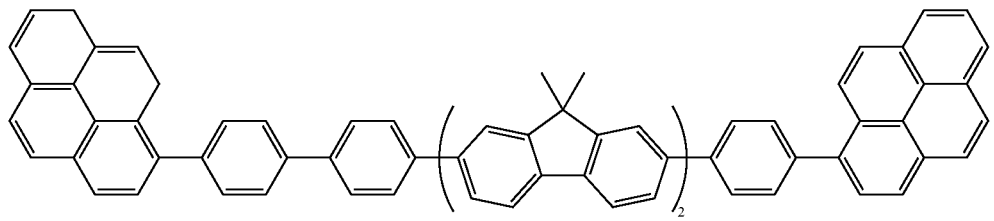
H-250
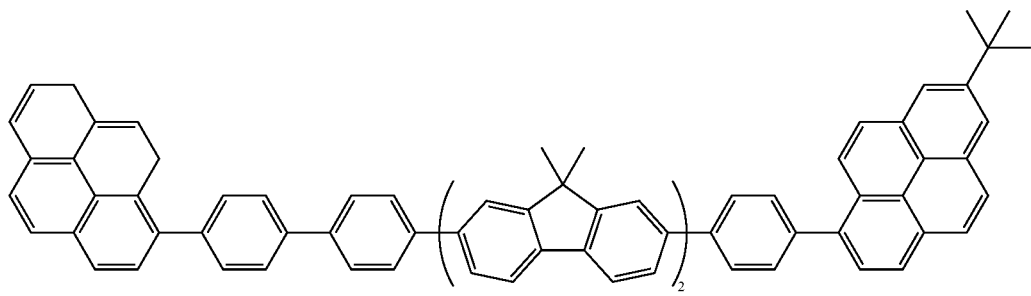
H-251
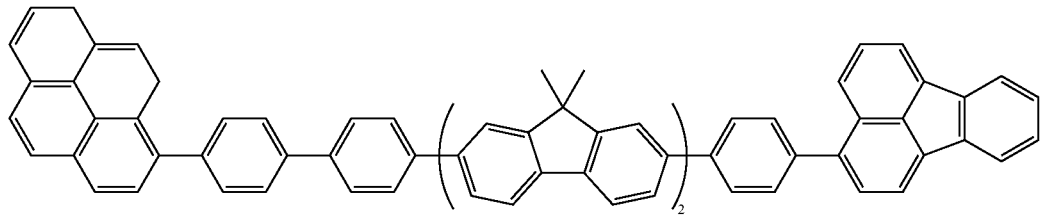
H-252
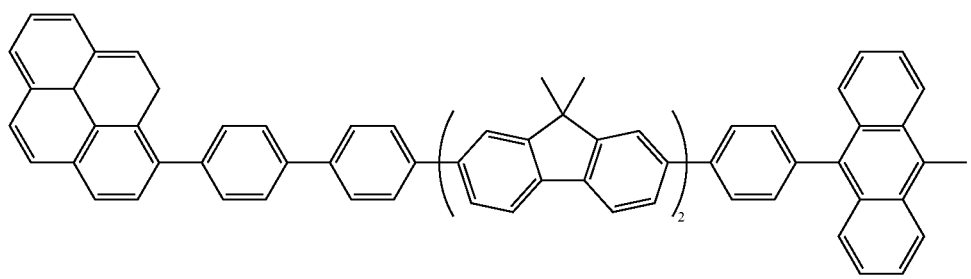
H-253
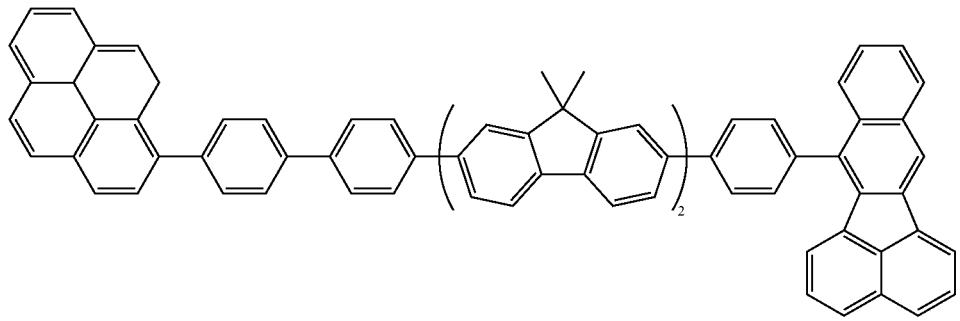
H-254
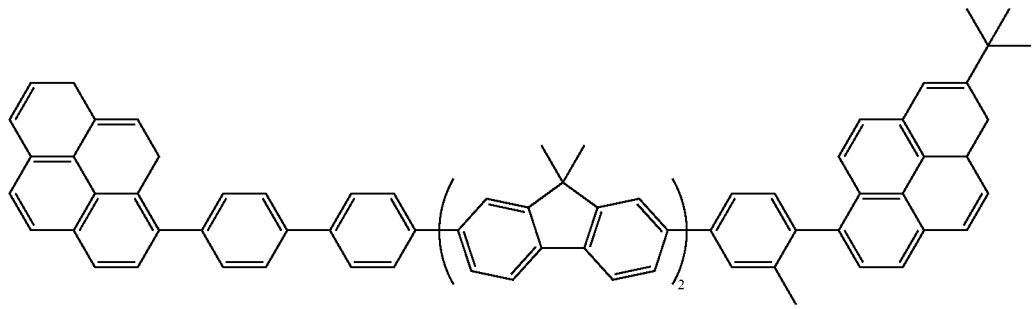
H-255

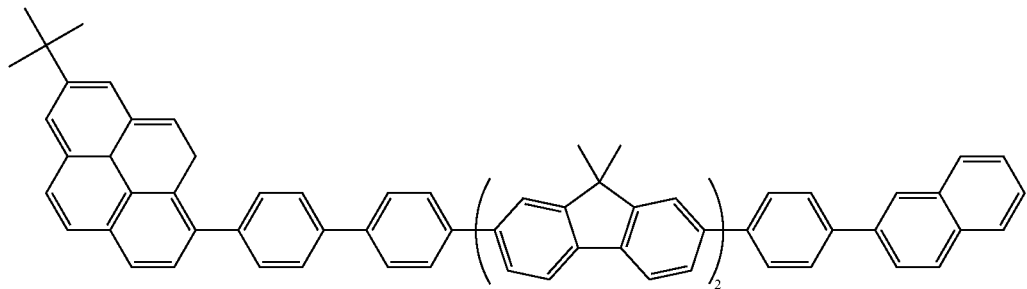
H-256
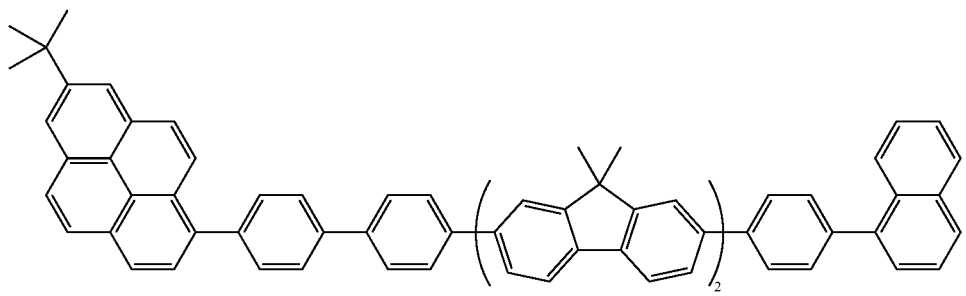
H-257
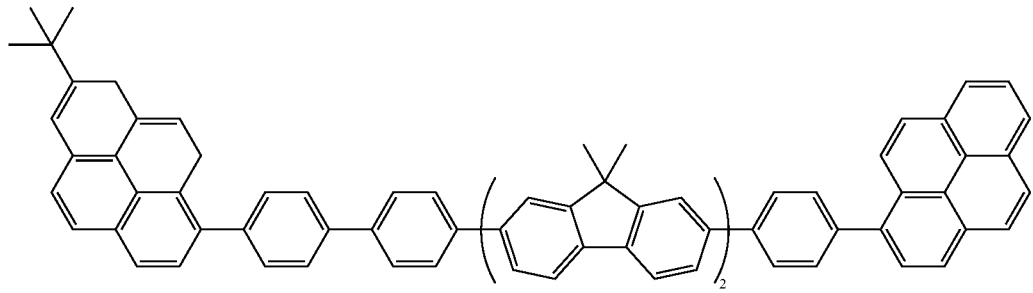
H-258
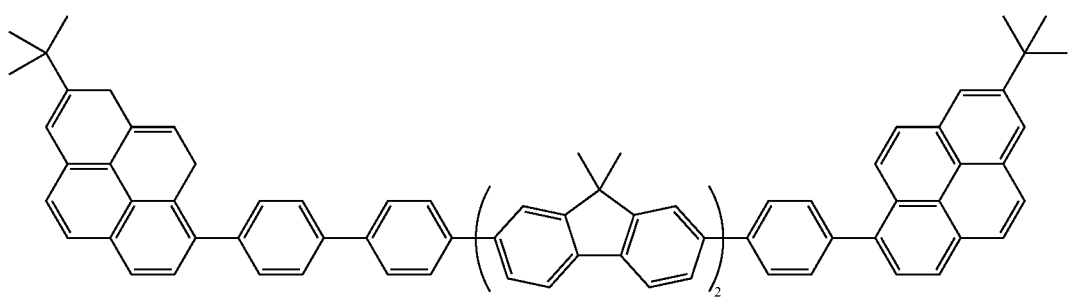
H-259
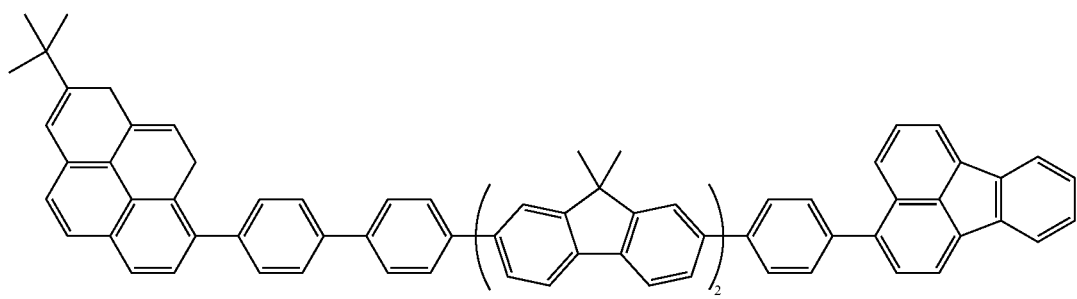
H-260

H-261
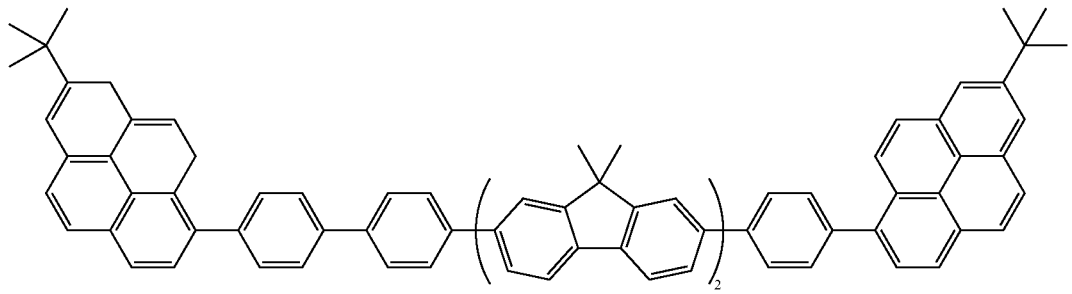
H-262
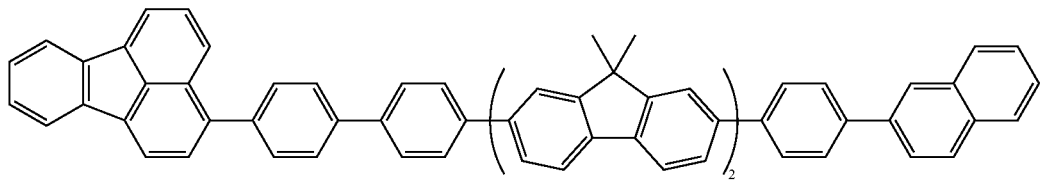
H-263
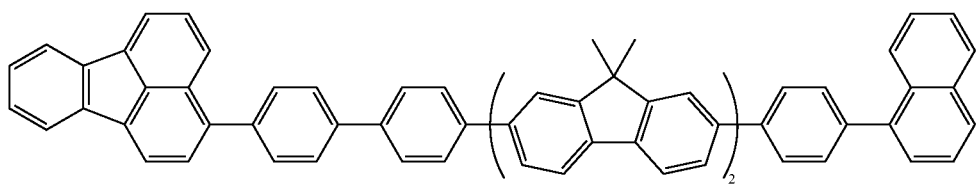
H-264
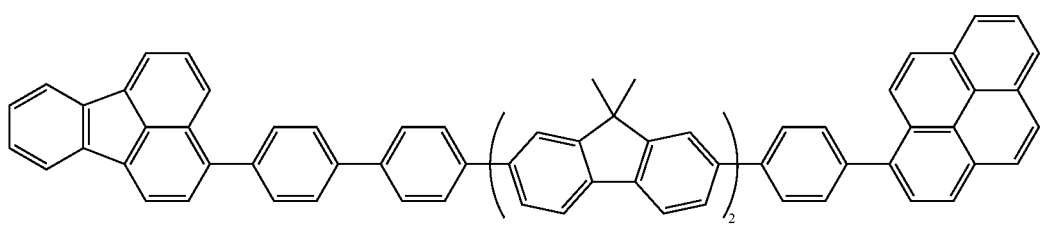
H-265
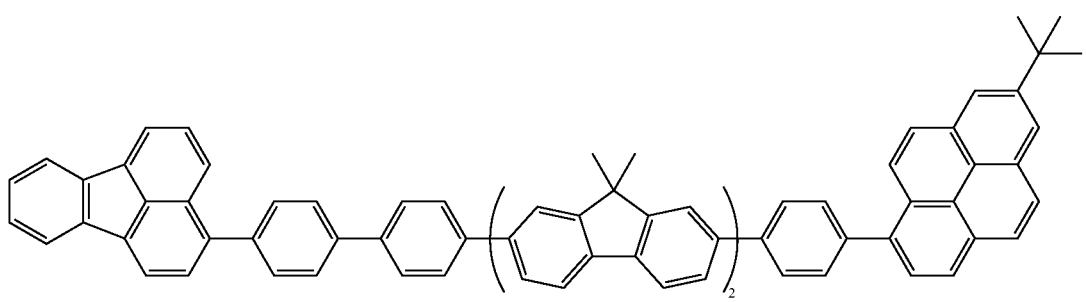
H-266
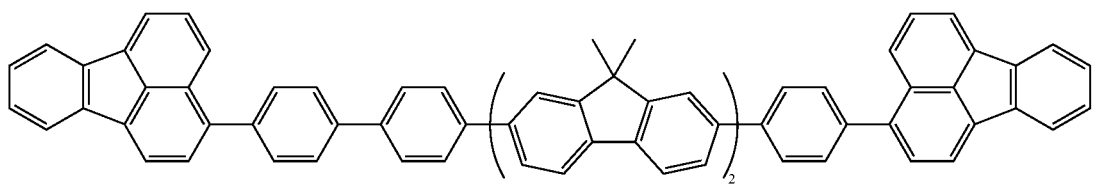
H-267
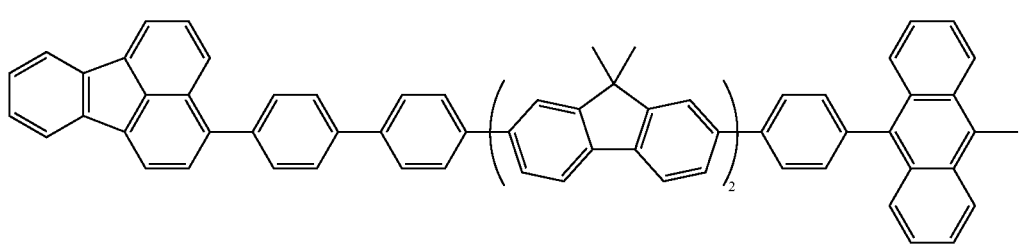

-continued
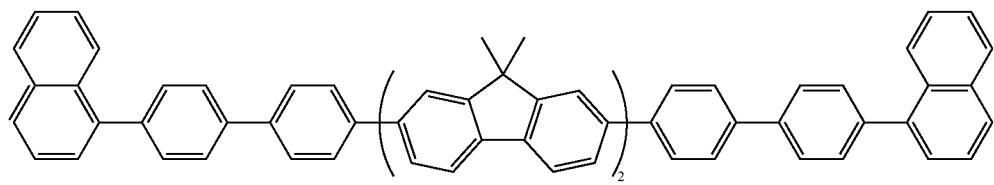
H-268
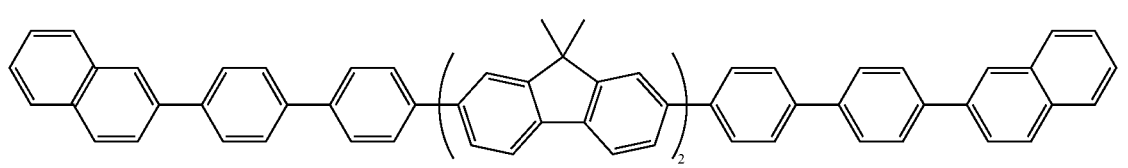
H-269
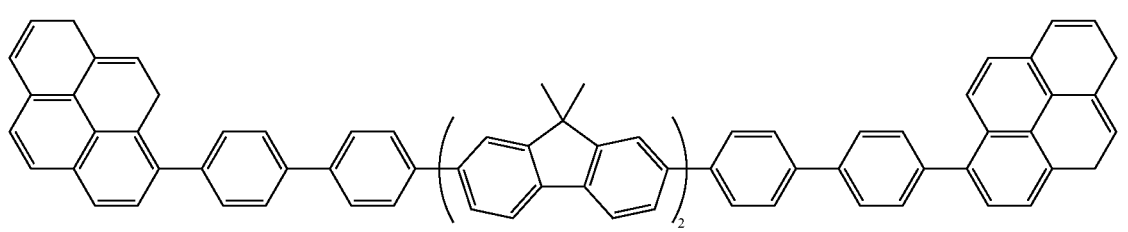
H-270
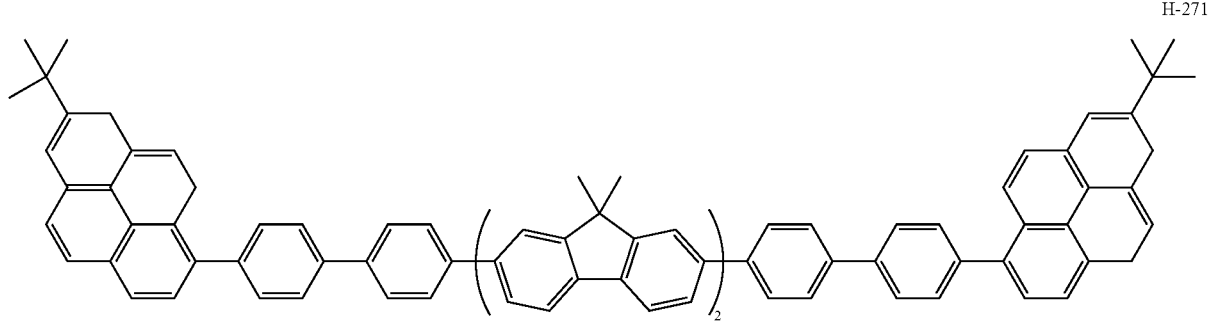
H-271
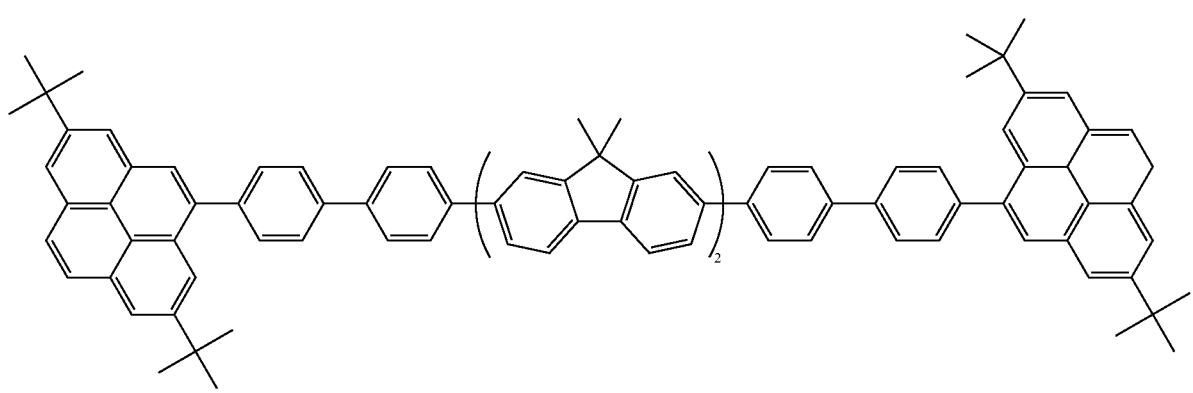
H-272
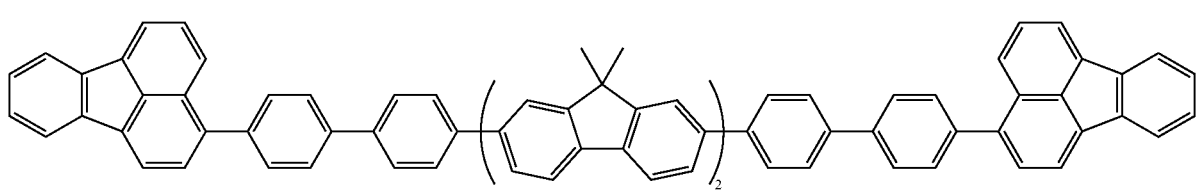
H-273

-continued
H-274
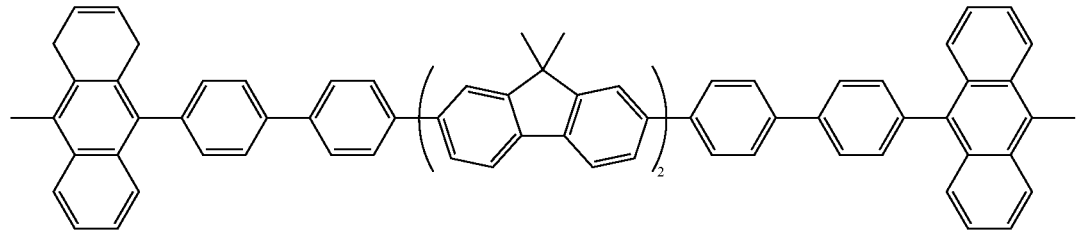
H-275
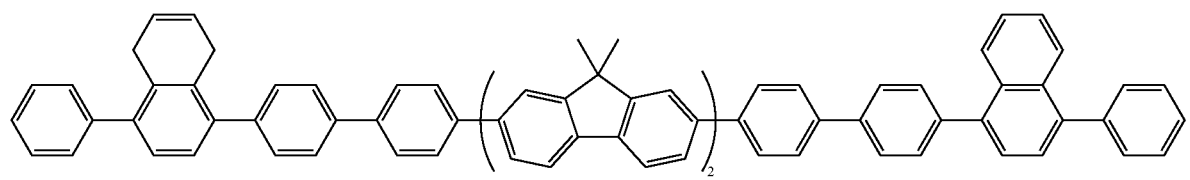
H-276
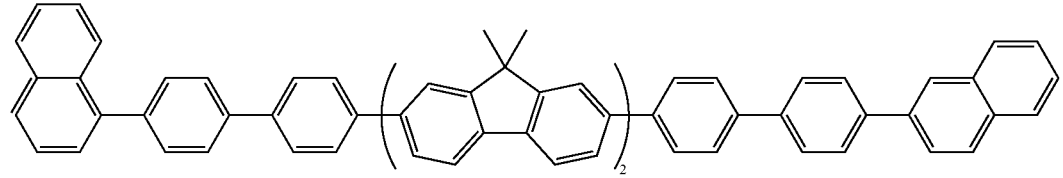
H-277
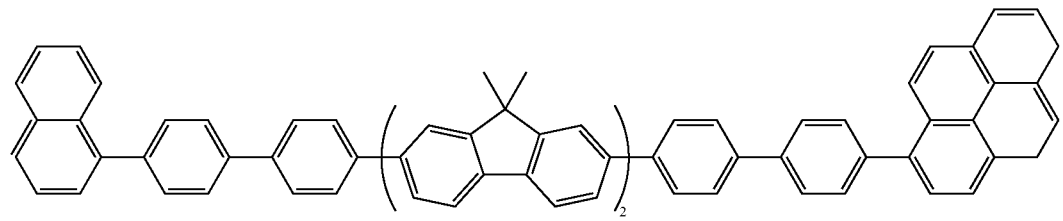
H-278
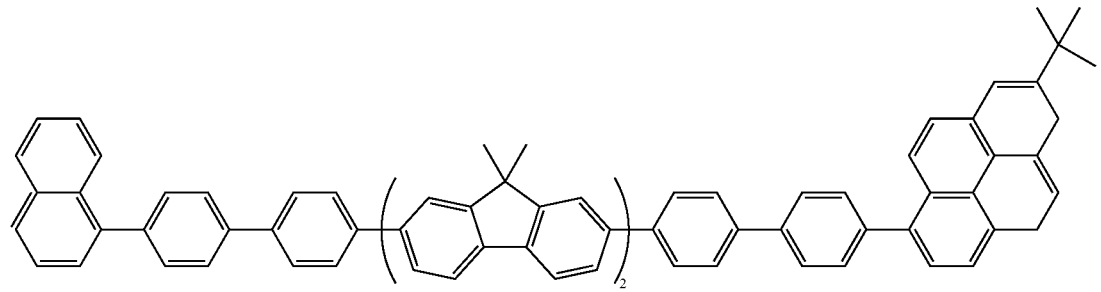
H-279
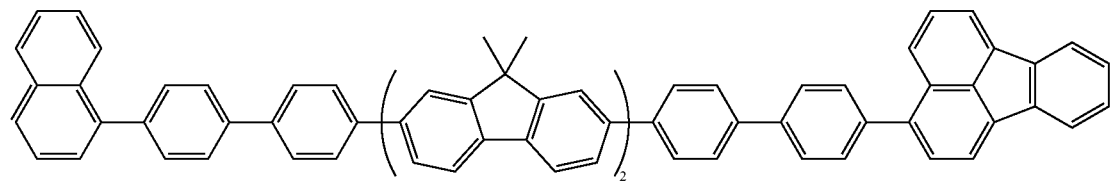
H-280
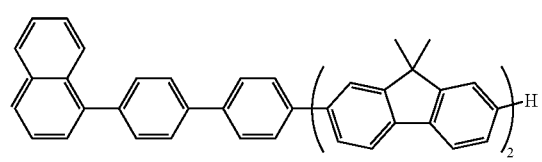
H-281
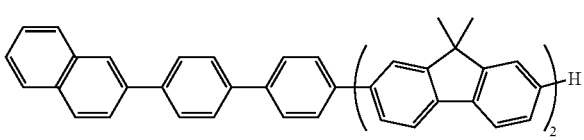

-continued
H-282
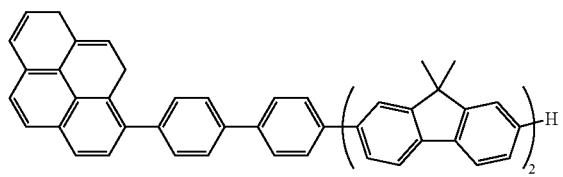
H-283
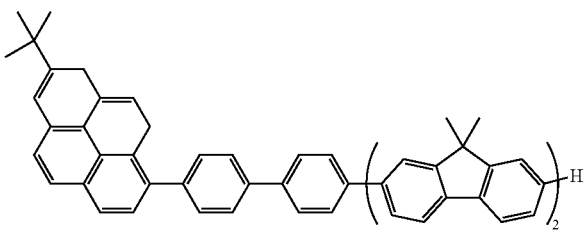
H-284
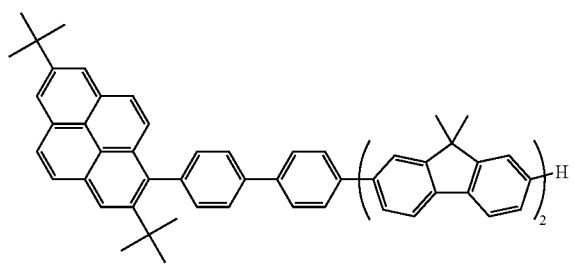
H-285
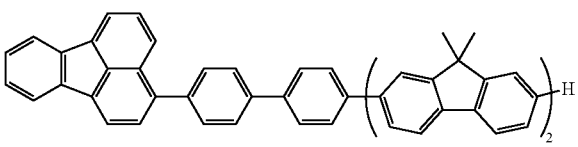
H-286
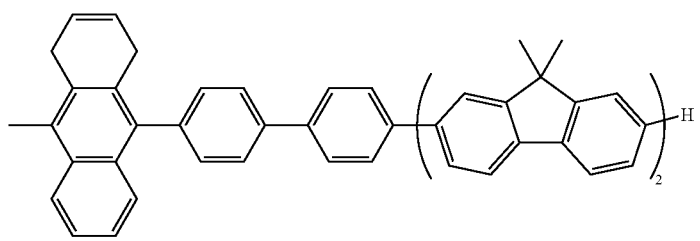
H-287
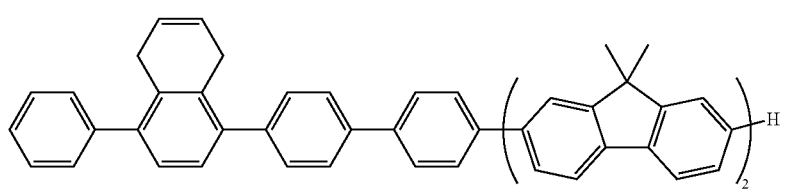
H-288
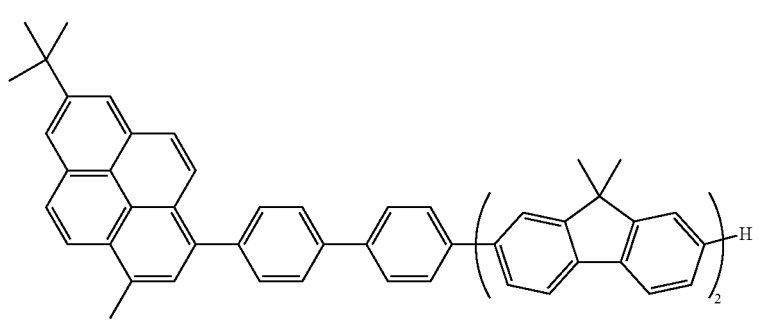
H-289
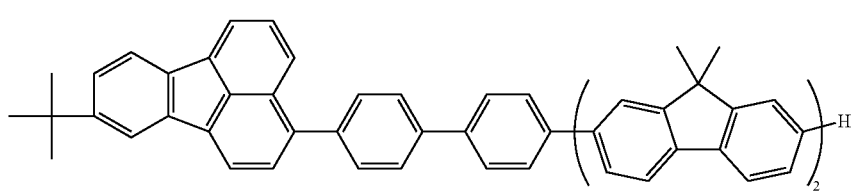

-continued
H-290
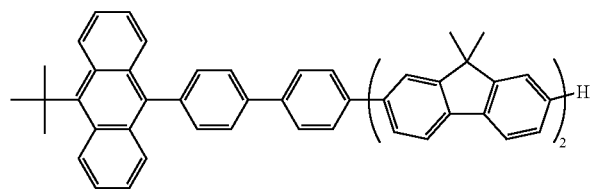
H-291
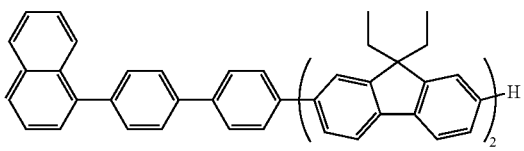
H-292
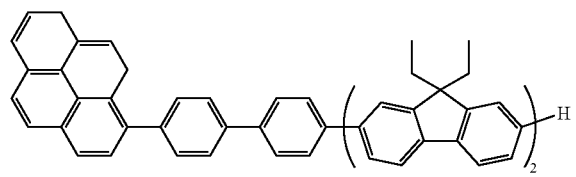
H-293
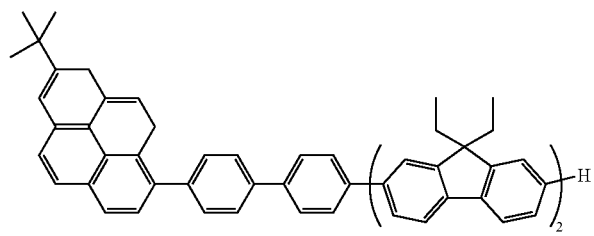
H-294
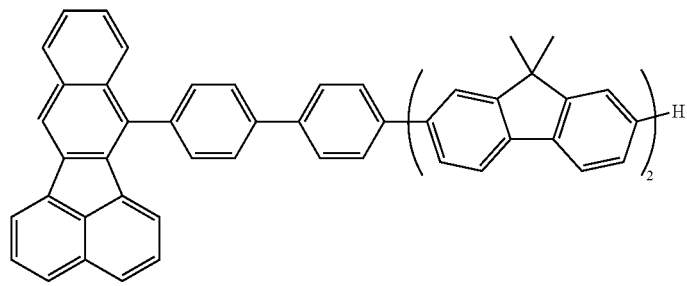
H-295
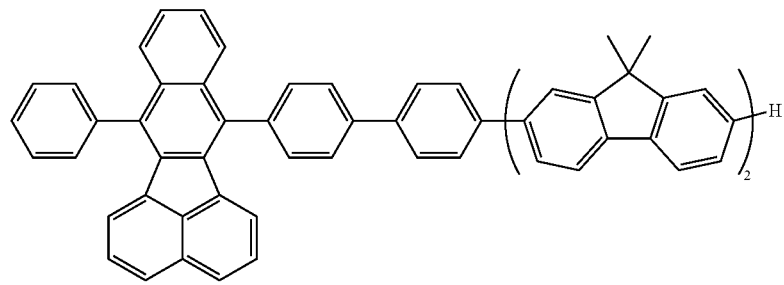
H-296
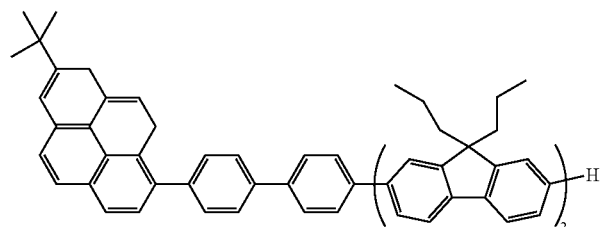
H-297
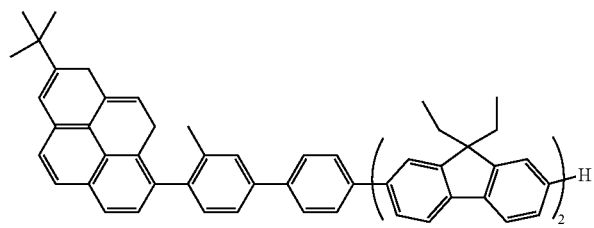
H-298
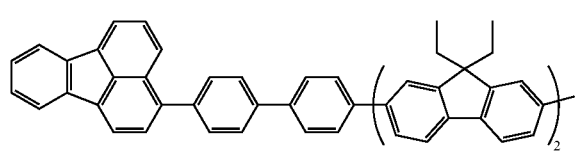
H-299
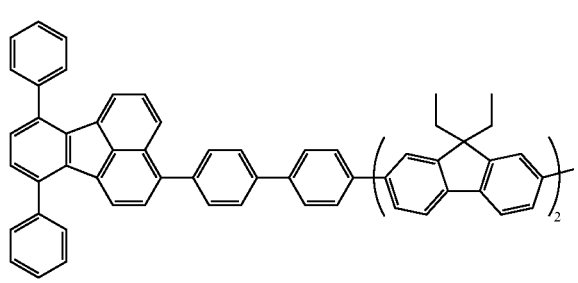

H-300
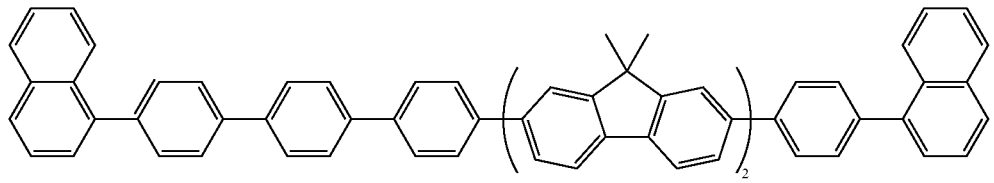
H-301
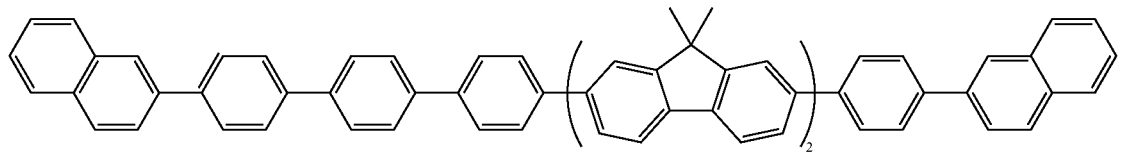
H-302
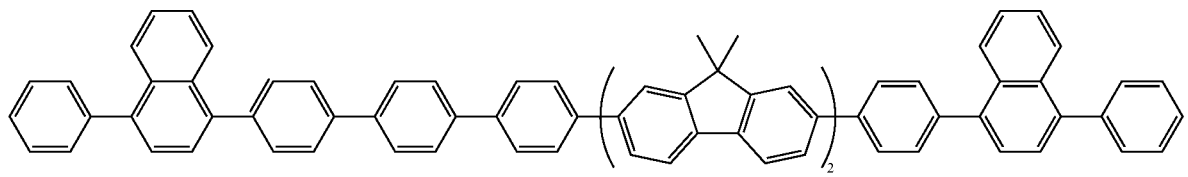
H-303
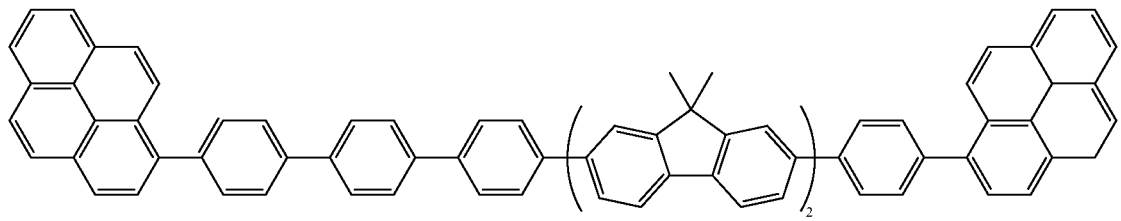
H-304
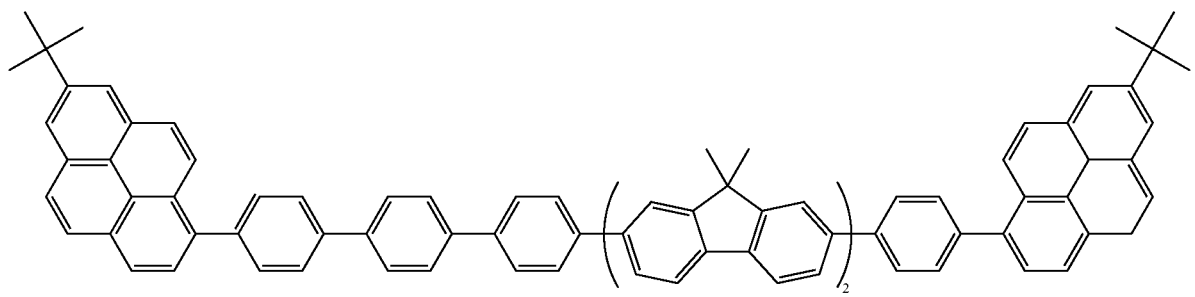
H-305
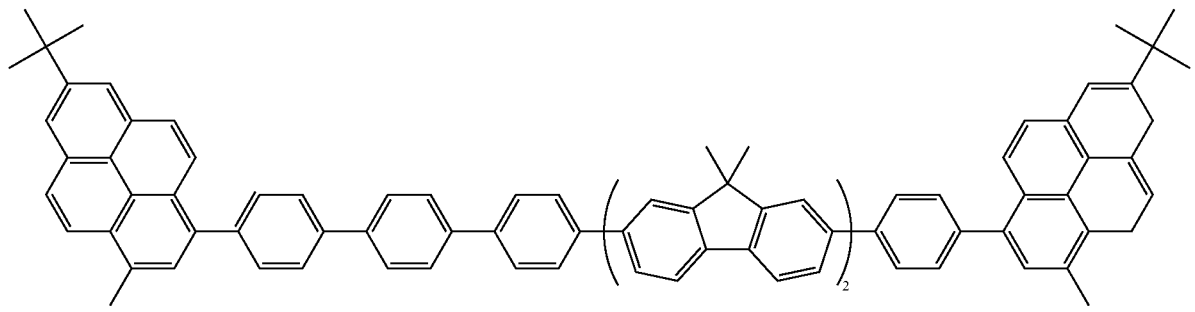
H-306
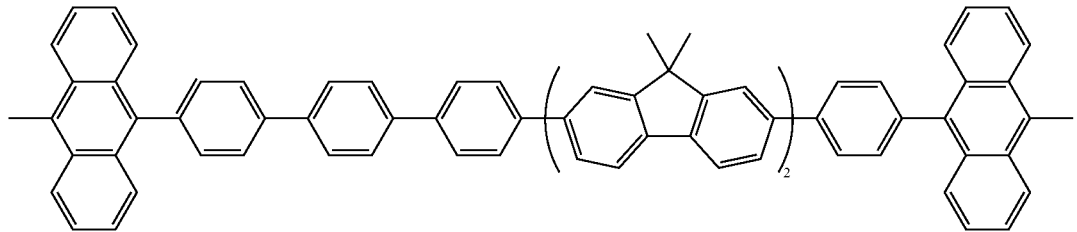

H-307
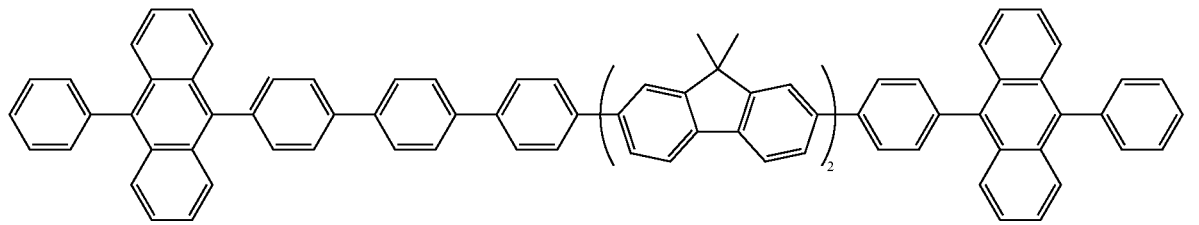
H-308
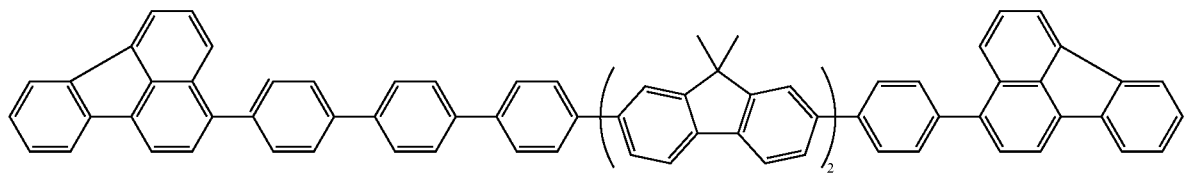
H-309
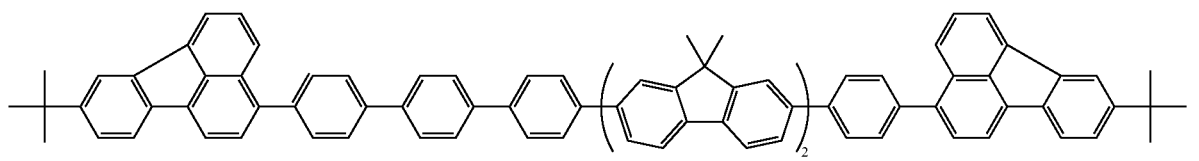
H-310
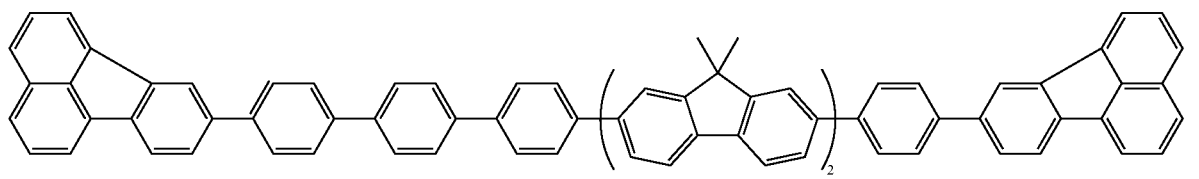
H-311
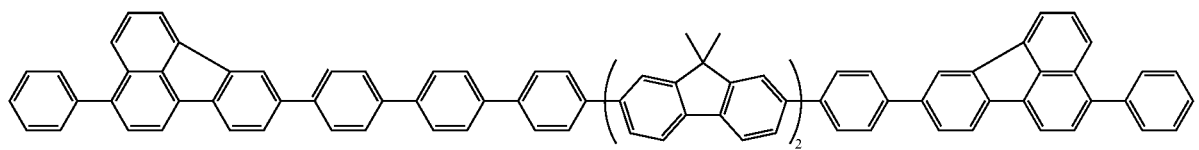
H-312
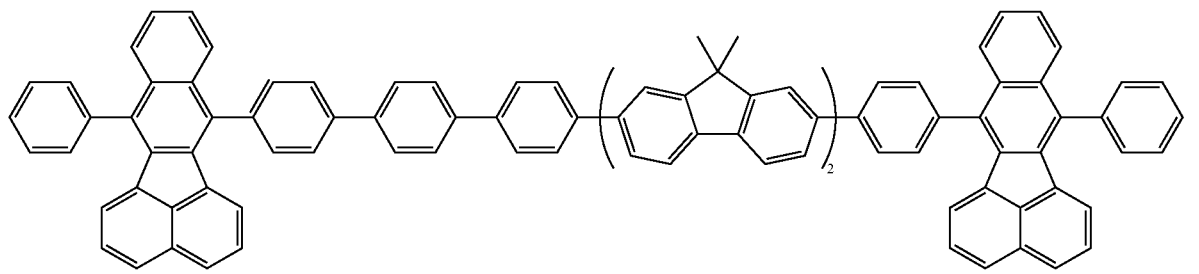
H-313
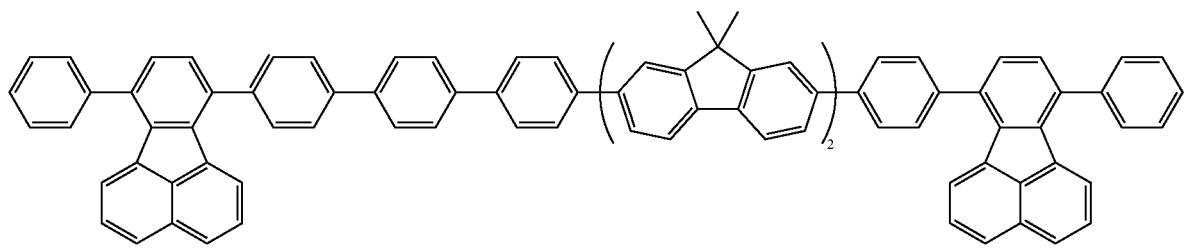

H-314
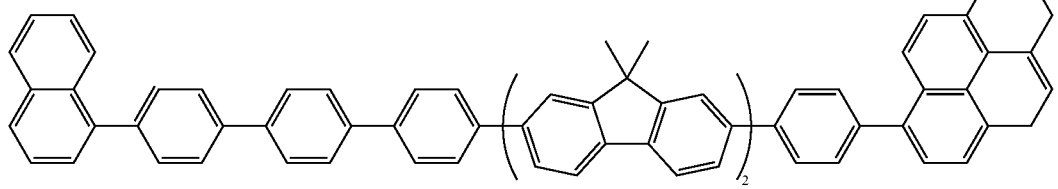
H-315
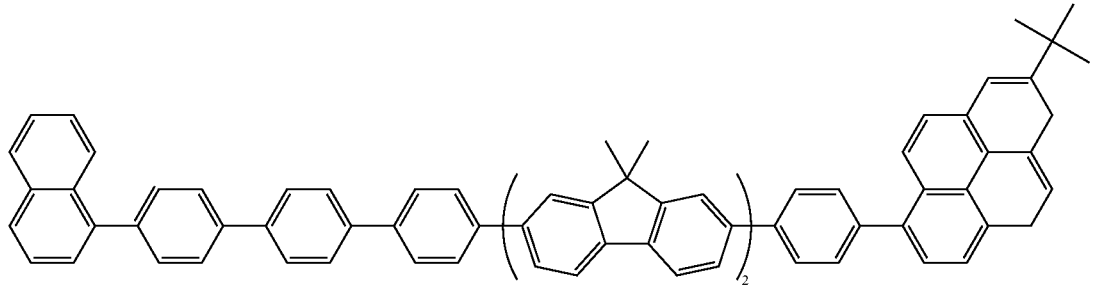
H-316
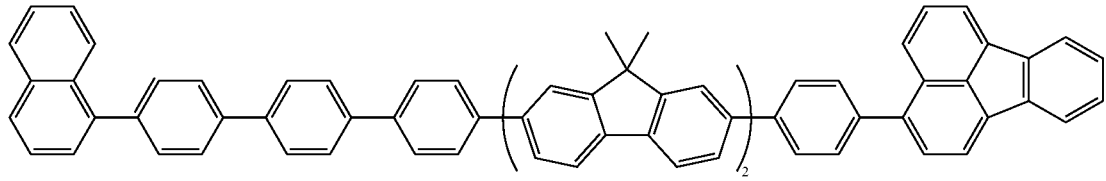
H-317
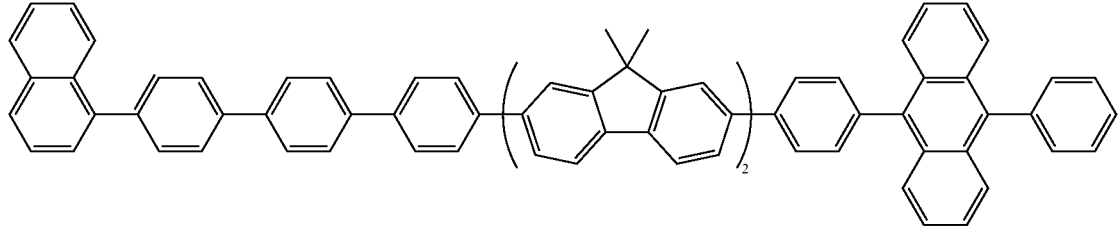
H-318
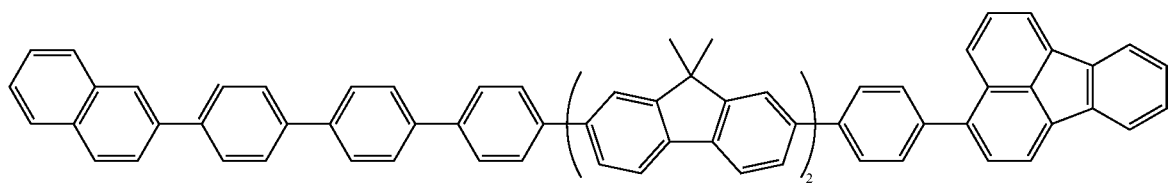
H-319
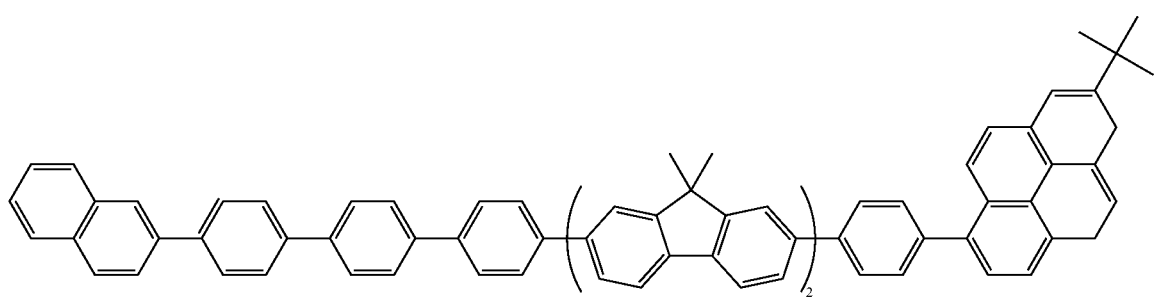

-continued
H-320
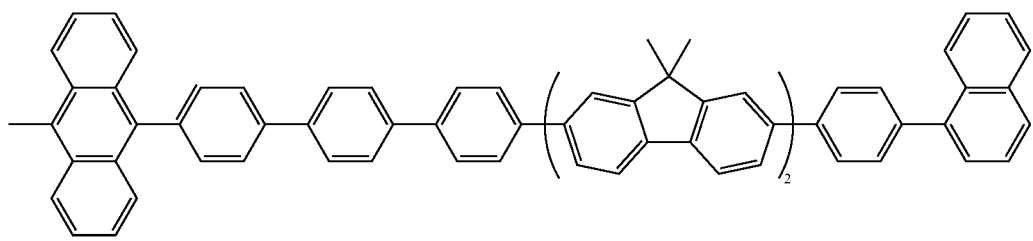
H-321
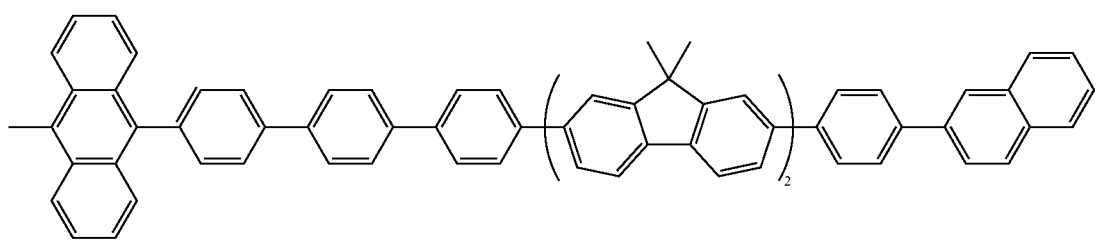
H-322
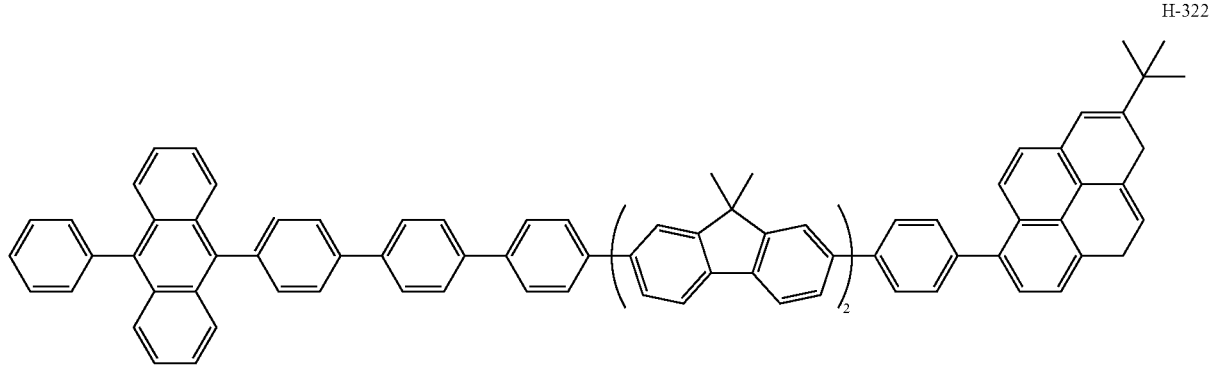
H-323
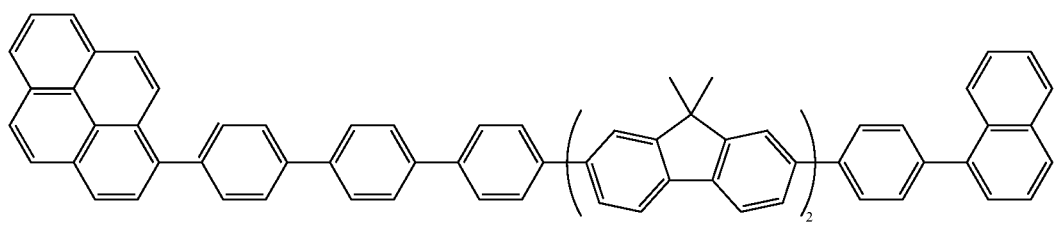
H-324
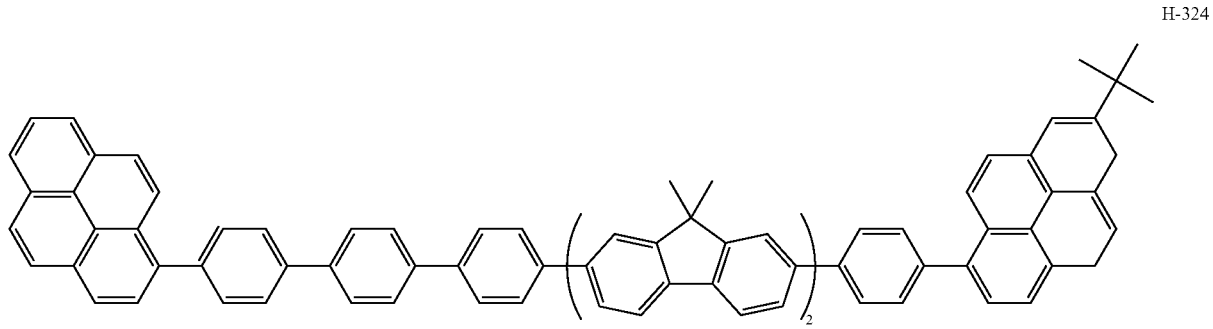
H-325
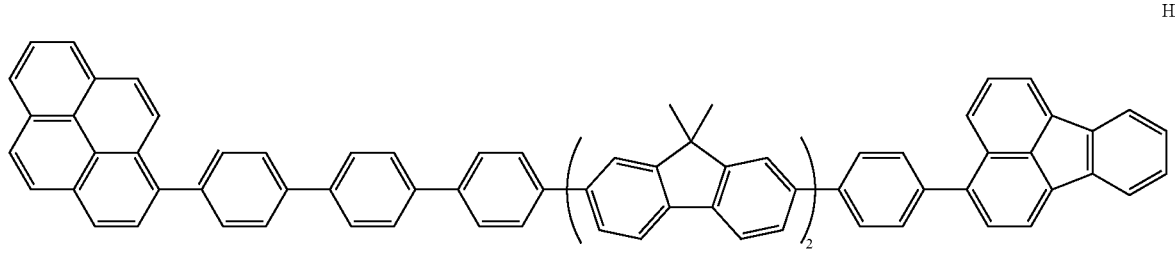

H-326
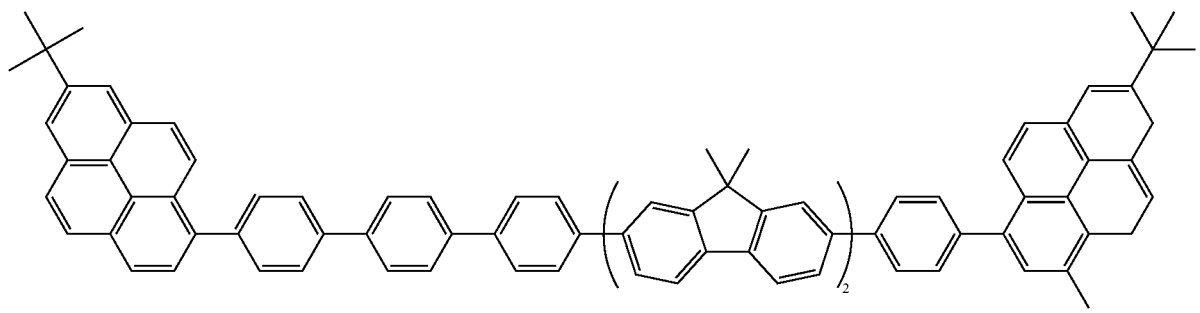
H-327
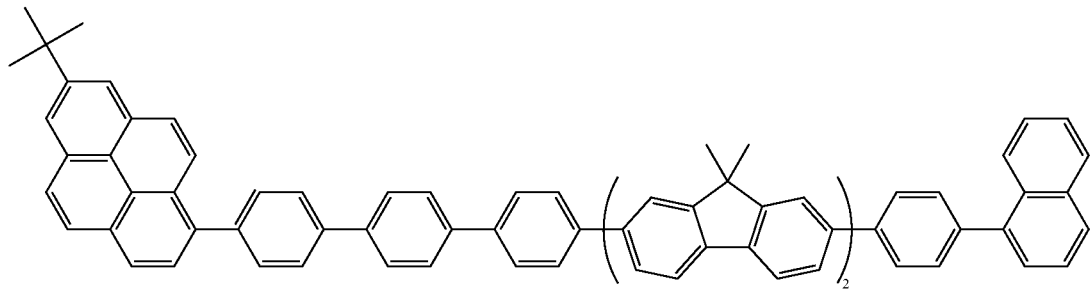
H-328
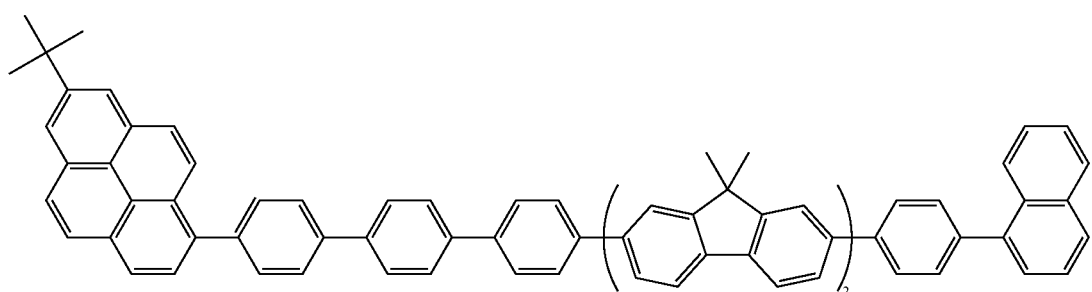
H-329
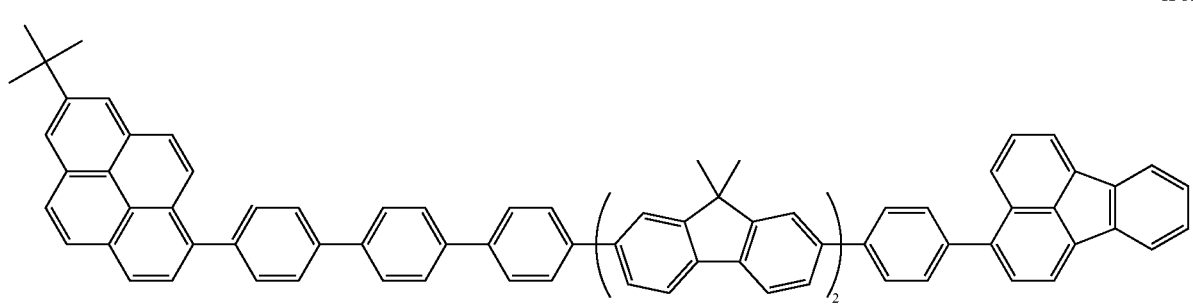
H-330
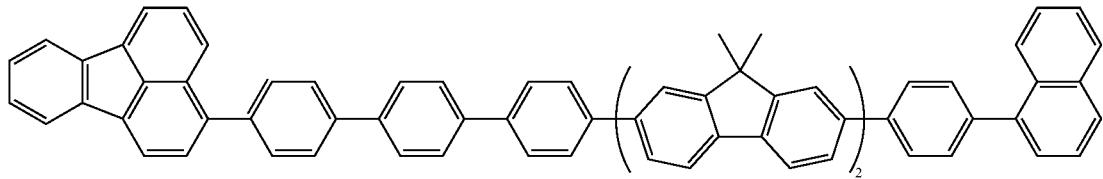
H-331
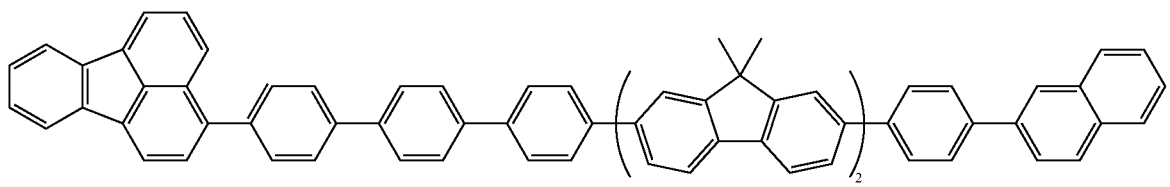

H-332
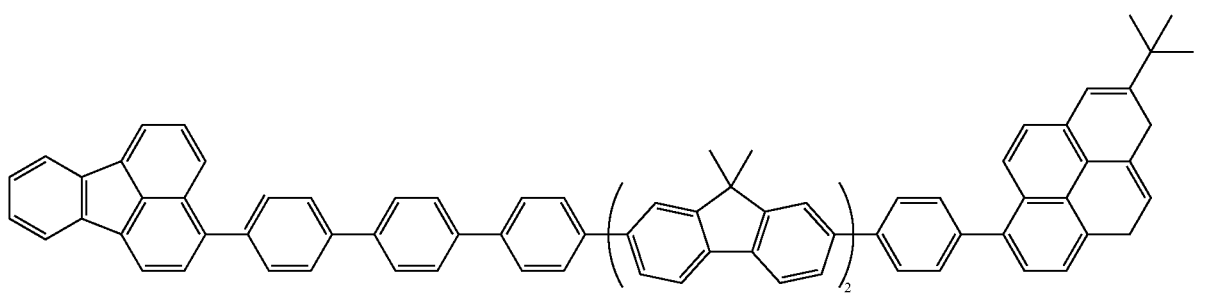
H-333
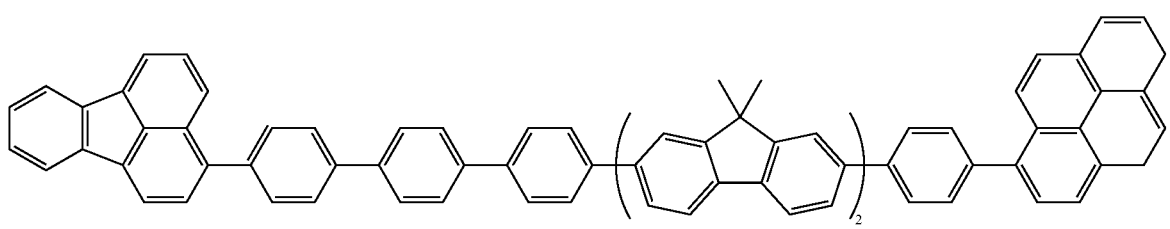
H-334
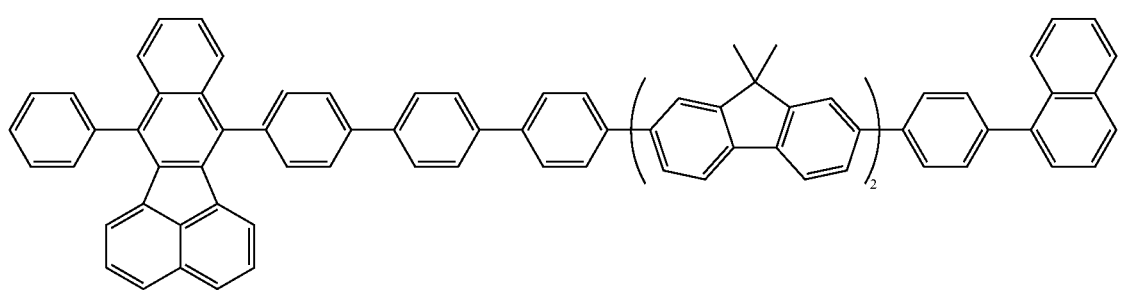
H-335
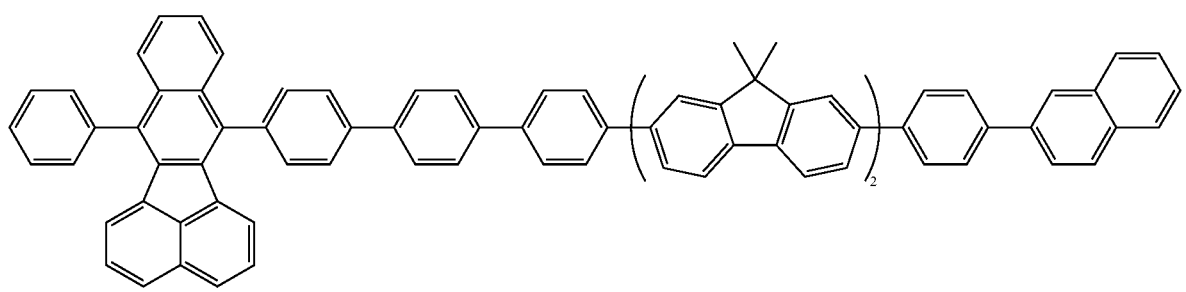
H-336
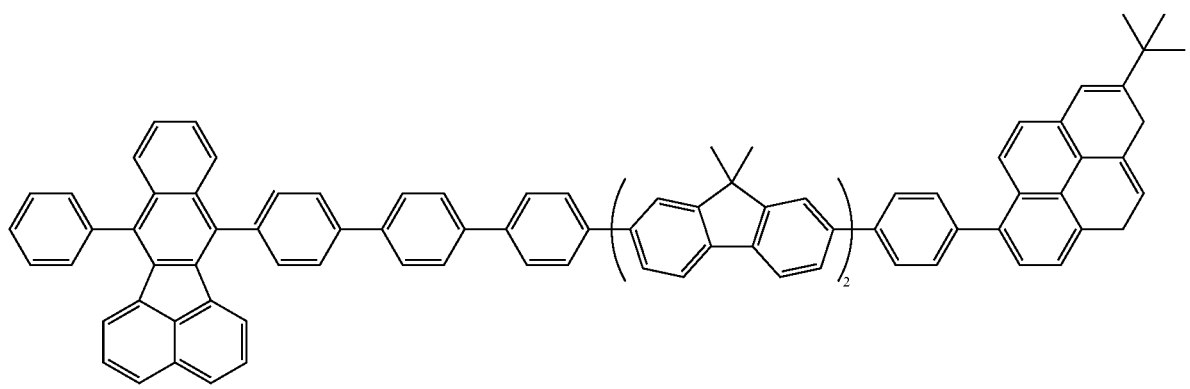

-continued
H-337
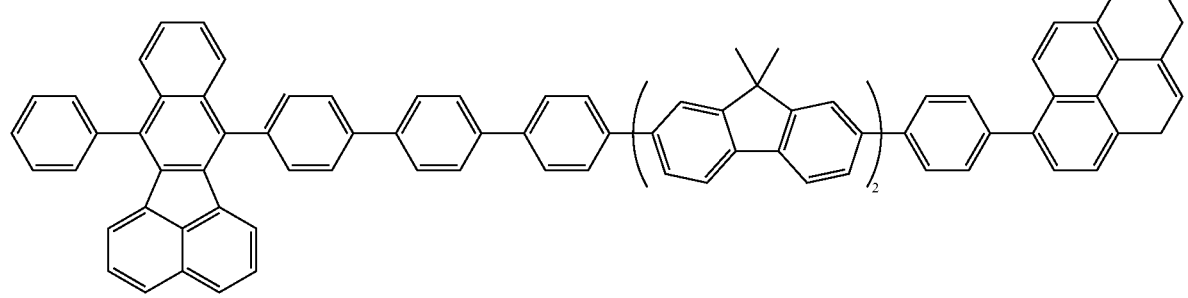
H-338
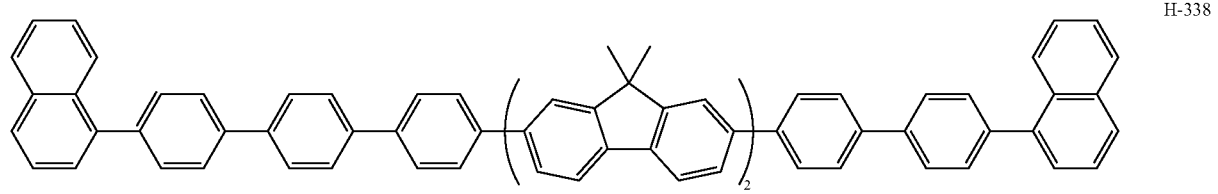
H-339
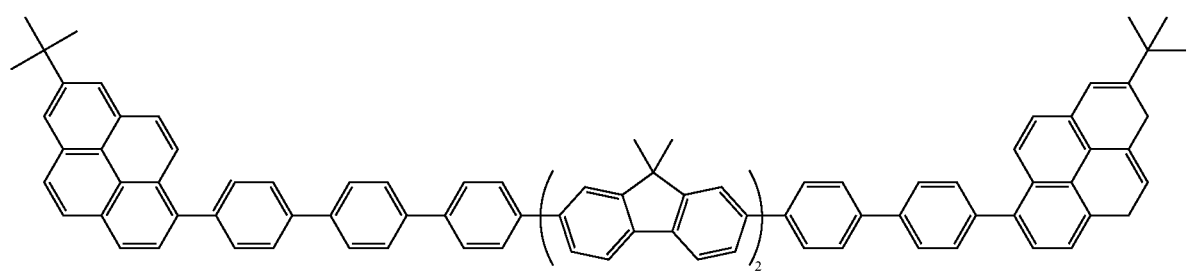
H-340
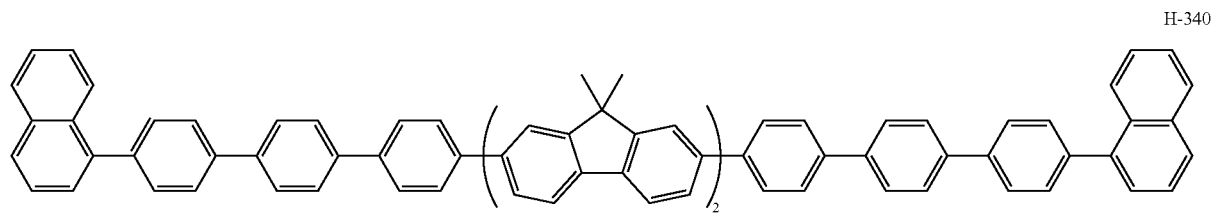
H-341
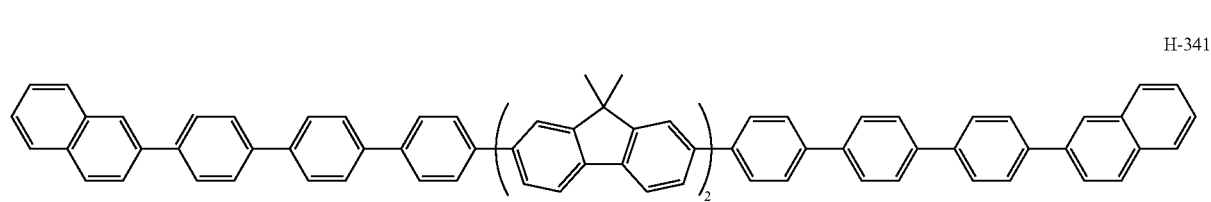
H-342
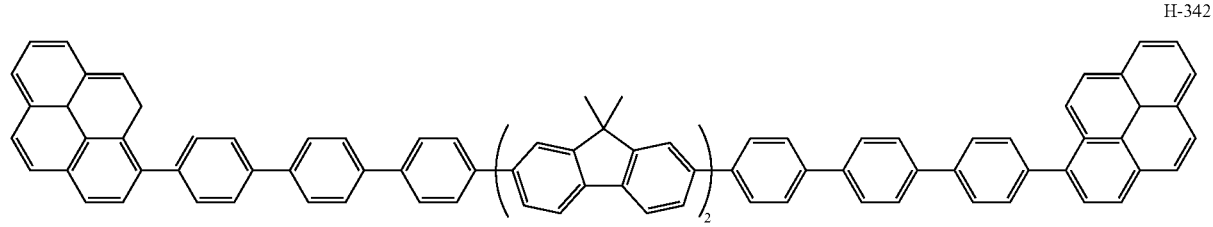

H-343
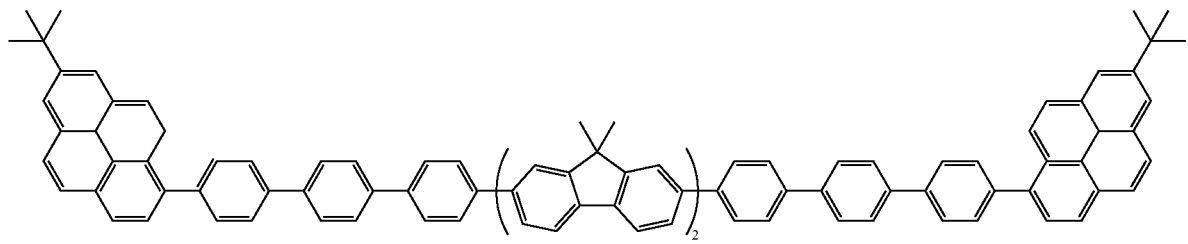
H-344
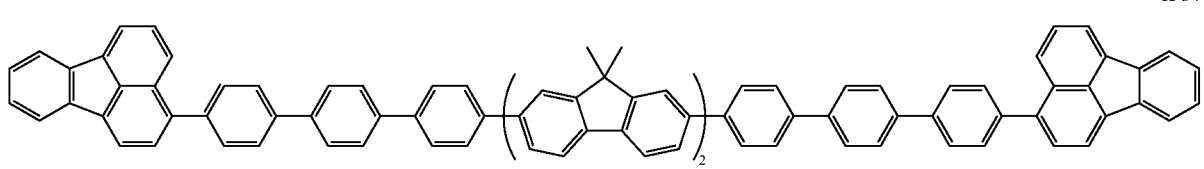
H-345
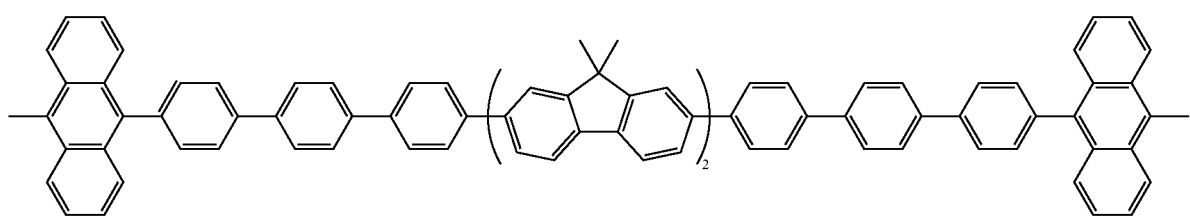
H-346
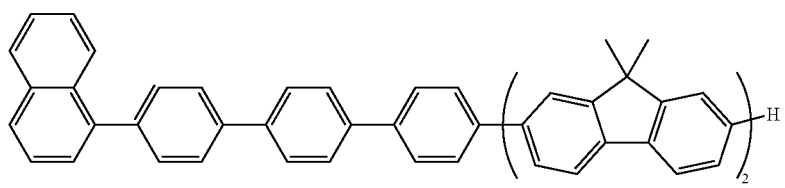
H-347
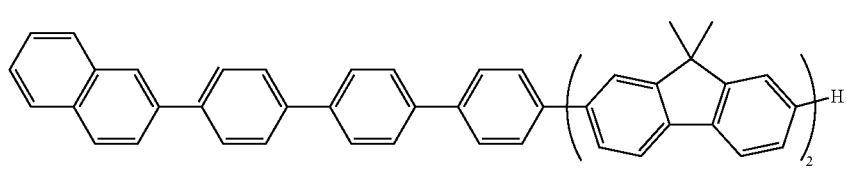
H-348
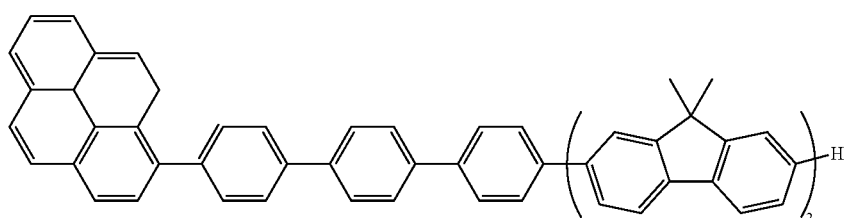
H-349
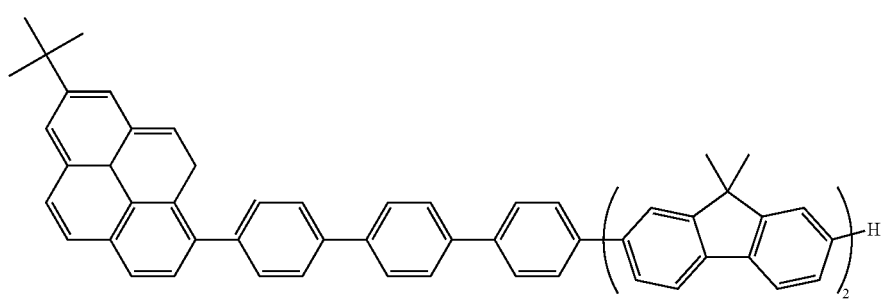

-continued
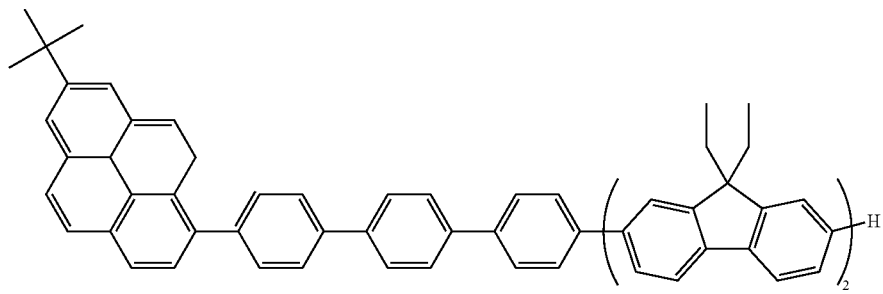
H-350
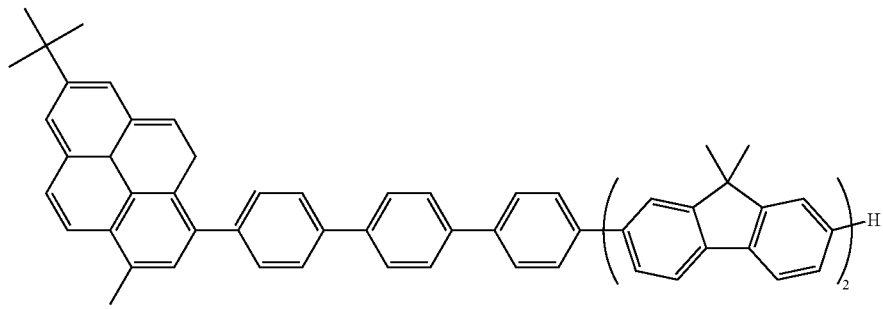
H-351
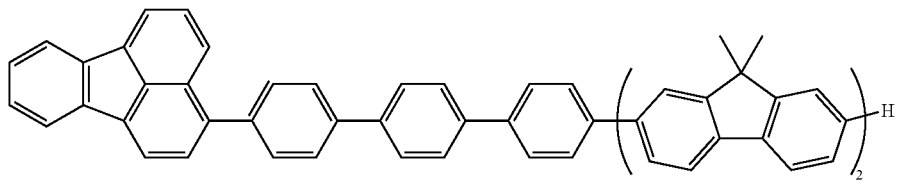
H-352
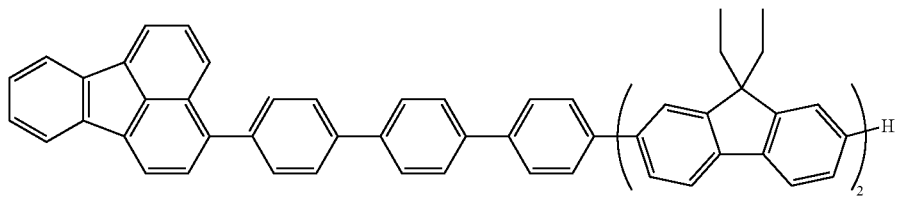
H-353
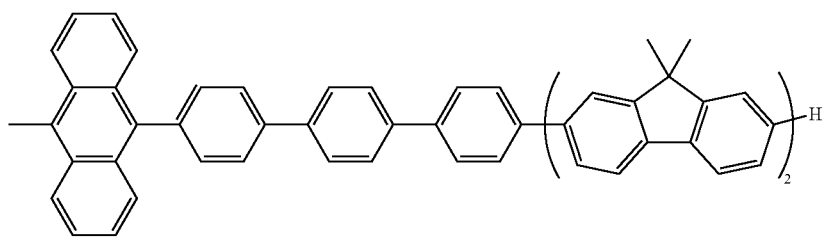
H-354
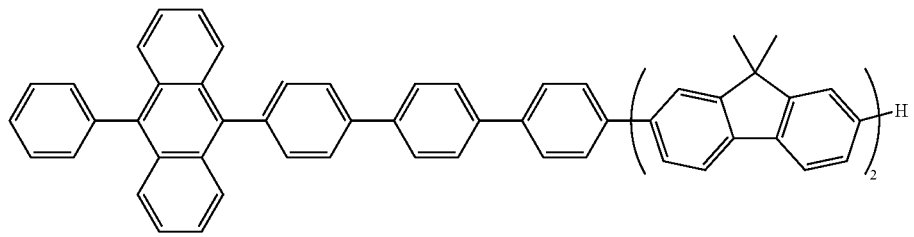
H-355

-continued
H-356
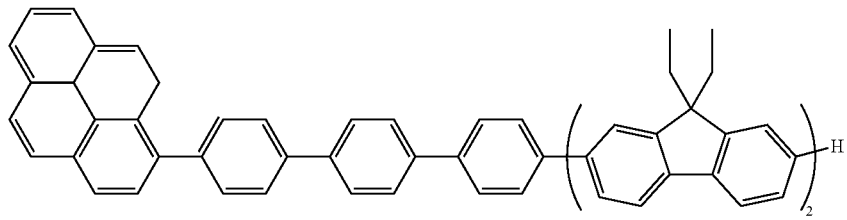
H-357
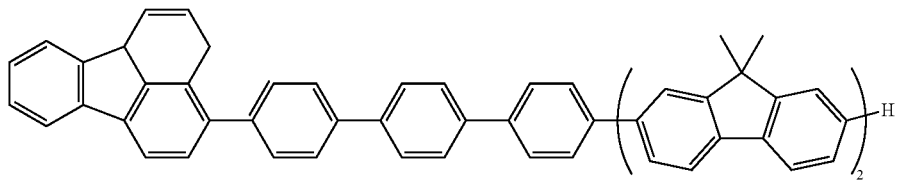
H-358
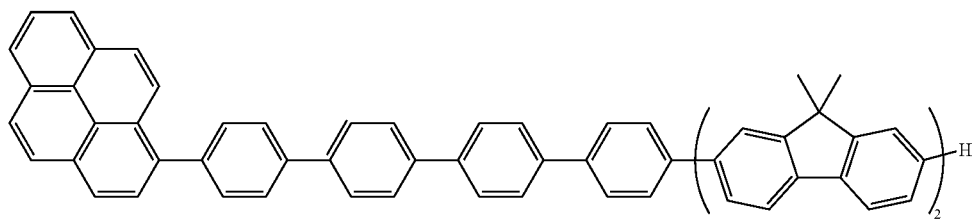
H-359
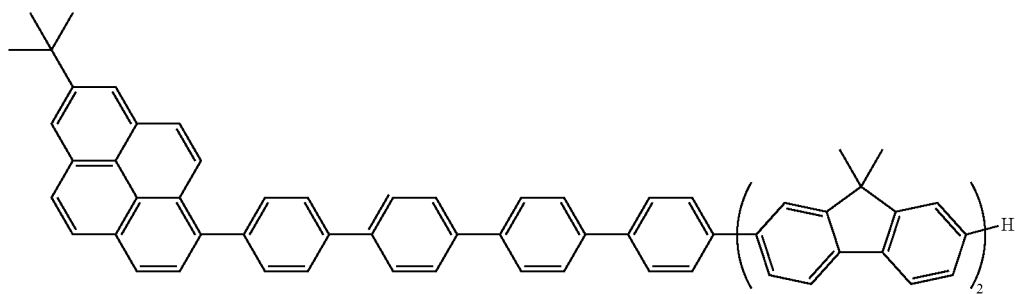
H-360
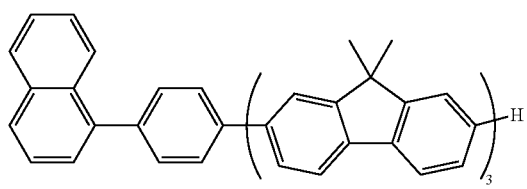
H-361
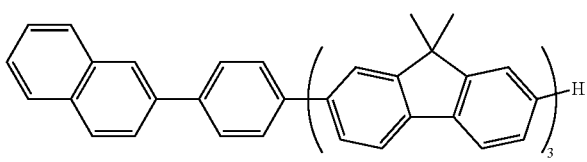
H-362
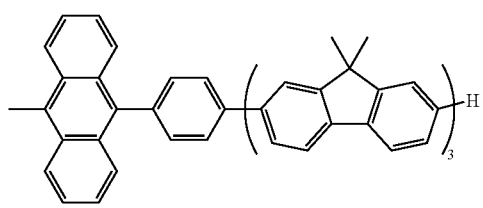
H-363
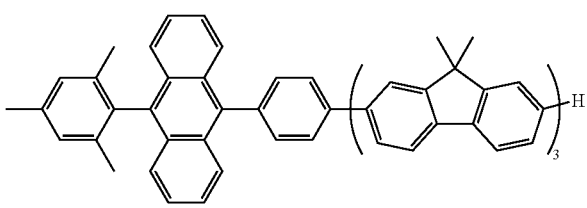
H-364
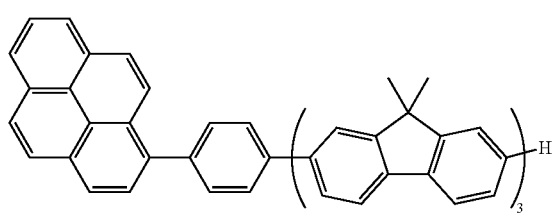
H-365
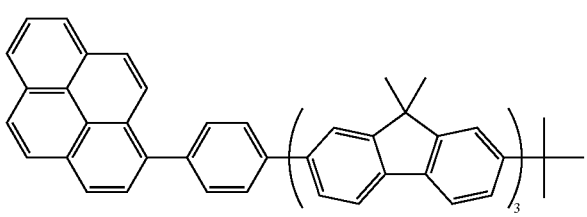

H-366
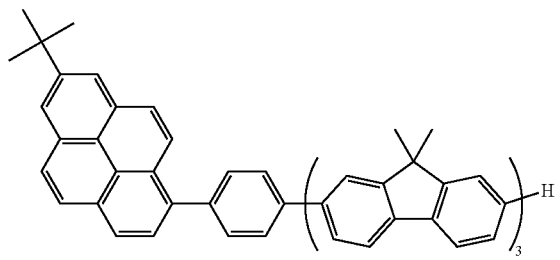
H-367
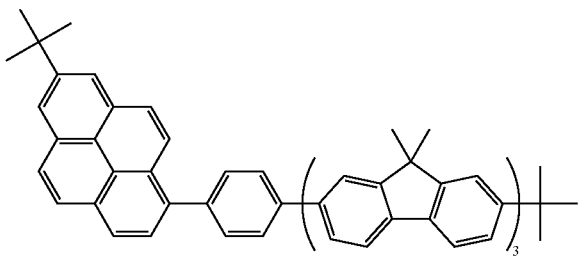
H-368
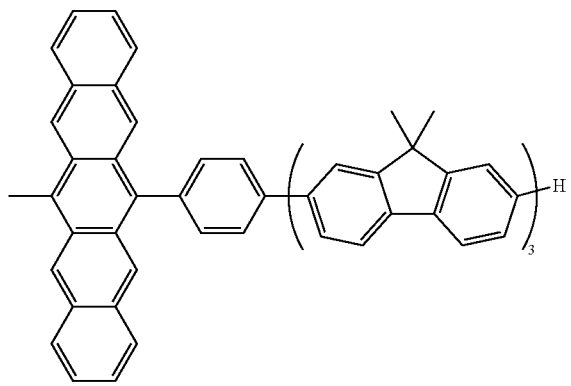
H-369
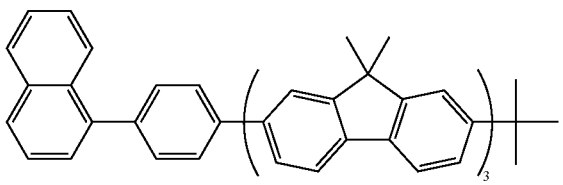
H-370
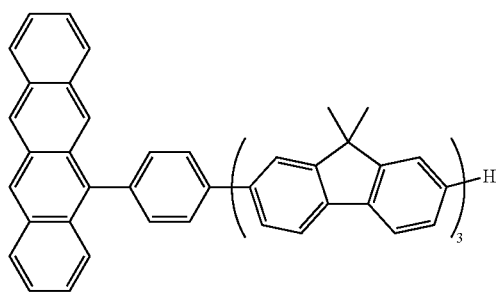
H-371
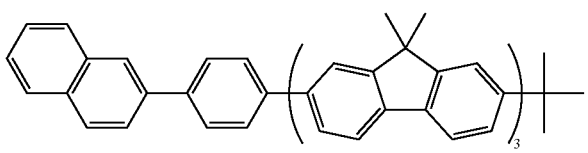
H-372
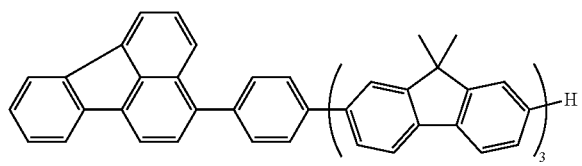
H-373
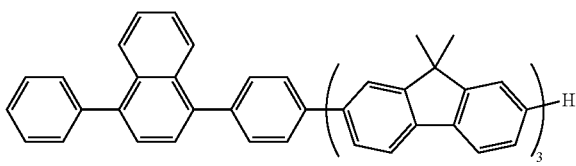
H-374
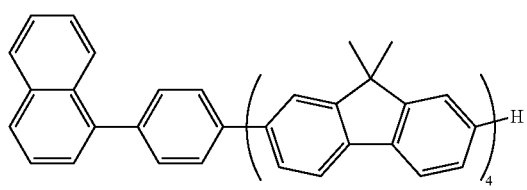
H-375
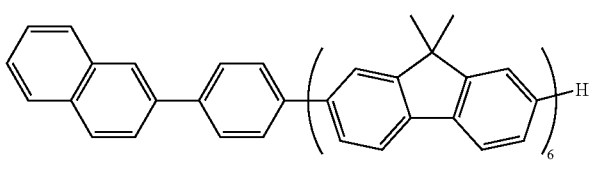
H-376
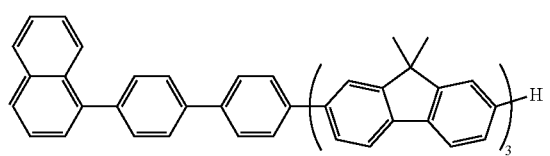
H-377

H-378
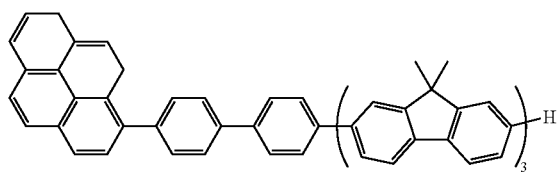
H-379
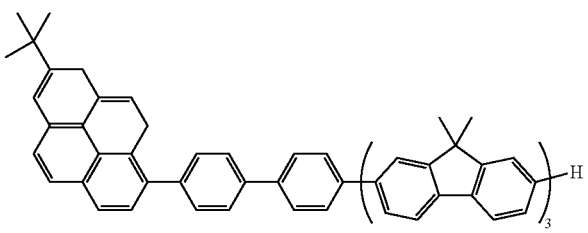
H-380
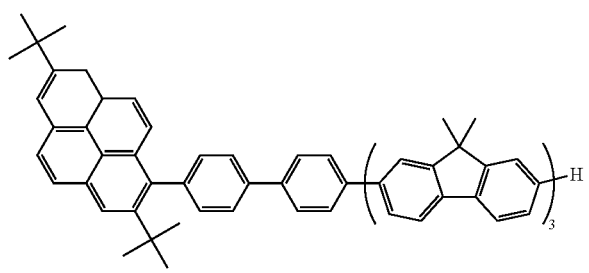
H-381
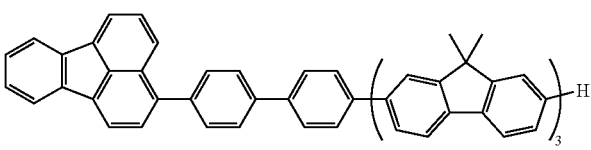
H-382
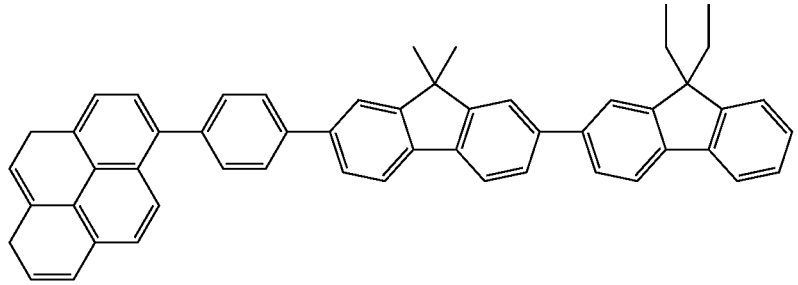
H-383
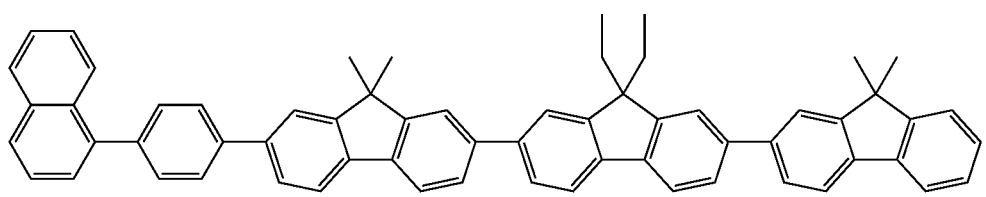
H384
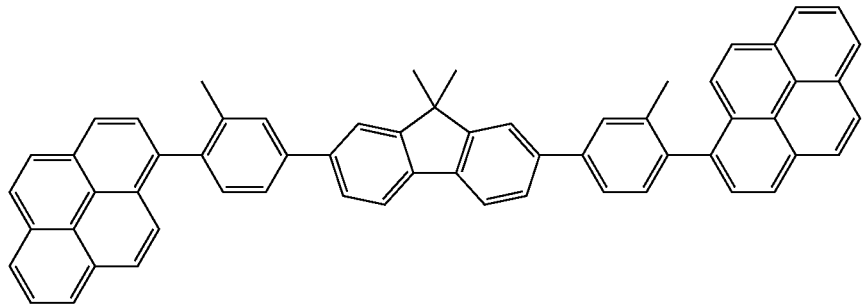
H385
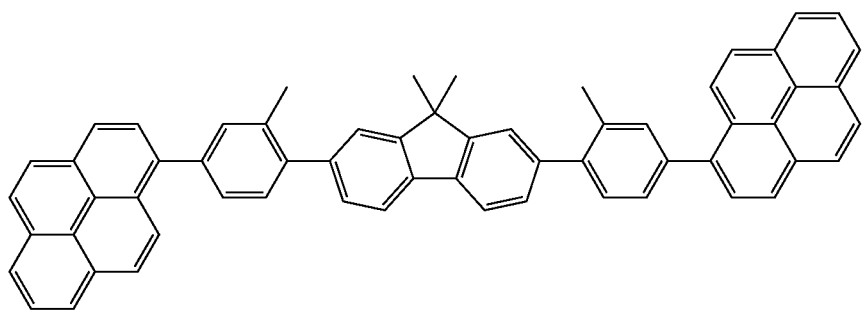

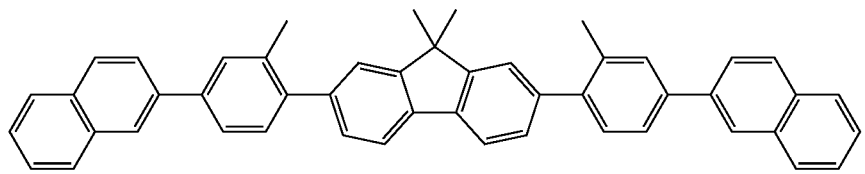

H386

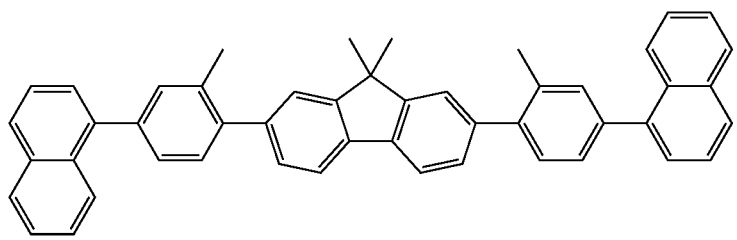

H387

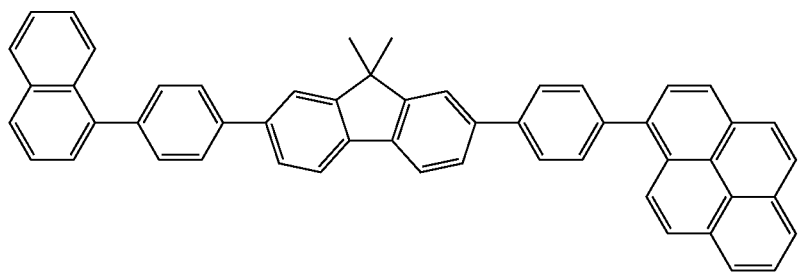

H388

The fluorene compound of the present invention can be synthesized by a Suzuki coupling reaction by appropriately combining a fluorene derivative, a halogenated benzene derivative, and a benzene boric acid derivative.

Next, an organic electroluminescence device of the present invention will be described.

The device of the present invention is an organic electroluminescence device including a layer containing an organic compound, the layer being interposed between a pair of electrodes. The layer containing an organic compound, or preferably a light emitting layer is a layer containing the above-mentioned fluorene compound of the present invention.

It is preferable that: the light emitting layer be composed of two or more compounds including a host and a guest; and the host be the fluorene compound of the present invention. A generally known fluorescent material or phosphorescent material can be used as a guest molecule in this case. In order that a light emitting device having high efficiency may be obtained, a metal coordination compound known to emit phosphorescence such as an Ir complex, a Pt complex, an Re complex, a Cu complex, an Eu complex, or an Rh complex is preferable, and an Ir coordination compound known to emit strong phosphorescence is more preferable. Further, a plurality of phosphorescent materials can be incorporated into the light emitting layer for the purposes of causing the light emitting layer to emit plural light beams different from each other in color and aiding the transmission of an exciton or charge.

In addition, in the device of the present invention, the light emitting layer may be composed of two or more compounds including a host and a guest, and the guest may be the fluorene compound of the present invention. In this case, light emitted from the guest is preferably fluorescence. Further, plural fluorescent materials can be incorporated into the light emitting layer for the purposes of causing the light emitting layer to emit plural light beams different from each other in color and aiding the transmission of an exciton or charge.

An organic layer containing the fluorene compound of the present invention can be produced by, for example, a vacuum deposition method, a cast method, an application method, a spin coating method, an ink-jet method, or a laminate method.

Examples of an electron transport material, a hole transport material, and the like are shown below. However, the electron transport material, the hole transport material, and the like are not limited to the examples.

121 122
E-1
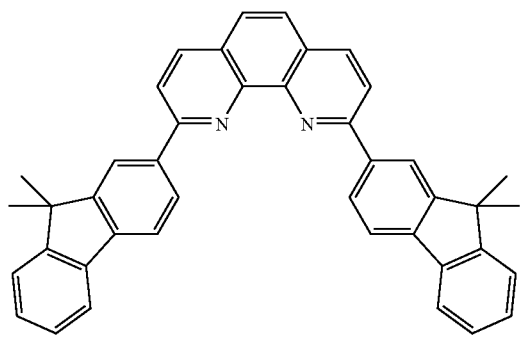
E-2
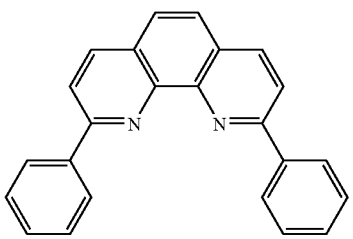
E-3
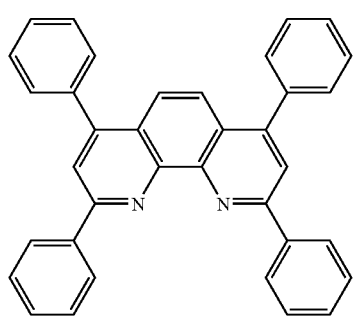
E-4
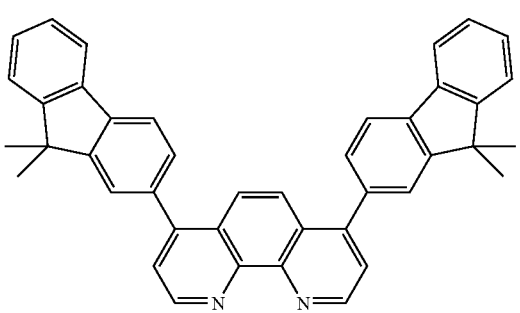
E-5
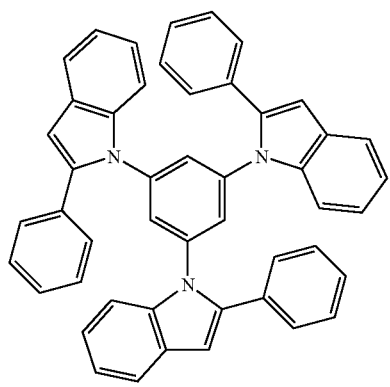
HT-1
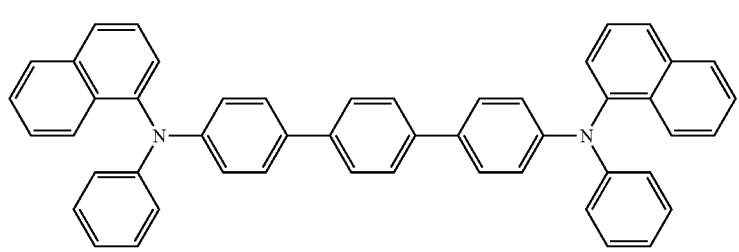
HT-2
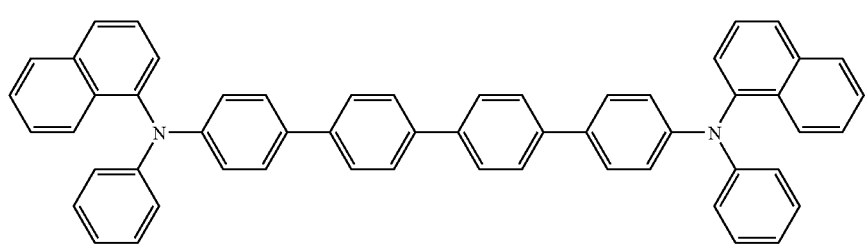

HT-3
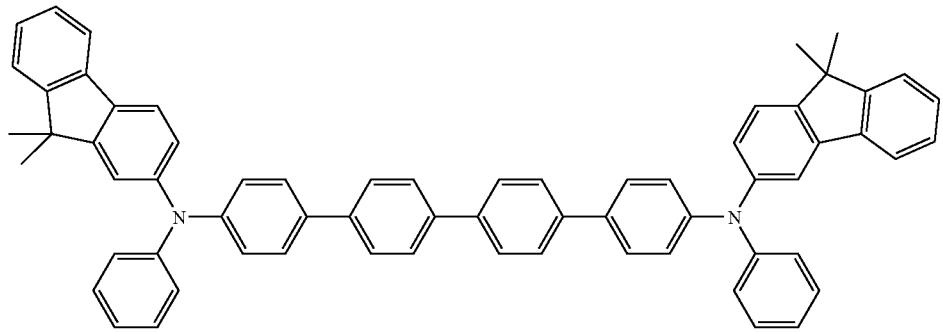
HT-4
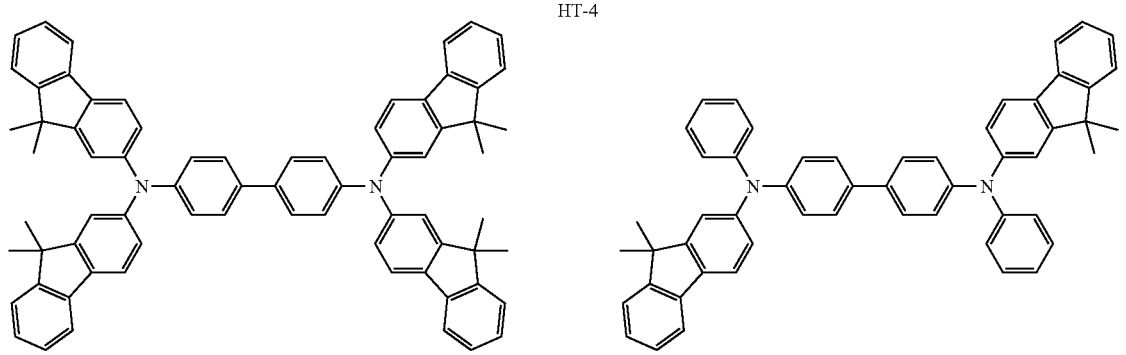
HT-5
HT-6
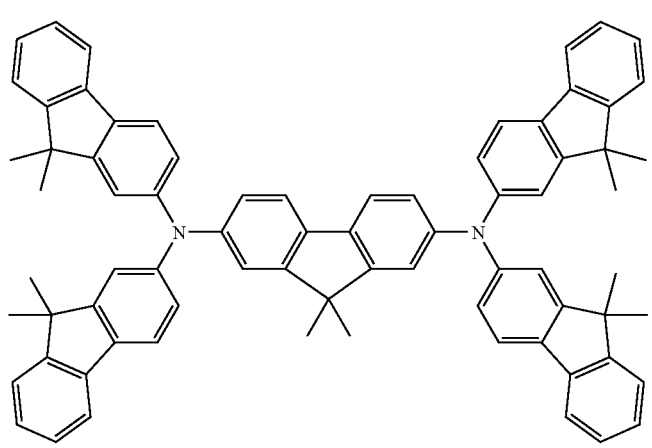
HT-7
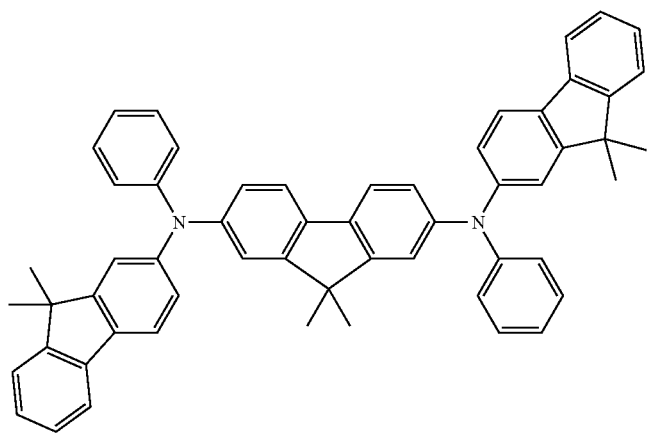

-continued
HT-8
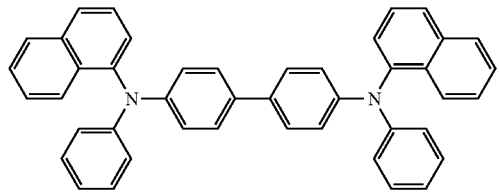
HT-9
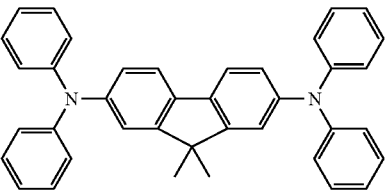
HT-10
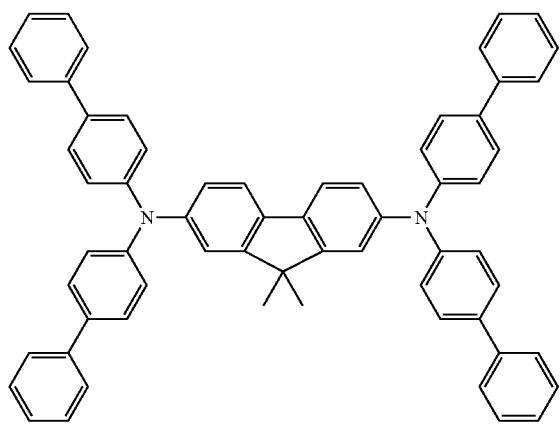
In addition, examples of a luminescent dopant that can be used in combination with the compound of the present invention are shown below. However, the luminescent dopant is not limited to the examples.
D-1
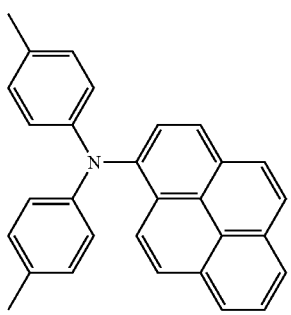
D-2
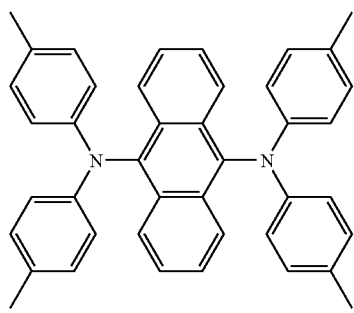
-continued
D-3
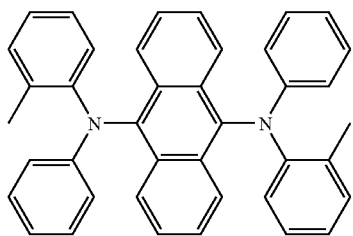
D-4
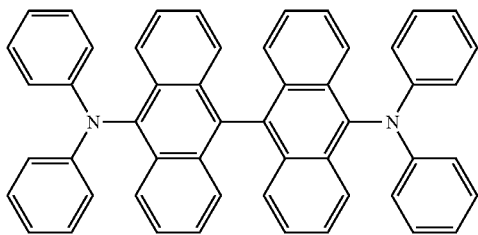
D-5
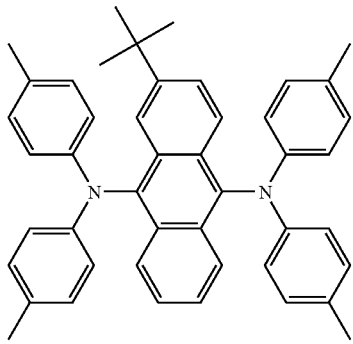

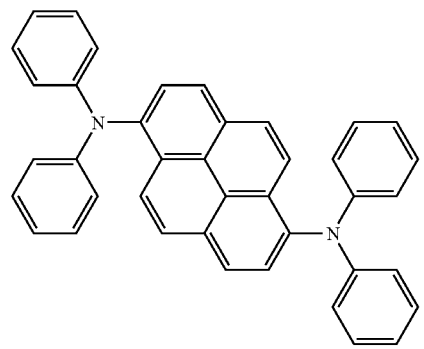
D-6
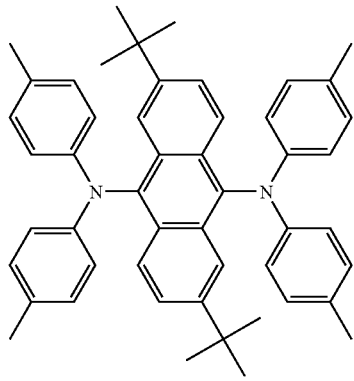
D-10
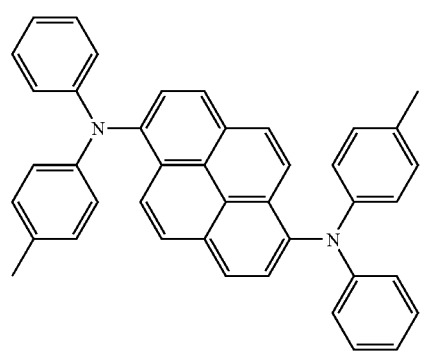
D-7
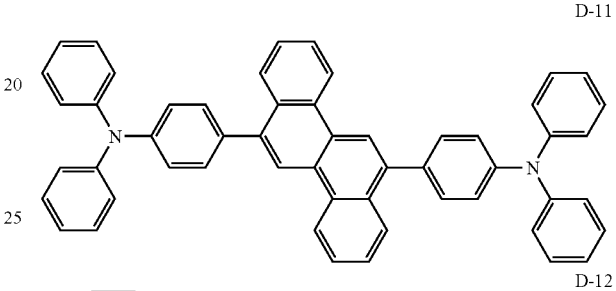
D-11
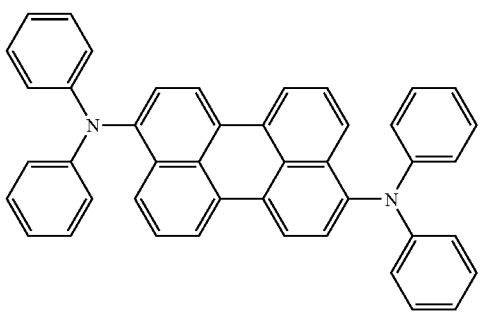
D-12
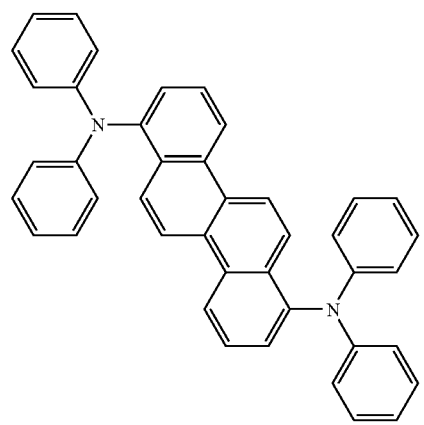
D-8
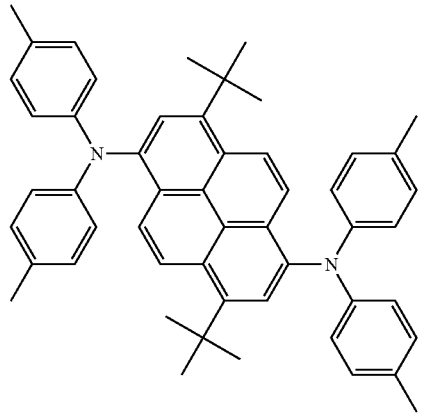
D-13
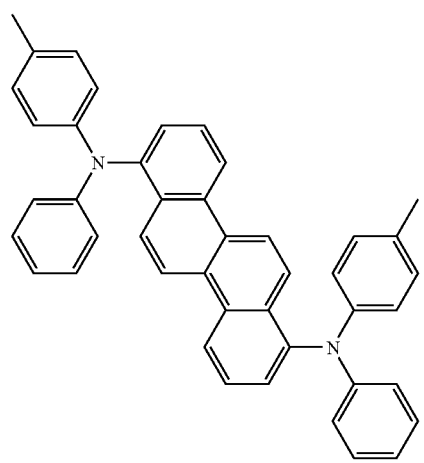
D-9
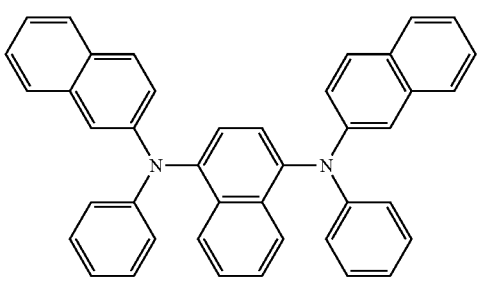
D-14

-continued
D-15
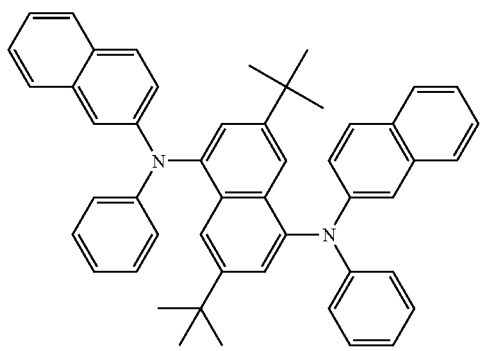
D-16
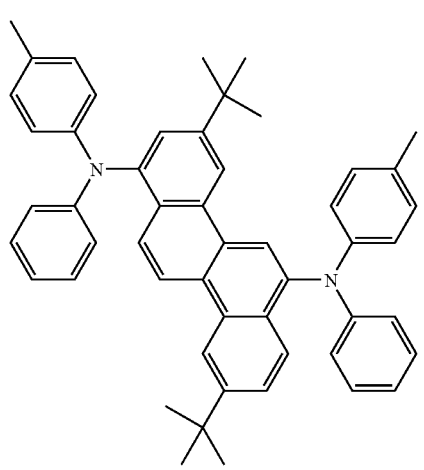
D-17
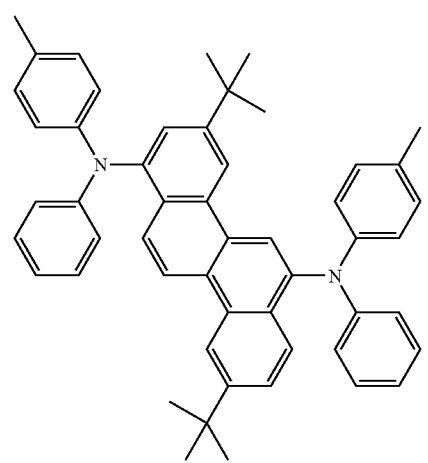
D-18
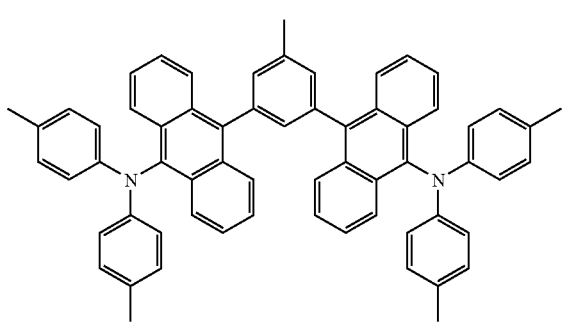
-continued
D-19
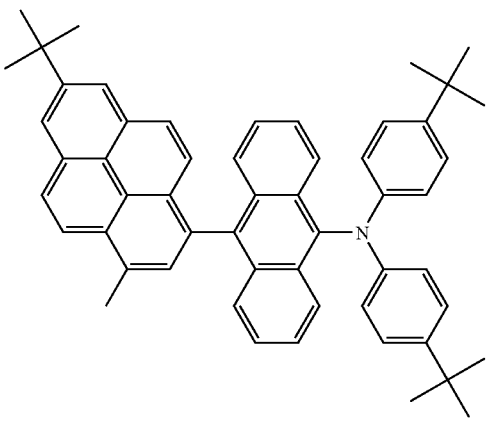
D-20
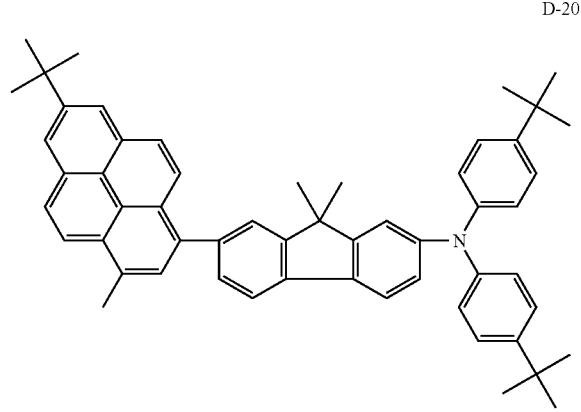
D-21
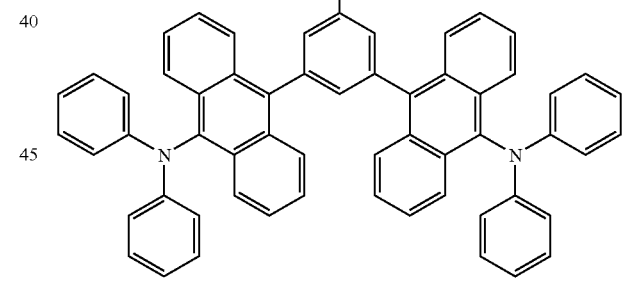
D-22
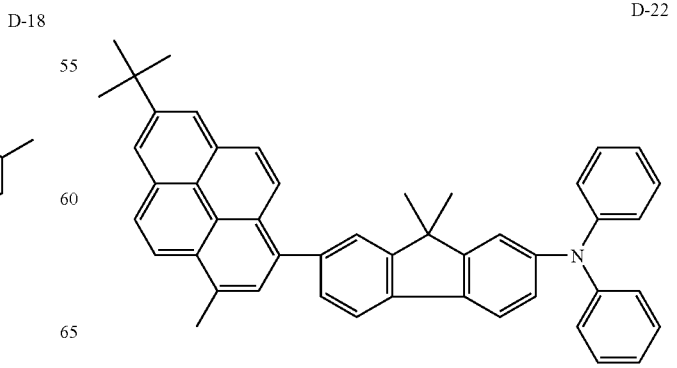

-continued
D-23
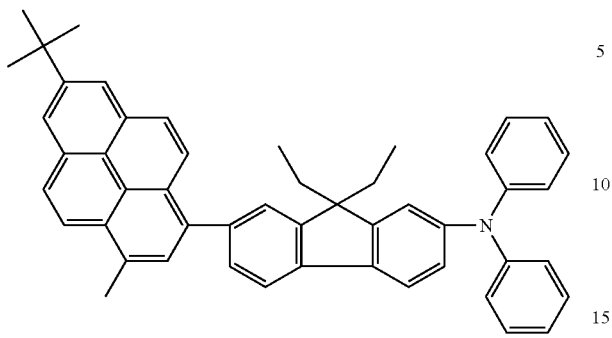
D-24
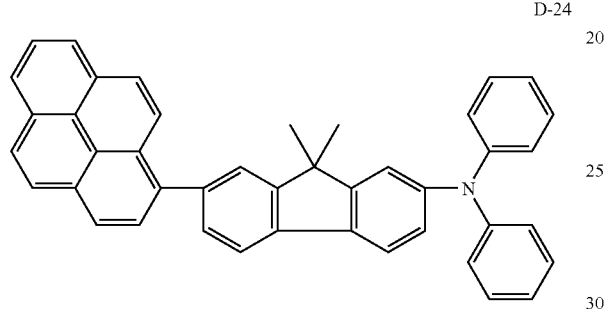
D-25
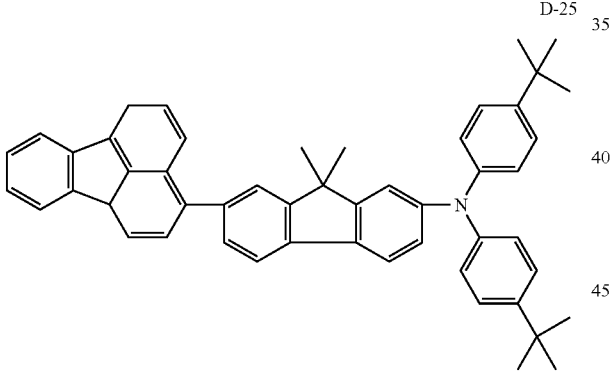
D-26
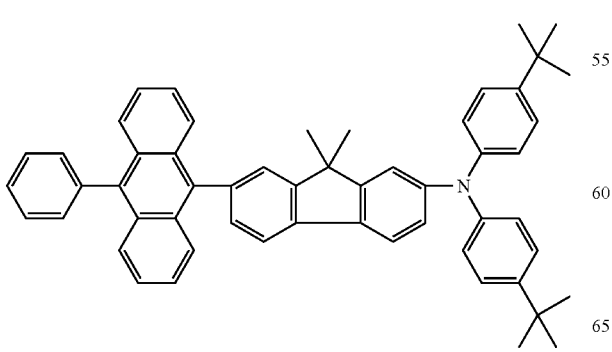
-continued
D-27
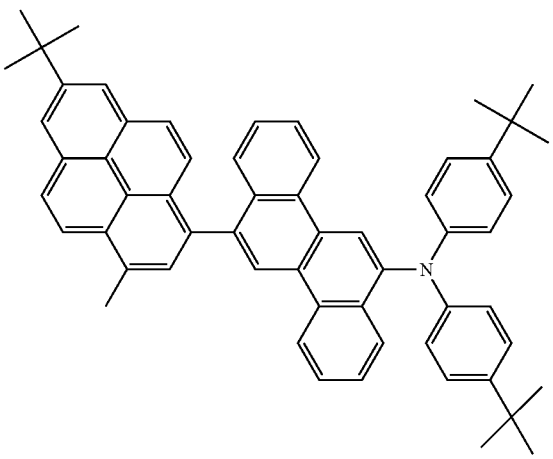
D-28
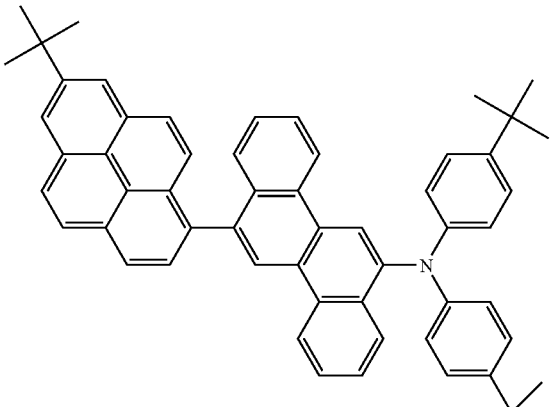
D-29
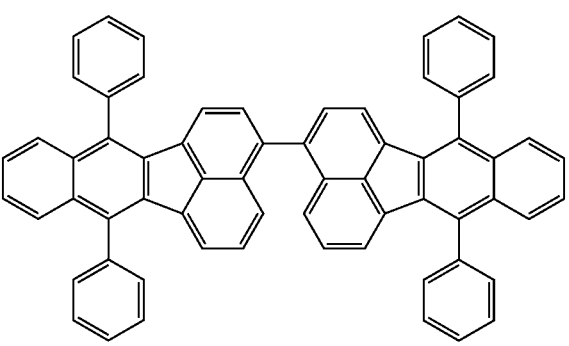
D-30
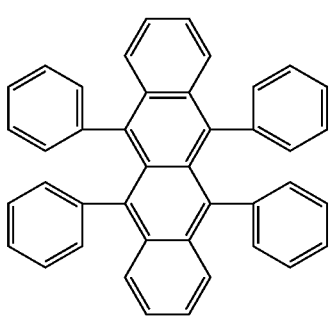

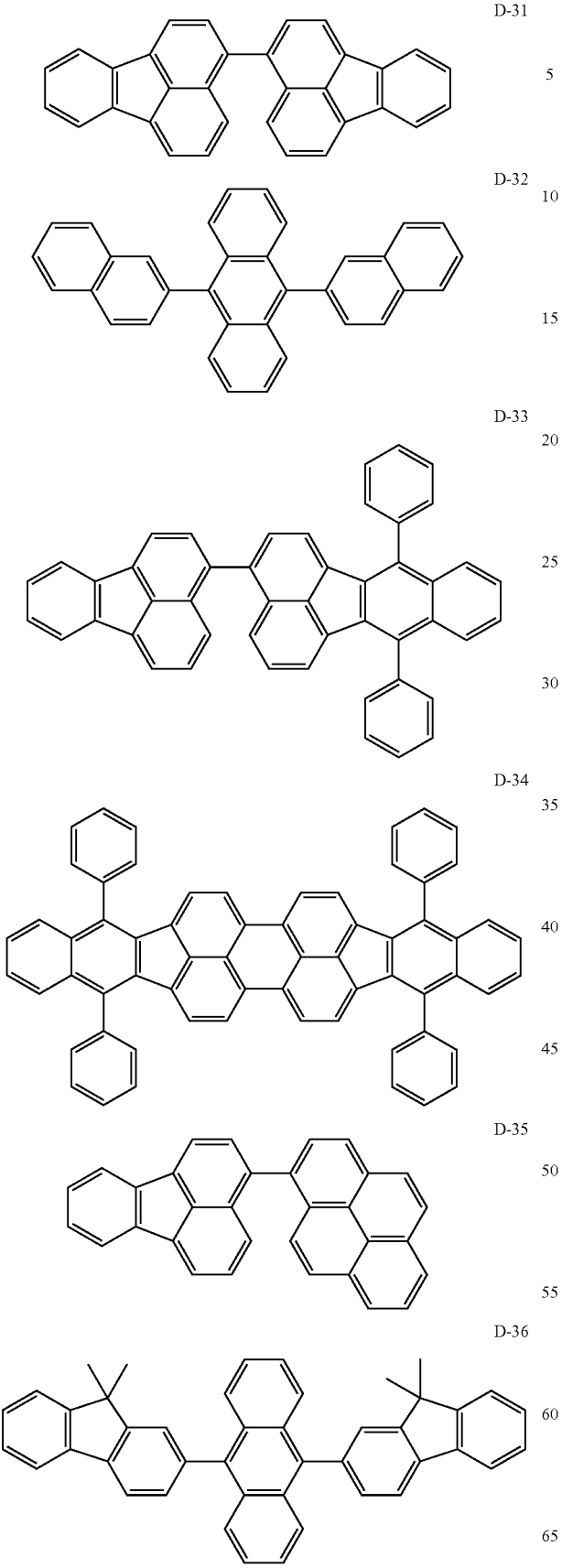

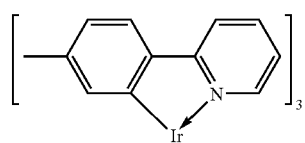
D45
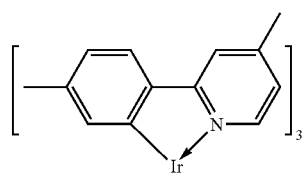
D46
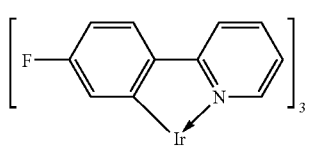
D47
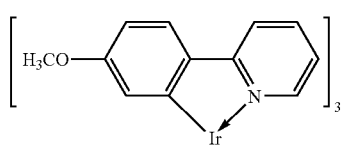
D48
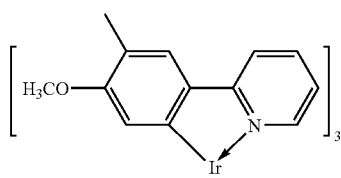
D49
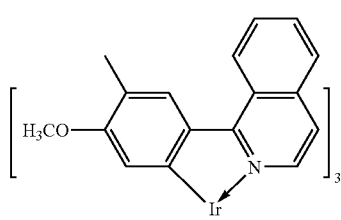
D50
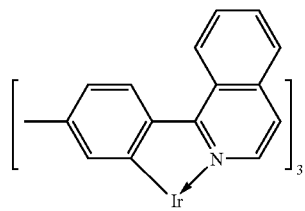
D51
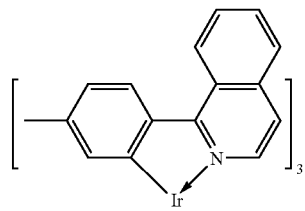
D52
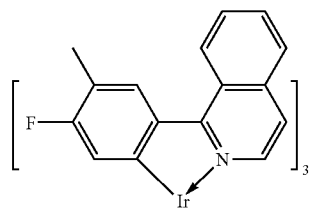
D53
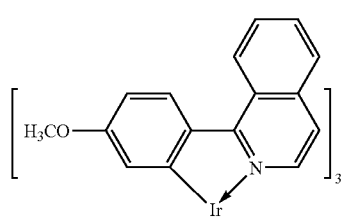
D54
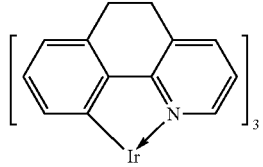
D55
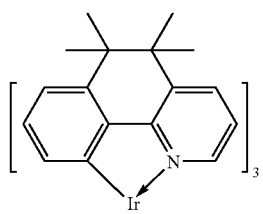
D56
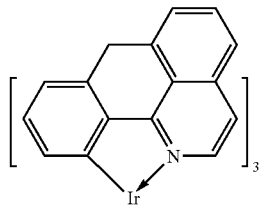
D57
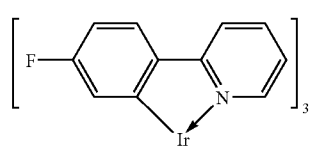
D58

Figure 1B:
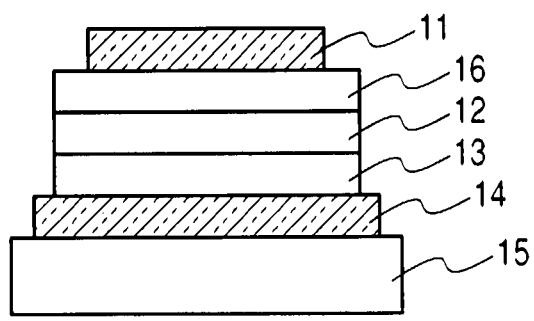
Figure 1C:
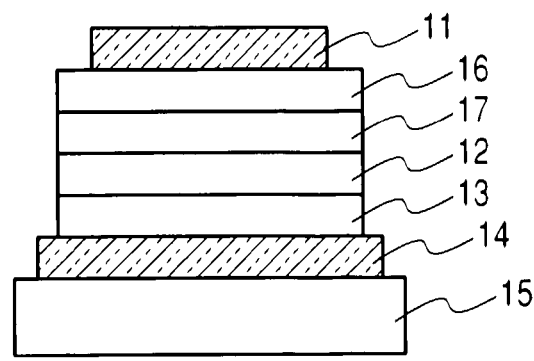

FIGS. 1A to 1C each show an example of the constitution of the device of the present invention.

FIG. 1A shows an example in which organic layers are composed of a light emitting layer 12 and a hole transport layer 13.

ITO or the like having a large work function is used in a transparent electrode 14, thereby facilitating the injection of a hole from the transparent electrode 14 into the hole transport layer 13. A metal material having a small work function such as aluminum, magnesium, or an alloy using any one of them is used in a metal electrode 11, thereby facilitating the injection of an electron into each organic layer.

The fluorene compound of the present invention is preferably used in the light emitting layer 12. A material having electron donating property such as a triphenyldiamine derivative typified by α-NPD can be appropriately used in the hole transport layer 13.

The device constituted as described above shows electrical rectifying property. When an electric field is applied in such a manner that the metal electrode 11 serves as a cathode and the transparent electrode 14 serves as an anode, an electron is injected from the metal electrode 11 into the light emitting layer 12, and a hole is injected from a transparent substrate 15.

The injected hole and the injected electron recombine in the light emitting layer 12 to generate an exciton, whereby light is emitted. In this case, the hole transport layer 13 serves as an electron blocking layer. As a result, the efficiency with which a hole and an electron recombine at an interface between the light emitting layer 12 and the hole transport layer 13 is improved, whereby luminous efficiency is improved.

Further, in FIG. 1B, an electron transport layer 16 is provided between the metal electrode 11 and the light emitting layer 12 shown in FIG. 1A. Luminous efficiency is improved by separating a light emission function, and an electron transport function and a hole transport function to provide a constitution additionally effective in blocking a carrier. An oxadiazole derivative or the like can be used in the electron transport layer 16. It should be noted that the same reference numeral in another figure represents the same member.

In addition, a four-layer constitution shown in FIG. 1C is also desirable, which is composed of the hole transport layer 13, the light emitting layer 12, an exciton diffusion preventing layer 17, the electron transport layer 16, and the metal electrode 11 laminated in the stated order from the side of the transparent electrode 14 as an anode.

Hereinafter, the present invention will be described specifically by way of examples. However, the present invention is not limited to these examples.

It should be noted that an intermediate used in the synthesis of the fluorene compound of the present invention was synthesized in accordance with the following procedure.

That is, 2-halogeno-9H-fluorene and 2,7-dihalogeno-9H-fluorene were synthesized with reference to "Bull. Chem. Soc. Jpn. 62 (1989) 439" (Document 1). Next, the dimethylation of 9-positions of the fluorenes was performed in DMF by using CH$_3$Cl and NaOCH$_3$, whereby 2-halogeno-9-dimethylfluorene and 2,7-dihalogeno-9-dimethylfluorene were obtained. Further, boric acid or pinacol borate was synthesized with reference to "ORGANIC SYNTHESES VIA BORANES Volume 3" (Document 2). The resultant compound was subjected to an appropriate combination of Suzuki coupling (Document 2), halogenation (Document 1), and the synthesis of boric acid, whereby the following reaction intermediate (where n represents an integer of 1 to 5) was synthesized.

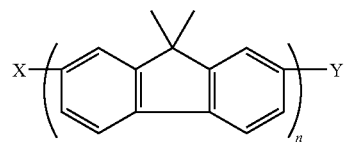

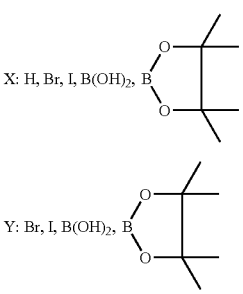

X: H, Br, I, B(OH)$_2$, B

Y: Br, I, B(OH)$_2$, B

EXAMPLE 1

Synthesis of Exemplified Compound No. H-184

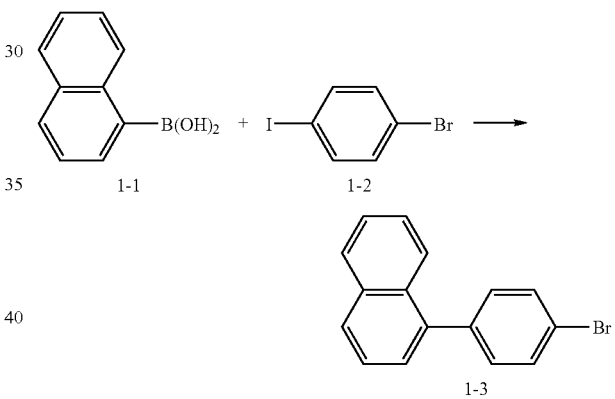

The following components were loaded into a 100-ml recovery flask, and the whole was stirred in a stream of nitrogen at 40° C. for 8 hours.

| | |
|---|---|
| Compound 1-1 (manufactured by SIGMA-ALDRICH): | 344 mg (2 mmole) |
| Compound 1-2 (manufactured by TOKYO CHEMICAL INDUSTRY, CO., LTD.): | 566 mg (2 mmole) |
| Pd(PPh$_3$)$_4$: | 0.1 g |
| Toluene: | 10 ml |
| Ethanol: | 5 ml |
| 2-M aqueous solution of sodium carbonate: | 10 ml |

After the completion of the reaction, the crystal was separated by filtration, and was washed with water, ethanol, and toluene. The resultant crystal was dried in a vacuum at 120° C., and then, 340 mg of Compound 1-3 were obtained (yield: 60%).

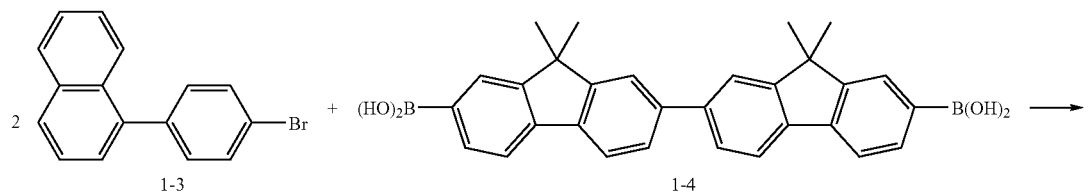

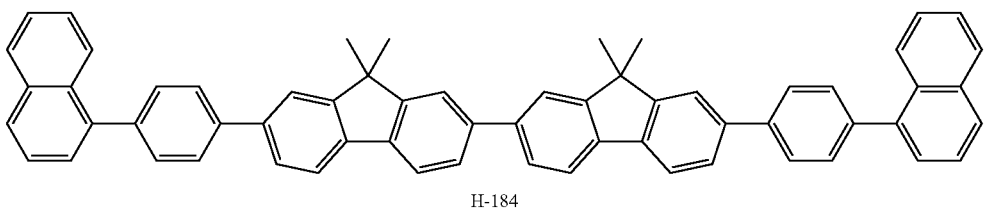

The following components were loaded into a 100-ml recovery flask, and the whole was stirred in a stream of nitrogen at 80° C. for 8 hours.

| | |
|---|---|
| Compound 1-3: | 283 mg (1 mmole) |
| Compound 1-4: | 237 mg (0.5 mmole) |
| Pd(PPh$_3$)$_4$: | 0.05 g |
| Toluene: | 10 ml |
| Ethanol: | 5 ml |
| 2-M aqueous solution of sodium carbonate: | 10 ml |

After the completion of the reaction, the crystal was separated by filtration, and was washed with water, ethanol, and toluene. The resultant crystal was dried in a vacuum at 120° C. and then subjected to sublimation purification, whereby 250 mg of Exemplified Compound No. H-184 were obtained (yield: 63%).

Matrix-assisted laser desorption/ionization time-of-flight mass spectrometry (MALDI-TOF MS) confirmed that the M+ of the compound was 790.3.

EXAMPLE 2

A device having three organic layers as shown in FIG. 1B was produced.

ITO having a thickness of 100 nm (transparent electrode 14) was patterned on a glass substrate (transparent substrate 15). The following organic layers and electrode layers were continuously formed on the ITO substrate by vacuum deposition based on resistance heating in a vacuum chamber having a pressure of $10^{-5}$ Pa in such a manner that the area in which the electrodes were opposed to each other would be 3 m$^2$

| | |
|---|---|
| Hole transport layer 13 (40 nm): | Compound A |
| Light emitting layer 12 (50 nm): | Exemplified Compound No. H-184: Compound B (16% in weight ratio):Compound C (4% in weight ratio) |
| Electron transport layer 16 (25 nm): | Bphen |
| Metal electrode 11-1 (1 nm): | KF |
| Metal electrode 11-2 (100 nm): | Al |

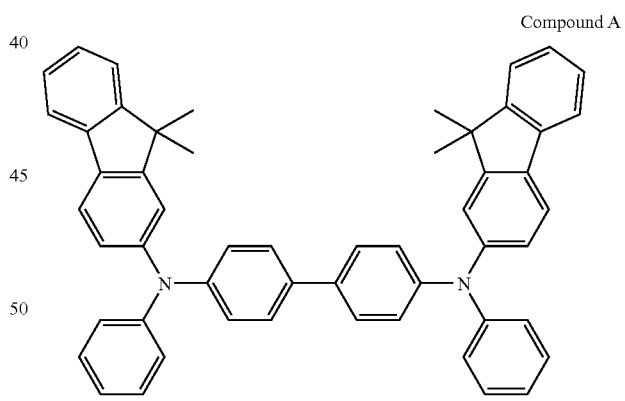

Compound A

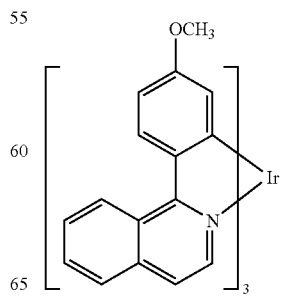

Compound B

-continued

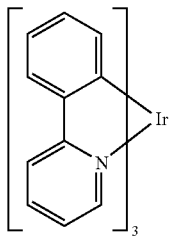

Compound C

The current-voltage characteristics of the EL device were measured with a microammeter "4140 B" (manufactured by Hewlett-Packard Development Company, L.P.), and the emission luminance of the device was measured with a "BM 7" (manufactured by TOPCON CORPORATION). The efficiency of the device of this example was such that the device showed a light intensity of 14.4 cd/A and a luminance of 12.9 lm/W (600 cd/m$^2$). In addition, the application of a voltage of 4 V caused the device to show a current value of 215 mA/cm$^2$.

EXAMPLE 3

Synthesis of Exemplified Compound No. H-185

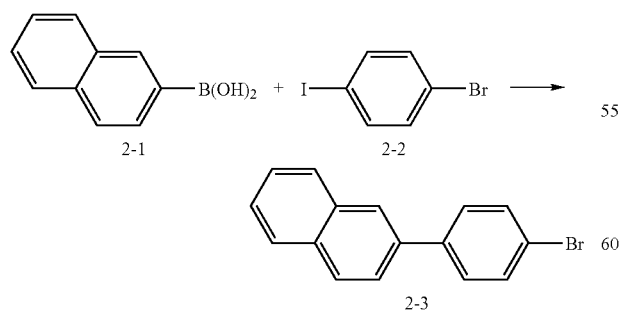

The following components were loaded into a 100-ml recovery flask, and the whole was stirred in a stream of nitrogen at 40° C. for 8 hours.

| | |
|---|---|
| Compound 2-1 (manufactured by SIGMA-ALDRICH): | 344 mg (2 mmole) |
| Compound 2-2 (manufactured by TOKYO CHEMICAL INDUSTRY, CO., LTD.): | 566 mg (2 mmole) |
| Pd(PPh$_3$)$_4$: | 0.1 g |
| Toluene: | 10 ml |
| Ethanol: | 5 ml |
| 2-M aqueous solution of sodium carbonate: | 10 ml |

After the completion of the reaction, the crystal was separated by filtration, and was washed with water, ethanol, and toluene. The resultant crystal was dried in a vacuum at 120° C., and then, 355 mg of Compound 2-3 were obtained (yield: 75%).

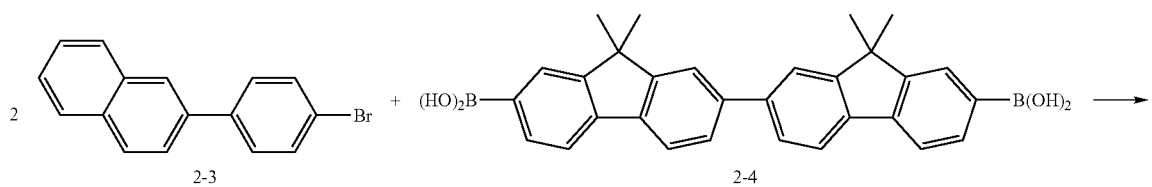

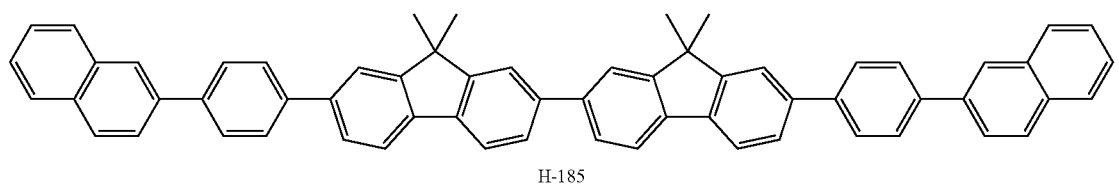

H-185

The following components were loaded into a 100-ml recovery flask, and the whole was stirred in a stream of nitrogen at 80° C. for 8 hours.

| | |
|---|---|
| Compound 2-3: | 283 mg (1 mmole) |
| Compound 2-4: | 237 mg (0.5 mmole) |
| Pd(PPh$_3$)$_4$: | 0.05 g |
| Toluene: | 10 ml |
| Ethanol: | 5 ml |
| 2-M aqueous solution of sodium carbonate: | 10 ml |

After the completion of the reaction, the crystal was separated by filtration, and was washed with water, ethanol, and toluene. The resultant crystal was dried in a vacuum at 120° C. and then subjected to sublimation purification, whereby 270 mg of Exemplified Compound No. H-185 were obtained (yield: 68%).

Matrix-assisted laser desorption/ionization time-of-flight mass spectrometry (MALDI-TOF MS) confirmed that the M+ of the compound was 790.3.

EXAMPLE 4

A device was produced in the same manner as in Example 2 except that Exemplified Compound No. H-185 was used instead of Exemplified Compound No. H-184, and the device was evaluated in the same manner as in Example 2. The efficiency of the device of this example was such that the device showed a light intensity of 10.6 cd/A and a luminance of 9.3 lm/W (600 cd/m²). In addition, the application of a voltage of 4 V caused the device to show a current value of 13.0 mA/cm².

EXAMPLE 5

Synthesis of Exemplified Compound No. H-1

Exemplified Compound No. H-1 was synthesized in the same manner as in Example 1 except that Compound 5-1 was used instead of Compound 1-4.

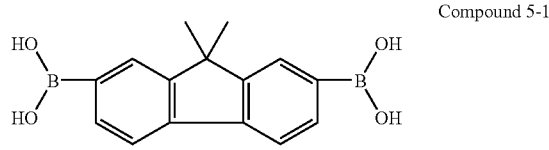

Compound 5-1

EXAMPLE 6

Synthesis of Exemplified Compound No. H-2

Exemplified Compound No. H-2 was synthesized in the same manner as in Example 3 except that Compound 5-1 was used instead of Compound 2-4.

EXAMPLE 7

Synthesis of Exemplified Compound No. H-7

Exemplified Compound No. H-7 was synthesized in the same manner as in Example 1 except that: Compound 7-1 (pyrene boric acid) was used instead of Compound 1-1; and Compound 5-1 was used instead of Compound 1-4.

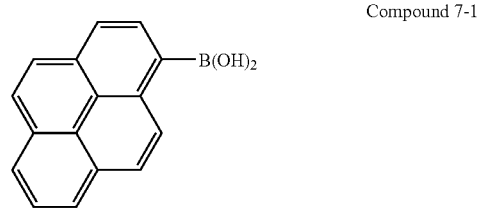

Compound 7-1

EXAMPLE 8

Synthesis of Exemplified Compound No. H-8

Exemplified Compound No. H-8 was synthesized in the same manner as in Example 1 except that: Compound 8-1 was used instead of Compound 1-1; and Compound 5-1 was used instead of Compound 1-4.

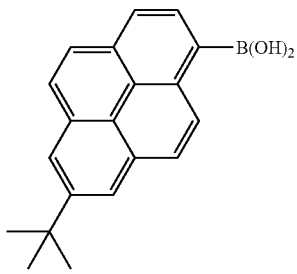

Compound 8-1

EXAMPLE 9

Synthesis of Exemplified Compound No. H-17

A reaction was performed by using 783 mg (3 mmol) of Compound 9-1 instead of Compound 1-1 of Example 1 and 1,018 mg (3.6 mmol) of Compound 1-2. After the completion of the reaction, the resultant was washed with water. After having been concentrated, the resultant was purified by means of silica gel chromatography (heptane:toluene=10:1), whereby 540 mg of Compound 9-2 were obtained. A reaction was performed in the same manner as in Example 1 except that 350 mg (1 mmol) of Compound 5-2 mentioned above and 450 mg (0.45 mmol) of Compound 5-1 instead of Compound 1-4 were used. After the reaction, 20 ml of water were added, and the whole was stirred for 10 minutes. After that, the resultant was filtered, and the resultant crystal was dissolved in chlorobenzene and subjected to hot filtration. The filtrate was recrystallized and subjected to sublimation purification, whereby 150 mg of Exemplified Compound No. H-17 were synthesized.

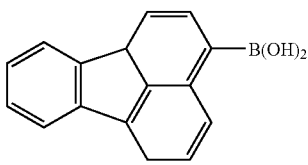

Compound 9-1

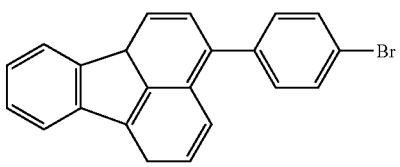

Compound 9-2

EXAMPLE 10

Synthesis of Exemplified Compound No. H-4

Exemplified Compound No. H-4 was synthesized in the same manner as in Example 1 except that: Compound 10-1 was used instead of Compound 1-1 of Example 1; and Compound 5-1 was used instead of Compound 1-4.

Compound 10-1

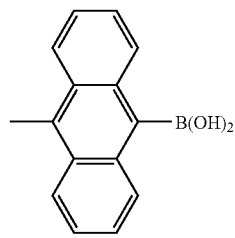

EXAMPLE 11

Synthesis of Exemplified Compound No. H-0.33

Exemplified Compound No. H-33 was synthesized in the same manner as in Example 1 except that: Compound 10-1 was used instead of Compound 1-1 of Example 1; and Compound 11-1 was used instead of Compound 1-4.

Compound 11-1

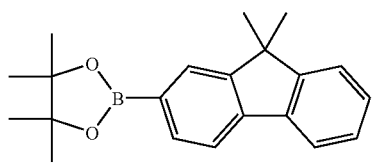

EXAMPLE 12

Synthesis of Exemplified Compound No. H-34

Exemplified Compound No. H-34 was synthesized in the same manner as in Example 1 except that: Compound 12-1 was used instead of Compound 1-1 of Example 1; and Compound 11-1 was used instead of Compound 1-4.

Compound 12-1

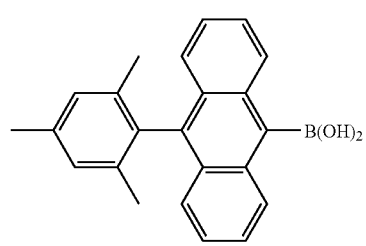

EXAMPLE 13

Synthesis of Exemplified Compound No. H-35

Exemplified Compound No. H-35 was synthesized in the same manner as in Example 1 except that: Compound 7-1 was used instead of Compound 1-1 of Example 1; and Compound 11-1 was used instead of Compound 1-4.

EXAMPLE 14

Synthesis of Exemplified Compound No. H-36

Exemplified Compound No. H-36 was synthesized in the same manner as in Example 1 except that: Compound 7-1 was used instead of Compound 1-1 of Example 1; and Compound 14-1 was used instead of Compound 1-4.

Compound 14-1

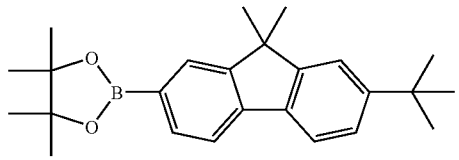

EXAMPLE 15

Synthesis of Exemplified Compound No. H-37

Exemplified Compound No. H-37 was synthesized in the same manner as in Example 1 except that: Compound 8-1 was used instead of Compound 1-1 of Example 1; and Compound 11-1 was used instead of Compound 1-4.

The maximum luminous wavelength in a toluene solution was 413 nm. Matrix-assisted laser desorption/ionization time-of-flight mass spectrometry (MALDI-TOF MS) confirmed that the M+ of the compound was 527.3.

EXAMPLE 16

Synthesis of Exemplified Compound No. H-43

Exemplified Compound No. H-43 was synthesized in the same manner as in Example 1 except that: Compound 9-1 was used instead of Compound 1-1 of Example 1; and Compound 11-1 was used instead of Compound 1-4.

The maximum luminous wavelength in a toluene solution was 464 nm. Matrix-assisted laser desorption/ionization time-of-flight mass spectrometry (MALDI-TOF MS) confirmed that the M+ of the compound was 471.2

The structure of the compound was confirmed by means of NMR measurement.

$^1$H NMR (CDCl$_3$, 400 MHz)σ(ppm): 8.03-8.02 (d, 2H), 8.00-7.98 (d, 1H), 7.95-9.94 (dd, 2H), 7.84-7.83 (d, 3H), 7.78-7.64 (m, 7H), 7.48-7.47 (d, 1H), 7.42-7.34 (m, 4H), 6.97 (s, 6H)

EXAMPLE 17

Synthesis of Exemplified Compound No. H-50

Exemplified Compound No. H-50 was synthesized in the same manner as in Example 1 except that: Compound 17-1 was used instead of Compound 1-1 of Example 1; and Compound 11-1 was used instead of Compound 1-4.

Compound 17-1

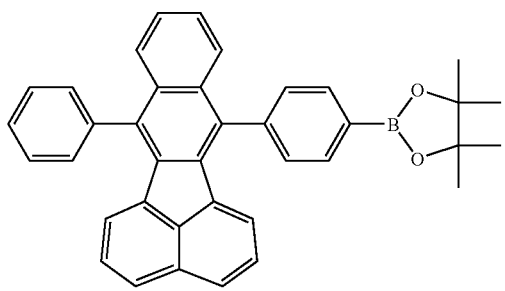

EXAMPLE 18

Synthesis of Exemplified Compound No. H-62

Exemplified Compound No. H-62 was synthesized in the same manner as in Example 1 except that: Compound 17-1 was used instead of Compound 1-1 of Example 1; and Compound 5-1 was used instead of Compound 1-4.

EXAMPLE 19

Synthesis of Exemplified Compound No. H-63

Exemplified Compound No. H-62 was synthesized in the same manner as in Example 1 except that: Compound 19-1 was used instead of Compound 1-1 of Example 1; and Compound 5-1 was used instead of Compound 1-4.

Compound 19-1

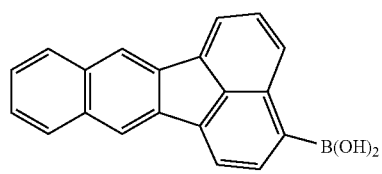

EXAMPLE 20

Synthesis of Exemplified Compound No. H-106

Exemplified Compound No. H-106 was synthesized in the same manner as in Example 1 except that Compound 20-1 was used instead of Compound 2-4 of Example 3.

Compound 20-1

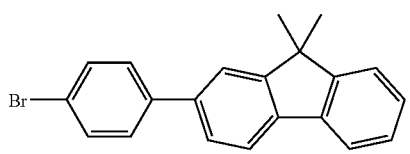

EXAMPLE 21

Synthesis of Exemplified Compound No. H-107

Exemplified Compound No. H-107 was synthesized in the same manner as in Example 1 except that: Compound 7-1 was used instead of Compound 1-1 of Example 1; and Compound 20-1 was used instead of Compound 1-4.

EXAMPLE 22

Synthesis of Exemplified Compound No. H-108

Exemplified Compound No. H-108 was synthesized in the same manner as in Example 1 except that: Compound 8-1 was used instead of Compound 1-1 of Example 1; and Compound 20-1 was used instead of Compound 1-4.

EXAMPLE 23

Synthesis of Exemplified Compound No. H-105

Exemplified Compound No. H-105 was synthesized in the same manner as in Example 1 except that Compound 20-1 was used instead of Compound 1-1 and Compound 1-4 of Example 1.

EXAMPLE 24

Synthesis of Exemplified Compound No. H-110

Exemplified Compound No. H-110 was synthesized in the same manner as in Example 1 except that: Compound 9-1 was used instead of Compound 1-1 of Example 1; and Compound 20-1 was used instead of Compound 1-4.

EXAMPLE 25

Synthesis of Exemplified Compound No. H-111

Exemplified Compound No. H-111 was synthesized in the same manner as in Example 1 except that: Compound 10-1 was used instead of Compound 1-1 of Example 1; and Compound 20-1 was used instead of Compound 1-4.

EXAMPLE 26

Synthesis of Exemplified Compound No. H-219

Exemplified Compound No. H-219 was synthesized in the same manner as in Example 1 except that: Compound 8-1 was used instead of Compound 1-1 of Example 1; and Compound 27-1 was used instead of Compound 1-4.

Compound 27-1

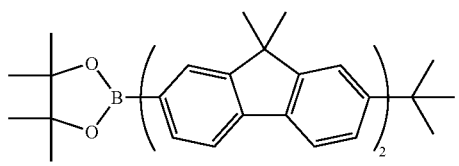

EXAMPLE 27

Synthesis of Exemplified Compound No. H-191

Exemplified Compound No. H-191 was synthesized in the same manner as in Example 1 except that: Compound 8-1 was used instead of Compound 1-1 of Example 1; and Compound 28-1 was used instead of Compound 1-4.

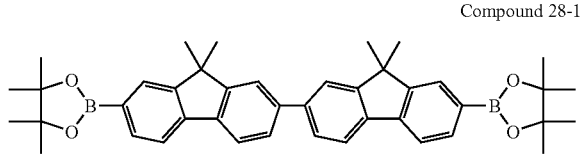

Compound 28-1

EXAMPLE 28

Synthesis of Exemplified Compound No. H-200

Exemplified Compound No. H-200 was synthesized in the same manner as in Example 1 except that: Compound 9-1 was used instead of Compound 1-1 of Example 1; and Compound 28-1 was used instead of Compound 1-4.

EXAMPLE 29

Synthesis of Exemplified Compound No. H-212

Exemplified Compound No. H-212 was synthesized in the same manner as in Example 1 except that Compound 30-1 was used instead of Compound 1-1 and Compound 1-4 of Example 1.

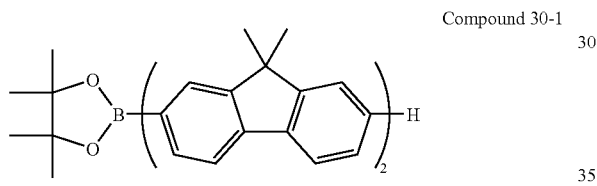

Compound 30-1

EXAMPLE 30

Synthesis of Exemplified Compound No. H-214

Exemplified Compound No. H-214 was synthesized in the same manner as in Example 1 except that: Compound 10-1 was used instead of Compound 1-1 of Example 1; and Compound 30-1 was used instead of Compound 1-4.

EXAMPLE 31

Synthesis of Exemplified Compound No. H-216

Exemplified Compound No. H-216 was synthesized in the same manner as in Example 1 except that: Compound 7-1 was used instead of Compound 1-1 of Example 1; and Compound 30-1 was used instead of Compound 1-4.

The maximum luminous wavelength in a toluene solution was 431 nm. Matrix-assisted laser desorption/ionization time-of-flight mass spectrometry (MALDI-TOF MS) confirmed that the M+ of the compound was 661.3.

EXAMPLE 32

Synthesis of Exemplified Compound No. H-218

Exemplified Compound No. H-218 was synthesized in the same manner as in Example 1 except that: Compound 8-1 was used instead of Compound 1-1 of Example 1; and Compound 30-1 was used instead of Compound 1-4.

The maximum luminous wavelength in a toluene solution was 448 nm. Matrix-assisted laser desorption/ionization time-of-flight mass spectrometry (MALDI-TOF MS) confirmed that the M+ of the compound was 719.3.

The structure of the compound was confirmed by means of NMR measurement.

$^1$H NMR (CDCl$_3$, 400 MHz)σ(ppm): 8.27-8.21 (m, 4H), 8.01 (s, 2H), 8.05-8.01 (dd, 2H), 7.90-7.85 (dd, 4H), 7.83-7.81 (d, 2H), 7.78-7.72 (m, 6H), 7.70-7.66 (t, 2H), 7.48-7.47 (d, 1H), 7.39-7.34 (s, 2H), 1.66-1.49 (m, 21H)

EXAMPLE 33

Synthesis of Exemplified Compound No. H-224

Exemplified Compound No. H-224 was synthesized in the same manner as in Example 1 except that: Compound 9-1 was used instead of Compound 1-1 of Example 1; and Compound 30-1 was used instead of Compound 1-4.

EXAMPLE 34

Synthesis of Exemplified Compound No. H-213

Exemplified Compound No. H-213 was synthesized in the same manner as in Example 1 except that: Compound 30-1 was used instead of Compound 2-1 and Compound 2-4 of Example 3.

EXAMPLE 35

Synthesis of Exemplified Compound No. H-228

Exemplified Compound No. H-228 was synthesized in the same manner as in Example 1 except that: Compound 9-1 was used instead of Compound 1-1 of Example 1; and Compound 27-1 was used instead of Compound 1-4.

EXAMPLE 36

Synthesis of Exemplified Compound No. H-230

Exemplified Compound No. H-230 was synthesized in the same manner as in Example 1 except that: Compound 19-1 was used instead of Compound 1-1 of Example 1; and Compound 27-1 was used instead of Compound 1-4.

EXAMPLE 37

Synthesis of Exemplified Compound No. H-231

Exemplified Compound No. H-231 was synthesized in the same manner as in Example 1 except that: Compound 17-1 was used instead of Compound 1-1 of Example 1; and Compound 30-1 was used instead of Compound 1-4.

EXAMPLE 38

Synthesis of Exemplified Compound No. H-233

Exemplified Compound No. H-233 was synthesized in the same manner as in Example 1 except that: Compound 39-1 was used instead of Compound 1-1 of Example 1; and Compound 30-1 was used instead of Compound 1-4.

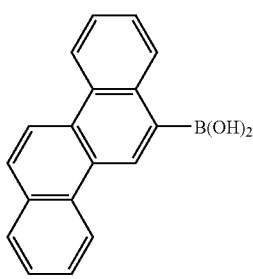

Compound 39-1

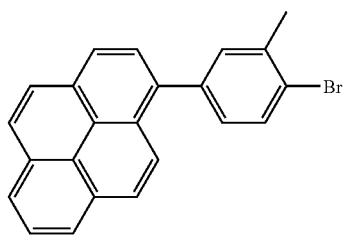

Compound 41-1

EXAMPLE 39

Synthesis of Exemplified Compound No. H-232

Exemplified Compound No. H-232 was synthesized in the same manner as in Example 1 except that: Compound 9-1 was used instead of Compound 1-1 of Example 1; and Compound 30-1 was used instead of Compound 1-4.

EXAMPLE 40

Synthesis of Exemplified Compound No. H-107

Exemplified Compound No. H-282 was synthesized in the same manner as in Example 1 except that: Compound 7-1 was used instead of Compound 1-1 of Example 1; and Compound 40-1 obtained by turning bromine of Compound 20-1 into pinacolborane was used instead of Compound 1-4. The maximum luminous wavelength in toluene was 437 nm. Matrix-assisted laser desorption/ionization time-of-flight mass spectrometry (MALDI-TOF MS) confirmed that the M+ of the compound was 545.2.

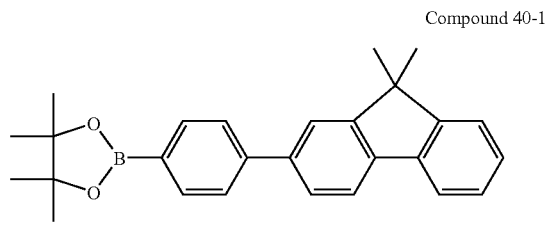

Compound 40-1

EXAMPLE 41

Synthesis of Exemplified Compound No. H-385

Exemplified Compound No. H-385 was synthesized in the same manner as in Example 1 except that: Compound 41-1 was used instead of Compound 1-1 of Example 1; and Compound 5-1 was used instead of Compound 1-4.

EXAMPLE 42

Synthesis of Exemplified Compound No. H-388

Exemplified Compound No. H-385 was synthesized by: causing Compound 1-3 instead of Compound 1-1 of Example 1 and Compound 5-1 instead of Compound 1-4 equal to each other in used amount to react with each other; and causing the resultant intermediate to react with Compound 41-1 in the same manner as in Example 1.

EXAMPLE 43 TO 140

A device having three organic layers as shown in FIG. 1B was produced.

ITO having a thickness of 100 nm (transparent electrode 14) was patterned on a glass substrate (transparent substrate 15). The following organic layers and electrode layers were continuously formed on the ITO substrate by vacuum deposition based on resistance heating in a vacuum chamber having a pressure of $10^{-5}$ Pa in such a manner that the area in which the electrodes were opposed to each other would be 3 $mm^2$.

| Hole transport layer 13 (40 nm): | Compound HTL |
| Light emitting layer 12 (50 nm): | Exemplified |

Compound HOST 1:Compound HOST 2 (20% or 0% in weight ratio):Compound GUEST (5% in weight ratio) Electron transport layer 16 (25 nm):Compound ETL

| Metal electrode 11-1 (1 nm): | KF |
| Metal electrode 11-2 (100 nm): | Al |

The compound numbers of HTL, HOST 1, HOST 2, GUEST, and ETL of each of the above constitutions, and the luminescent color and half lifetime of a device produced by using them are shown below.

| | | Compound name | | | | Half lifetime | Initial luminance | Luminescent |
| --- | --- | --- | --- | --- | --- | --- | --- | --- |
| Example | ETL | HOST1 | HOST2 | GUEST | HTL | (hour) | (cd/m2) | color |
| 43 | E1 | H-8 | — | D-3 | HT-4 | 1250 | 1000 | green |
| 44 | E1 | H-3 | — | D-20 | HT-3 | 2000 | 300 | blue |
| 45 | E1 | H-3 | — | H-20 | HT-10 | 800 | 300 | blue |

-continued

| Example | ETL | HOST1 | HOST2 | GUEST | HTL | Half lifetime (hour) | Initial luminance (cd/m2) | Luminescent color |
|---|---|---|---|---|---|---|---|---|
| 46 | E1 | H-13 | D53 | D-39 | HT-5 | 1000 | 1500 | green |
| 47 | E1 | H-10 | HT-6 | D-26 | HT-5 | 1000 | 500 | blue |
| 48 | E1 | H-10 | — | D-31 | HT-1 | 800 | 700 | blue |
| 49 | E1 | H-10 | HT-7 | D-18 | HT-5 | 1200 | 1200 | green |
| 50 | E1 | H-10 | HT-6 | D-20 | HT-10 | 1800 | 1500 | green |
| 51 | E1 | H-36 | HT-4 | D-21 | HT-7 | 2500 | 1500 | green |
| 52 | E1 | H-37 | — | H-43 | HT-10 | 1700 | 600 | blue |
| 53 | E1 | H-55 | — | D-8 | HT-3 | 1500 | 250 | blue |
| 54 | E1 | H-53 | — | D-40 | HT-5 | 2500 | 600 | red |
| 55 | E1 | H-53 | — | D-52 | HT-5 | 1500 | 500 | red |
| 56 | E1 | H-60 | — | D-40 | HT-1 | 3500 | 500 | red |
| 57 | E1 | H-74 | HT-7 | D-19 | HT-1 | 1500 | 1000 | green |
| 58 | E1 | H-85 | D-39 | D-53 | HT-3 | 2500 | 300 | red |
| 59 | E1 | H-107 | — | D-31 | HT-2 | 2000 | 500 | blue |
| 60 | E1 | H-107 | — | D-33 | HT-3 | 2500 | 600 | blue |
| 61 | E1 | H-108 | — | D-27 | HT-5 | 2500 | 300 | blue |
| 62 | E1 | H-116 | D-41 | D-57 | HT-6 | 700 | 600 | red |
| 63 | E1 | H-122 | — | D-40 | HT-10 | 1000 | 400 | red |
| 64 | E1 | H-145 | D-18 | D-34 | HT-6 | 2500 | 500 | red |
| 65 | E1 | H-173 | — | D-7 | HT-5 | 1500 | 200 | blue |
| 66 | E1 | H-174 | — | D-20 | HT-5 | 2000 | 300 | blue |
| 67 | E1 | H-184 | — | D-3 | HT-6 | 1000 | 1200 | green |
| 68 | E1 | H-184 | — | D-40 | HT-5 | 2000 | 600 | red |
| 69 | E1 | H-184 | — | D-54 | HT-8 | 2500 | 500 | red |
| 70 | E1 | H-187 | — | D-2 | HT-7 | 3000 | 1200 | green |
| 71 | E1 | H-212 | — | D-40 | HT-3 | 2200 | 500 | red |
| 72 | E1 | H-213 | D-39 | D-40 | HT-10 | 6000 | 500 | red |
| 73 | E1 | H-213 | — | D-23 | HT-5 | 3000 | 300 | blue |
| 74 | E1 | H-216 | — | D-19 | HT-3 | 2400 | 1000 | green |
| 75 | E1 | H-216 | HT-4 | D-19 | HT-3 | 3000 | 1000 | green |
| 76 | E1 | H-218 | HT-4 | D-18 | HT-5 | 2500 | 1200 | green |
| 77 | E1 | H-225 | HT-4 | D-27 | HT-3 | 1500 | 300 | blue |
| 78 | E1 | H-225 | — | D-18 | HT-4 | 1200 | 1500 | green |
| 79 | E1 | H-225 | — | D-20 | HT-1 | 800 | 300 | blue |
| 80 | E1 | H-213 | HT-6 | D-21 | HT-3 | 1000 | 1200 | green |
| 81 | E1 | H-223 | HT-4 | D-19 | HT-3 | 1500 | 1000 | green |
| 82 | E1 | H-223 | — | D-28 | HT-3 | 2300 | 600 | blue |
| 83 | E1 | H-223 | — | D-2 | HT-10 | 2000 | 1200 | green |
| 84 | E1 | H-223 | — | D-31 | HT-7 | 1700 | 350 | blue |
| 85 | E1 | H-218 | — | D-18 | HT-3 | 2300 | 1200 | green |
| 86 | E1 | H-216 | — | D-18 | HT-5 | 2500 | 1000 | green |
| 87 | E1 | H-218 | HT-7 | D-4 | HT-5 | 3200 | 1500 | green |
| 88 | E1 | H-281 | D-39 | D-40 | HT-10 | 3000 | 500 | red |
| 89 | E1 | H-281 | — | D-53 | HT-5 | 4000 | 350 | red |
| 90 | E1 | H-281 | — | D-9 | HT-10 | 2500 | 300 | blue |
| 91 | E1 | H-281 | — | D-25 | HT-5 | 1300 | 500 | blue |
| 92 | E1 | H-282 | — | D-33 | HT-3 | 3000 | 500 | blue |
| 93 | E1 | H-282 | — | D-4 | HT-4 | 1500 | 1000 | green |
| 94 | E1 | H-282 | — | D-19 | HT-3 | 1800 | 1200 | green |
| 95 | E1 | H-284 | — | D-18 | HT-5 | 2500 | 1200 | green |
| 96 | E1 | H-284 | — | D-27 | HT-5 | 2500 | 300 | blue |
| 97 | E1 | H-285 | — | D-34 | HT-6 | 1000 | 500 | red |
| 98 | E1 | H-300 | — | D-38 | HT-2 | 3000 | 800 | yellow |
| 99 | E1 | H-223 | — | D-21 | HT-5 | 2600 | 1500 | green |
| 100 | E1 | H-360 | D-39 | D-40 | HT-5 | 4000 | 500 | red |
| 101 | E1 | H-361 | — | D-40 | HT-5 | 3500 | 500 | red |
| 102 | E1 | H-360 | D-39 | D-52 | HT-8 | 4500 | 500 | red |
| 103 | E1 | H-361 | D-55 | D-53 | HT-8 | 2500 | 500 | red |
| 104 | E1 | H-361 | — | D-18 | HT-10 | 3000 | 1200 | green |
| 105 | E1 | H-364 | — | D-3 | HT-1 | 1500 | 500 | green |
| 106 | E1 | H-364 | — | D-33 | HT-5 | 3500 | 300 | blue |
| 107 | E1 | H-384 | — | D-20 | HT-5 | 1500 | 1000 | blue |
| 108 | E1 | H-387 | — | D-56 | HT-3 | 1000 | 1200 | green |
| 109 | E1 | H-388 | — | D-18 | HT-5 | 2500 | 1500 | green |
| 110 | E2 | H-1 | — | D-20 | HT-5 | 500 | 500 | blue |
| 111 | E2 | H-8 | — | H-17 | HT-10 | 1200 | 300 | blue |
| 112 | E2 | H-223 | — | D-3 | HT-10 | 2000 | 1300 | green |
| 113 | E2 | H-195 | — | D-40 | HT-5 | 3000 | 500 | red |
| 114 | E3 | H-37 | — | D-31 | HT-8 | 1500 | 200 | blue |
| 115 | E3 | H-223 | — | D-17 | HT-5 | 1000 | 200 | blue |
| 116 | E3 | H-379 | — | D-18 | HT-6 | 2200 | 1000 | green |
| 117 | E3 | H-361 | — | D-53 | HT-3 | 1000 | 500 | red |
| 118 | E3 | H-361 | HT-6 | D-40 | HT-5 | 800 | 600 | red |
| 119 | E3 | H-382 | HT-4 | D-19 | HT-3 | 650 | 1000 | green |
| 120 | E3 | H-385 | — | D-31 | HT-9 | 2200 | 200 | blue |

-continued

| Example | ETL | HOST1 | HOST2 | GUEST | HTL | Half lifetime (hour) | Initial luminance (cd/m2) | Luminescent color |
|---|---|---|---|---|---|---|---|---|
| 121 | E4 | H-53 | D-41 | D-57 | HT-2 | 3500 | 400 | red |
| 122 | E4 | H-107 | — | D-27 | HT-5 | 1000 | 300 | blue |
| 123 | E4 | H-109 | HT-10 | D-34 | HT-5 | 2000 | 500 | red |
| 124 | E4 | H-223 | — | D-29 | HT-5 | 1600 | 200 | blue |
| 125 | E5 | H-3 | — | D-26 | HT-7 | 500 | 500 | blue |
| 126 | E5 | H-19 | — | D-23 | HT-5 | 700 | 400 | blue |
| 127 | E5 | H-19 | HT-4 | D-18 | HT-5 | 2000 | 1000 | green |
| 128 | E5 | H-99 | D-41 | D-57 | HT-1 | 2500 | 500 | red |
| 129 | E5 | H-223 | — | D-31 | HT-5 | 2000 | 300 | blue |
| 130 | E5 | H-281 | — | D-33 | HT-7 | 1500 | 500 | blue |
| 131 | E6 | H-13 | — | D-39 | HT-8 | 1500 | 1000 | green |
| 132 | E6 | H-13 | — | D-56 | HT-5 | 2000 | 1500 | green |
| 133 | E6 | H-107 | HT-4 | D-18 | HT-3 | 1000 | 1500 | green |
| 134 | E6 | H-213 | — | D-40 | HT-5 | 3000 | 500 | red |
| 135 | E6 | H-216 | HT-4 | D-19 | HT-3 | 1500 | 1000 | green |
| 136 | E6 | H-223 | — | D-25 | HT-5 | 800 | 300 | blue |
| 137 | E6 | H-223 | — | D-40 | HT-5 | 3500 | 400 | red |
| 138 | E6 | H-291 | — | D-40 | HT-8 | 3000 | 400 | red |
| 139 | E6 | H-364 | — | D-33 | HT-3 | 1000 | 200 | blue |
| 140 | E6 | H-382 | — | D-17 | HT-7 | 1500 | 200 | blue |

Each of those devices was able to provide light emission having a long lifetime in a favorable manner by using the compound of the present invention.

This application claims priority from Japanese Patent Application Nos. 2005-366205 filed on Dec. 20, 2005, 2006-111726 filed on Apr. 14, 2006, and 2006-327780 filed on Dec. 5, 2006, which are hereby incorporated by reference herein.

The invention claimed is:

1. A fluorene compound represented by the following formula:

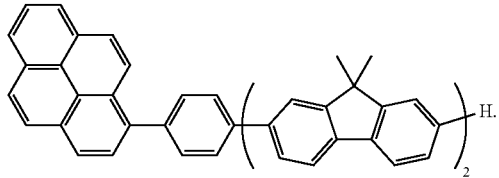

2. An organic electroluminescence device, comprising a layer containing an organic compound, the layer being interposed between a pair of electrodes, wherein the layer containing an organic compound comprises a layer containing the fluorene compound according to claim 1.

* * * * *